United States Patent
Rao et al.

(10) Patent No.: US 11,567,081 B2
(45) Date of Patent: Jan. 31, 2023

(54) METHOD OF ISOLATING CIRCULATING TUMOR CELLS

(71) Applicant: Duke University, Durham, NC (US)

(72) Inventors: Galla Chandra Rao, Princeton Junction, NJ (US); Mark C. Connelly, Doylestown, PA (US); Mariano A. Garcia-Blanco, Hillsborough, NC (US); Andrew J. Armstrong, Chapel Hill, NC (US); Rhonda L. Bitting, Durham, NC (US)

(73) Assignees: Duke University, Durham, NC (US); Menarini Silicon Biosystems S.p.A., Bologna (IT)

( * ) Notice: Subject to any disclaimer, the term of this patent is extended or adjusted under 35 U.S.C. 154(b) by 224 days.

(21) Appl. No.: 16/206,932

(22) Filed: Nov. 30, 2018

(65) Prior Publication Data
US 2019/0107542 A1  Apr. 11, 2019

Related U.S. Application Data

(62) Division of application No. 14/765,071, filed as application No. PCT/US2013/043745 on May 31, 2013, now Pat. No. 10,161,939.

(60) Provisional application No. 61/806,358, filed on Mar. 28, 2013, provisional application No. 61/760,042, filed on Feb. 2, 2013.

(51) Int. Cl.
| | | |
|---|---|---|
| G01N 33/574 | (2006.01) | |
| G01N 33/543 | (2006.01) | |
| G01N 33/569 | (2006.01) | |

(52) U.S. Cl.
CPC . *G01N 33/57484* (2013.01); *G01N 33/54326* (2013.01); *G01N 33/56966* (2013.01); *G01N 33/57415* (2013.01); *G01N 33/57434* (2013.01); *G01N 33/57492* (2013.01); *G01N 2333/47* (2013.01); *G01N 2333/4703* (2013.01); *G01N 2333/4742* (2013.01); *G01N 2333/705* (2013.01); *G01N 2333/70503* (2013.01); *G01N 2333/70589* (2013.01); *G01N 2333/70596* (2013.01)

(58) Field of Classification Search
CPC ........... G01N 33/574; G01N 33/57484; G01N 33/54326; G01N 33/56966; G01N 33/57415; G01N 33/57434; G01N 33/57492
USPC .................................................... 424/133.1
See application file for complete search history.

(56) References Cited

U.S. PATENT DOCUMENTS

| | | | |
|---|---|---|---|
| 5,352,803 A | 10/1994 | Mattingly | |
| 5,359,093 A | 10/1994 | Adamczyk | |
| 5,496,925 A | 3/1996 | Mattingly | |
| 5,573,904 A | 11/1996 | Mattingly | |
| 5,593,896 A | 1/1997 | Adamczyk et al. | |
| 6,197,523 B1 | 3/2001 | Rimm et al. | |
| 6,355,623 B2 | 3/2002 | Seidman | |
| 6,433,149 B1 | 8/2002 | Blaschuk et al. | |
| 6,566,063 B1 | 5/2003 | Kaufmann et al. | |
| 6,645,731 B2 | 11/2003 | Terstappen et al. | |
| 7,056,660 B1 | 6/2006 | Giesieng | |
| 2002/0146687 A1 | 10/2002 | Blaschuk et al. | |
| 2002/0169106 A1 | 11/2002 | Blaschuk et al. | |
| 2007/0026417 A1 | 2/2007 | Fuchs et al. | |
| 2008/0261829 A1* | 10/2008 | Harvey | G01N 33/6854 506/13 |
| 2009/0305963 A1 | 12/2009 | Sukhatme et al. | |
| 2013/0171642 A1 | 7/2013 | Pestano et al. | |
| 2013/0209493 A1 | 8/2013 | Garcia-Blanco | |
| 2013/0255361 A1 | 10/2013 | Juncker et al. | |
| 2016/0077097 A1 | 3/2016 | Rao et al. | |

FOREIGN PATENT DOCUMENTS

| | | |
|---|---|---|
| WO | WO 2001/058956 A2 | 8/2001 |
| WO | WO 2005/043121 A2 | 5/2005 |
| WO | WO 2008/073603 A2 | 6/2008 |
| WO | WO 2009/036968 A1 | 3/2009 |
| WO | WO 2010/111388 A2 | 9/2010 |
| WO | WO 2011/093927 A1 | 8/2011 |
| WO | WO 2014/120265 A1 | 8/2014 |

OTHER PUBLICATIONS

Acloque, H., et al. "Epithelial-mesenchymal transitions: the importance of changing cell state in development and disease" J. Clin. Invest. 2009, 119, 1438-1449.
Adamczyk et al., "Chemiluminescence quenching of pteroic acid-N-sulfonylacridinium-9-carboxamide conjugates by folate binding protein," Bioorg. Med. Chem. Lett. 4: 2313-2317 (2004).
Adamczyk et al., "Chemiluminescent acridinium-9-carboxamide boronic acid probes: Application to a homogeneous glycated hemoglobin assay," Bioorg. Med. Chem. Lett. 16: 1324-1328 (2006).
Adamczyk et al., "Intrinsic factor-mediated modulation of cyanocobalamin-N-sulfonyl-acridinium-9-carboxamide chemiluminescence," Biorg. Med. Chem. Lett. 14: 3917-3921 (2004).
Adamczyk et al., "Regiodependent Luminescence Quenching of Biotinylated N-Sulfonyl-acridinium-9-carboxamides by Avidin," Org. Lett. 5: 3779-3782 (2003).
Aktas et al., "Stem cell and epithelial-mesenchymal transition markers are frequently overexpressed in circulating tumor cells of metastatic breast cancer patients" Breast Cancer Research, Current Science, London, GB, vol. 11, No. 4, Jul. 9, 2009, p. R46.

(Continued)

*Primary Examiner* — Yan Xiao
(74) *Attorney, Agent, or Firm* — Michael Best & Friedrich LLP

(57) ABSTRACT

Provided are methods for detecting or isolating circulating tumor cells (CTCs) in a subject. The methods may include detecting the expression of at least one epithelial mesenchymal transition (EMT) biomarker. Further provided are kits for detecting or isolating CTCs. The kits may include antibodies to at least one EMT biomarker. Further provided are methods of predicting the responsiveness of a subject to a cancer drug, methods of targeting delivery of a cancer drug in a subject, methods of providing a cancer prognosis to a subject, and methods for following the progress of cancer in a subject.

19 Claims, 23 Drawing Sheets

(56) References Cited

OTHER PUBLICATIONS

Allard et al. "Tumor Cells Circulate in the Peripheral Blood of All Major Carcinomas but not in Healthy Subjects or Patients With Nonmalignant Diseases," (2004) Clin Cancer Res 10:6897-6904.
Armstrong et al., "Circulating Tumor Cells from Patients with Advanced Prostate and Breast Cancer Displays Both Epithelial and Mesenchymal Markers" Molecular Cancer Research, 9(8) Aug. 2011, 11 pages.
Attard et al. "Characterization of ERG, AR and PTEN Gene Status in Circulating Tumor Cells from Patients with Castration-Resistant Prostate Cancer," (2009) Cancer Res 69:2912-2918.
Bitting et al., "Development of a method to isolate circulating tumor cells using mesenchymal-based capture," Methods 64 (2013) 129-136.
Bitting et al., "Evaluation of clinical phenotype, survival, and circulating tumor cell (CTC) enumeration in men with metastatic castration-resistant prostate cancer (mCRPC)." ASCO Meeting Abstracts Jun. 17, 2013:5031.
Bitting et al., "Isolation of circulating tumor cells using a novel EMT-based capture method." ASCO Meeting Abstracts May 30, 2012:10533.
Chu et al., "Cadherin-11 Promotes the Metastasis of Prostate Cancer Cells to Bone," Mol. Cancer Res. Aug. 2008; 1259-1267.
Haugland, Handbook of Fluorescent Probes and Research Chemicals (1996).
Hay, E.D., et al. "Transformations Between Epithelium and Mesenchyme: Normal, Pathological, and Experimentally Induced" Am. J. Kidney Dis. 1995, 26, 678-690.
Huang et al., "Cadherin-11 Increases Migration and Invasion of Prostate Cancer Cells and Enhances their Interaction with Osteoblasts," Cancer Res 2010;70:4580-4589.
Jérôme Doyen et al., "Circulating tumor cells in prostate cancer: a potential surrogate marker of survival" Critical Review in Oncology/Hematology, Dec. 31, 2012, pp. 241-256.
Masuda, N., et al., "Analysis of chemical modification of RNA from formalin-fixed samples and optimization of molcular biology applications for such samples" Nucleic Acids Res 1999, 27, 4436.
Nadri et al., "An efficient method tor isolation of murine bone marrow mesenchymal stem cells", Int. J. Dev. Biol., 2007, vol. 51, p. 723-729.
Oltean et al., "Alternative inclusion of fibroblast growth factor receptor 2 exon IIIc in Dunning prostate tumors reveals unexpected epithelial mesenchymal plasticity" Proc Natl Acad Sci USA 2006, 103, 14116-14121.
Polak and Van Noorden, Introduction to Immunocytochemistry, 3nd ed., Springer Verlag, N.Y. (2003).
Pollack V. et al., "Oncostatin M-induced effects on EMT in human proximal tubular cells: differential role of ERK signaling" American Journal of Physiology: Renal, Fluid and Electrolytephysiology, American Physiological Society, US, vol. 293, No. 5, Nov. 1, 2007, pp. F1714-F1726.
Pusztaszeri et al. "Immunohistochemical Expression of Endothelial Markers CD31, CD34, von Willebrand Factor, and Fli-1 in Normal Human Tissues," (2006) J Histochem Cytochem 54:385-395.
Scatena et al., Biochimica et Biophysica Acta, 2013, 1835: 129-143, available online Dec. 7, 2012.
Schneider et al., "Cadherin-11 contributes to pulmonary fibrosis: potential role in TGF-production and epithelial to mesenchymal transition," The FASEB Journal, vol. 26, Feb. 2012, 503-512.
Tomaskovic-Crook et al., "Epithelial to mesenchymal transition and breast cancer" Breast Cancer Research : BCR 2009, vol. 11, No. 6, 2009, p. 213.
Vodyanik et al., "A Mesoderm-Derived Precursor tor Mesenchymal Stem and Endothelial Cells", Cell Stem Cell, 2010, vol. 7, p. 718-729.
Wu, C., et al., "Simultaneous targeting of multiple disease mediators by a dual-variable-domain immunoglobulin," Nature Biotechnology, 25(11):1290-1297 (2007).
Zeisberg et al., "Discovery of Endothelialto Mesenchymal Transition as a Source tor Carcinoma-Associated Fibroblasts", Cancer Res., 2007, vol. 67, No. 21, p. 10123-8.
PCT/US2010/050223 International Search Report and Written Opinion dated Jan. 13, 2011 (8 pages).
European Patent Office Search Report for Application No. 10844915.8 dated Jun. 6, 2013 (12 pages).
Inernational Search Report and Written Opinion for Application No. PCT/US13/43745 dated Oct. 24, 2013 (18 pages).
European Patent Office Extended Search Report for Application No. 10844915.8 dated Mar. 7, 2014 (4 pages).
European Patent Office Action for Application No. 16152292.5 dated Apr. 8, 2016 (9 pages).
United States Patent Office Action for U.S. Appl. No. 13/575,638 dated Dec. 19, 2014 (19 pages).
United States Patent Office Final Action for U.S. Appl. No. 13/575,638 dated Aug. 21, 2015 (13 pages).
United States Patent Office Action for U.S. Appl. No. 13/575,638 dated Feb. 8, 2016 (18 pages).
Chinese Patent Office Action and Search Report for Application No. 201380075303.3 dated Mar. 31, 2016 (20 pages—including translation).
United States Patent Office Final Action for U.S. Appl. No. 13/575,638 dated Jul. 14, 2016 (20 pages).
United States Patent Office Action for U.S. Appl. No. 14/765,071 dated Oct. 27, 2016 (11 pages).
Chinese Patent Office Action for Application No. 201380075303.3 dated Jan. 17, 2017 (22 pages—including translation).
Great Britain Examination Report for Application No. 1514789.5 dated Feb. 17, 2017 (3 pages).
Great Britain Search and Examination Report for Application No. 1706134.2 dated May 4, 2017 (4 pages).
Great Britain Examination Report for Application No. 1514789.5 dated May 4, 2017 (3 pages).
United States Patent Office Action for U.S. Appl. No. 14/765,071 dated Jul. 6, 2017 (11 pages).
Chinese Patent Office Action for Application No. 201380075303.3 dated Jul. 19, 2017 (19 pages—including translation).
United States Patent Office Action for U.S. Appl. No. 14/765,071 dated Dec. 19, 2017 (13 pages).
Chinese Patent Office Action for Application No. 201380075303.3 dated Jan. 3, 2018 (11 pages, English translation included).
United States Patent Office Action for U.S. Appl. No. 14/765,071 dated May 31, 2018 (12 pages).

* cited by examiner

METHOD OF ISOLATING CIRCULATING TUMOR CELLS

CROSS REFERENCE TO RELATED APPLICATION

This patent application is a divisional of U.S. patent application Ser. No. 14/765,071, filed Jul. 31, 2015, which is a national stage filing under 35 U.S.C. § 371 of International Application No. PCT/US2013/043745, filed on May 31, 2013, which application claims priority to U.S. Provisional Application No. 61/760,042, filed Feb. 2, 2013, and U.S. Provisional Application No. 61/806,358, filed Mar. 28, 2013, each of which is incorporated herein by reference in its entirety.

SEQUENCE LISTING

The sequence listing is filed with the application in electronic format only and is incorporated by reference herein. The sequence listing text file "WO00_ASFILED_SequenceListing-Text" was created on May 31, 2013 and is 131,252 bytes in size.

STATEMENT REGARDING FEDERALLY SPONSORED RESEARCH

This invention was made with government support under federal grant number W81XWH-10-1-0483 awarded by the Department of Defense and federal grant number 5R01-CA127727-03 awarded by NIH. The U.S. Government has certain rights to this invention.

FIELD

The disclosure relates to methods for the detection and prognosis of cancer. Moreover, the disclosure provides methods for capturing and isolating circulating tumor cells (CTCs) that include the identification, detection, and optional enumeration of the CTCs that can be used in methods relating to a prognosis, diagnosis, or the treatment of cancer in a subject.

BACKGROUND

Most metazoan cells can be classified as either epithelial or mesenchymal based on morphology, behavior and molecular signatures. Epithelial tumor cells can become mesenchymal cells and vice versa via phenotypic transitions, a process known as epithelial plasticity. Epithelial cells are generally polar in the apico-basal direction, adherent to adjacent cells in the plane perpendicular to the polarity, and non-motile in the polar direction. Mesenchymal cells, in contrast, lack polarity, do not form tight interactions with neighboring cells, and are motile. In adult animals, epithelial and mesenchymal cells remain stably in one state or the other; that is, an epithelial cell does not change its properties and become mesenchymal. During development, however, epithelial cells of the early embryo give rise to all three embryonal layers (endoderm, mesoderm and ectoderm), which include mesenchymal cells (Hay, E.D., et al. *Am. J. Kidney Dis.* 1995, 26, 678-690). Therefore, these early embryonal cells have the ability to transition between epithelial and mesenchymal states. Embryos have been shown to undergo epithelial-mesenchymal transitions (EMTs) as well as mesenchymal-epithelial transitions (METs) (Acloque, H., et al. *J. Clin. Invest.* 2009, 119, 1438-1449).

Epithelial plasticity (EP) refers to the reversible loss of the epithelial cellular phenotype, a process known to occur during cancer metastasis. This EP biology has been linked in multiple studies to the risk of cancer metastasis and the acquisition of mesenchymal and/or stemness properties through the EMT process. EMT has been linked to chemoresistance, invasion, intravasation, and dissemination in multiple preclinical models of cancer. The MET process, which results in the re-expression of the epithelial phenotype, is also likely of great importance in development and metastasis and has been linked to metastatic colonization and survival of tumor cells in the metastatic niche. For example, in prostate cancer, mesenchymal biomarkers may be upregulated during androgen deprivation in prostate cancer cell lines, animal models, and in patient tumor specimens. Moreover, these biomarkers are plastic, revert upon replacement of testosterone, and are linked to an increased metastatic propensity and chemoresistance. Mesenchymal-like tumor cells may better promote local tumor invasion and intravasation/extravasation, but epithelial tumor cells may be necessary for eventual survival and proliferation in the metastatic niche, illustrating the potential relevance of the dual nature of EP in mediating the full process of metastasis.

Circulating tumor cells (CTCs), which are cells that have detached from a primary tumor and circulate in the bloodstream, have potential prognostic, predictive and surrogate implications in oncology. CTCs may constitute seeds for subsequent growth of additional tumors (metastasis) in different tissues. Thus, detection of CTCs can provide a diagnosis and/or prognosis for overall survival and therapeutic implications in subjects with cancers such as metastatic prostate and breast cancer. The number of CTCs in any patient sample (e.g., a blood sample) can be very small, which can make detection difficult. Current methods for detecting CTCs are based on the detection of epithelial cell adhesion molecule (EpCAM) expression, which is a biomarker associated with epithelial cells. However, during the process of metastasis, circulating tumor cells (CTCs) may lose their epithelial phenotype and acquire a mesenchymal phenotype that is not sufficiently captured by existing epithelial-based CTC technologies. During metastasis, tumor cells may exist as a spectrum of epithelial to mesenchymal phenotypes. CTCs may lose their epithelial phenotype and acquire a mesenchymal phenotype, which may not be captured with existing epithelial-based CTC technology and thus lead to the under-detection of CTCs under circumstances where cells undergo a decrease or loss of EpCAM expression, such as during biologic processes including EMT. Because of the role CTCs can play in the diagnosis, monitoring, and prognosis of disease in patients having cancer, any shortcoming in the detection technology needs to be addressed by the art.

There is recent evidence to suggest that CTCs with a mesenchymal phenotype are missed by CELLSEARCH® and other epithelial-based technologies. Accordingly, there is a need for methods and systems for capturing CTCs that do not rely on existing capture technologies, and methods for correlating CTC detection to diagnosis, monitoring, and prognosis of disease in cancer patients.

SUMMARY

In an aspect, the disclosure provides a method for detecting a circulating tumor cell (CTC) in a biological sample, the method comprising detecting at least one epithelial mesenchymal transition (EMT) biomarker in the biological sample.

In an aspect, the disclosure provides a kit for detecting a circulating tumor cell (CTC) in a biological sample, the kit comprising an antibody to at least one EMT biomarker and instructions for use.

In an aspect, the disclosure provides a method of predicting responsiveness of a subject having cancer to a course of cancer treatment, the method comprising: determining the level or presence of expression of at least one EMT biomarker to obtain an EMT biomarker profile and/or optionally a gene expression pattern for a CTC; and predicting the responsiveness of the subject to the cancer drug based on the EMT biomarker profile and/or optional gene expression pattern. In some embodiments the method includes: determining the level or presence of expression of at least one EMT biomarker in a sample from the subject to obtain a biomarker profile and optionally a gene expression pattern in a CTC for the subject; identifying the type of cancer from the biomarker profile and/or optional gene expression pattern, and optionally characterizing the stage of the cancer; and predicting responsiveness of the subject to the cancer drug based on any one of the biomarker pattern, the optional gene expression pattern, the type of cancer, or the stage of the cancer. Embodiments of this aspect can include detecting a number of cells captured and enumerated from a blood sample using at least one EMT biomarker applied to a sample from the subject. These cells that express the EMT biomarker are thereby captured using the EMT biomarker and could then be used to obtain a gene expression pattern in CTCs for the subject; to predict responsiveness of the subject to the cancer drug based on the obtained gene expression pattern, and for the detection of other biomarkers in these CTCs to assist in guiding therapy of that subject. These cells could also be used to measure the level of the specified EMT biomarker or other EMT biomarkers.

In an aspect, the disclosure provides a method of assessing the number of CTCs using both the traditional EpCAM based capture methodology and an EMT-marker based capture methodology. This EMT-based capture may replace or complement existing CTC capture technologies. The further capture, enumeration, and characterization of these CTCs using EMT antigen capture may further targeting delivery of a cancer drug in a subject having cancer comprising administering to the subject a cancer drug linked to an antibody specific for at least one EMT biomarker or specific drugs based on a gene expression profile or presence of this EMT biomarker.

In an aspect, the disclosure provides a method of estimating the prognosis of a subject with cancer as well as permitting a further characterization of CTCs that may predict for therapeutic responsiveness, the method comprising: determining the level of or presence of expression of at least one EMT biomarker in a sample from the subject to determine the number of CTCs in the subject and to obtain a gene expression pattern for the subject; and providing a prognosis to the subject based on the gene expression or biomarker profile pattern obtained.

In an aspect, the disclosure provides a method for monitoring progression of cancer in a subject undergoing therapeutic treatment, the method comprising detecting the level of expression or presence of expression of at least one EMT biomarker and the quantification of CTCs captured using this method in blood samples taken from the subject at a first and a second time; and comparing the first and second levels of expression; wherein a detected difference in the level of expression of the at least one EMT biomarker in the first and second samples over time indicates a change in the progression status of the cancer.

In an aspect, the disclosure provides a method for detecting cancer in a subject, the method comprising determining the presence of CTCs that express at least one EMT biomarker in a sample from the subject as compared to a normal or control sample, wherein an increased level of at least one EMT biomarker indicates presence of cancer progression or metastatic spread in the subject.

In an aspect, the disclosure provides a method of treating cancer in a subject comprising administering to the subject a cancer drug linked to an antibody that specifically binds at least one EMT biomarker.

The present disclosure is directed to a method for isolating, capturing, or enriching a circulating tumor cell from a patient, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby isolating, capturing, or enriching the circulating tumor cell. The method may further comprise confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The circulating tumor cell may have a mesenchymal phenotype. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method for detecting or identifying a circulating tumor cell in a patient, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby detecting or identifying the circulating tumor cell. The method may further comprise confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The circulating tumor cell may have a mesenchymal phenotype. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic. The present disclosure is directed to a method for isolating or capturing an intact cell from a patient, wherein the cell is β-catenin positive, DAPI positive, and CD45 negative, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the intact cell to form a solid phase-capture binding protein-intact cell complex; and separating the solid phase-capture binding protein-intact cell complex from the sample and unbound magnetic particle-capture binding protein complexes by application of an external magnetic field on the sample, thereby isolating or capturing the intact cell. The intact cell may have a mesenchymal phenotype. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of detecting and treating cancer in a subject, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, determining the level of circulating tumor cell in the solid phase-capture binding protein-circulating tumor cell complex; comparing the level of circulating tumor cell to a reference level of circulating tumor cell, detecting cancer in the subject if the level of circulating tumor cell is higher than the reference level of circulating tumor cell, cancer is detected in the subject, and administrating a therapy against cancer to the subject identified as having cancer. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, (β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of monitoring progression of cancer in a subject undergoing therapeutic treatment, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample; determining the level of circulating tumor cell in the solid phase-capture binding protein-circulating tumor cell complex; correlating the level of circulating tumor cell with the progression of cancer in the subject, wherein if the level of the circulating tumor cell is higher as compared to the level of the circulating tumor cell in an earlier biological sample from the subject, the subject is identified as having progression of cancer; and administering a therapy against cancer to the subject identified as having progression of cancer. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, (β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of determining a cancer prognosis in a subject, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample; determining the level of circulating tumor cell in the solid phase-capture binding protein-circulating tumor cell complex; comparing the level of circulating tumor cell to a reference level of circulating tumor cell, determining the cancer prognosis in the subject, wherein if the level of circulating tumor cell is higher than the reference level of circulating tumor cell, the subject is identified as having cancer, and administrating a therapy against cancer to the subject identified as having cancer. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of predicting responsiveness of a subject having cancer to a course of treatment, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample; determining the level of circulating tumor cell in the solid phase-capture binding protein-circulating tumor cell complex; and comparing the level of circulating tumor cell to a reference level of circulating tumor cell. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a kit for isolating or capturing a circulating tumor cell in a biological sample, the kit comprising an antibody linked to a magnetic particle, wherein the antibody binds specifically to at least one EMT biomarker and at least one staining reagent. The at least one EMT biomarker may include at least one of OB-cadherin, N-cadherin, vimentin, E-cadherin, FGFR2 splice variant isoforms, or CD133. The at least one staining reagent may include at least one of phycoerytherin-labeled anti-β-catenin antibody and an allophycocyanin-labeled anti-CD45 antibody.

Other aspects and embodiments of the disclosure will become apparent by consideration of the detailed description and accompanying drawings.

DETAILED DESCRIPTION

Figure 1:
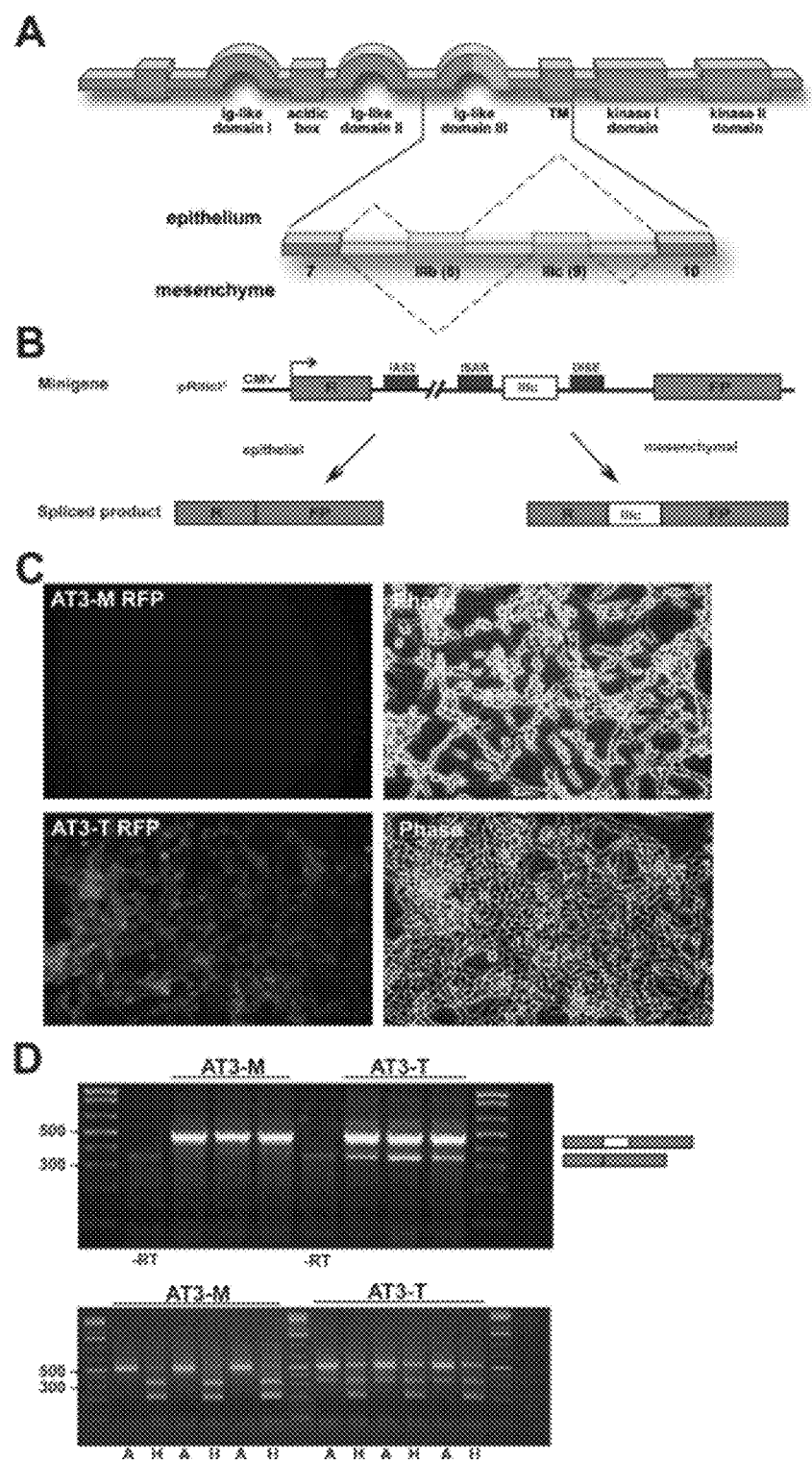
FIG. 1. (A) depicts a schematic representation of the IIIb and IIIc alternatively spliced isoforms of FGFR2. (B) is a schematic of the pRIIIcI$^2$ minigene and the fluorescence read-out. (C) is an RT-PCR analysis of the reporter (upper panel) and endogenous FGFR2 (lower panel). (D) are epifluorescence and phase-contrast pictures of clones AT3-M and AT3-T.

Before any embodiments are described in detail, it is to be understood that the claims are not limited to the details of construction and the arrangement of components set forth in the following description or illustrated in the included drawings.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

In a general sense, the disclosure provides biomarkers that have been identified to be associated with circulating tumor cells (CTCs). As described herein, one or more biomarkers of epithelial mesenchymal transition (EMT) are detectable on CTCs of patients afflicted with common epithelial malignancies. These transitional cells often display stem cell-like characteristics (stemness) and/or plasticity. Further, the disclosure provides description that metastatic propensity and epithelial phenotypic changes correlate with alternative splicing of the FGFR2 gene. The disclosure also provides that, as illustrated in the non-limiting Examples, transitional cells are found in cancer patients where many CTCs co-expressed biomarkers associated with epithelial and mesenchymal cells.

Thus, as described below EMT biomarker expression can be used to detect and quantify CTCs in a biological sample. Accordingly, methods comprising detection of EMT biomarker expression, or detection of CTCs, or a combination thereof, can be used to assess cancer prognosis, tumor invasiveness, risk of metastasis, or to stage tumors. As one of skill in the art will appreciate, any suitable method for evaluating EMT biomarker expression can be used to evaluate EMT biomarker expression according to the methods described herein including, but not limited to, detection with antibodies, real time RT-PCR, Northern analysis, Western analysis, and flow cytometry.

The disclosure also describes the development of a CTC capture method that is based on the biology of epithelial plasticity and isolates cells based on mesenchymal markers, such as N-cadherin or OB-cadherin cell surface expression. In patients with advanced breast and prostate cancer, EP biomarkers including OB-cadherin, N-cadherin, and vimentin can be detected in CTCs that are isolated by EpCAM-based ferromagnetic capture and co-express cytokeratin, which is expressed in epithelial cells. Similarly, CTCs expressing the mesenchymal markers twist and vimentin have been identified rarely in patients with early stage breast cancer but in the majority of patients with metastatic breast cancer, suggesting that transition to a mesenchymal phenotype may be important for metastasis. Furthermore, recent serial monitoring of CTCs with a mesenchymal phenotype, as defined by RNA fluorescence in situ hybridization (FISH), suggests that there may be an association between mesenchymal CTCs and disease progression in women with breast cancer.

As described herein, in patients with metastatic castration-resistant prostate cancer (CRPC) and breast cancer (BC), CTCs isolated using epithelial cell adhesion molecule (EpCAM) ferromagnetic capture expressed mesenchymal markers, including N- and OB-cadherin, suggesting phenotypic plasticity and the presence of EMT. The CTC capture method described herein involves a mesenchymal-based assay. This assay detected OB-cadherin cellular events present in men with metastatic prostate cancer but were less common in healthy individuals. This method may complement existing epithelial-based methods and may potentially be useful in patients with bone metastases.

Definitions

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody."

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region. The term "administration" or "administering," as used herein, refers to providing, contacting, and/or delivery of a cancer treatment by any appropriate route to achieve the desired effect. The cancer treatment may be administered to a subject in numerous ways including, but not limited to, orally, ocularly, nasally, intravenously, topically, as aerosols, suppository, etc. and may be used in combination.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

The term "biomarker" as used herein refers to any quantifiable biological component that is unique to a particular physiological condition (e.g., cancer). A biomarker may be a gene, an mRNA transcribed from said gene, or a protein translated from said mRNA. A measureable increase or decrease, of a biomarker level, relative to a control, such as an individual, group of individuals or populations, or alternatively, relative to subjects with cancer, may provide a diagnosis of a particular physiological condition.

"Breast cancer" as used herein refers to a type of cancer that originates from and develops in the breast.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Circulating tumor cells", "CTC" and "CTCs" as used interchangeably herein refers to cells that have shed into the vasculature from a primary tumor and circulate in the bloodstream. CTCs are considered seeds for subsequent growth of additional tumors (metastasis) in vital distant organs, triggering a mechanism that is responsible for the vast majority of cancer-related deaths.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/ solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

The term "effective dosage" as used herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual.

"Epithelial" and "epithelial phenotype" as used herein refer to membranous tissue composed of one or more layers of cells separated by very little intercellular substance and forming the covering the most internal and external surfaces of the body and its organs.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entirety). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

"Mesenchymal" and "mesenchymal phenotype" as used interchangeably herein refer to a type of undifferentiated loose connective tissue that can develop into the tissues of the lymphatic and circulatory systems and connective tissues throughout the body, such as bone and cartilage. Mesenchymal phenotypes may be characterized morphologically by a prominent ground substance matrix containing a loose aggregate of reticular fibrils and unspecialized cells. Mesenchymal cells can migrate easily, in contrast to epithelial cells, which lack mobility and are organized into closely adherent sheets, are polygonal in shape, and are polarized in an apical-basal orientation.

"Mesenchymal phenotypic CTC" and "mesenchymal CTC" as used interchangeably herein refer to a CTC which has a mesenchymal phenotype.

The term "normal control" or "healthy control" as used herein means a sample or specimen taken from a subject, or an actual subject who does not have cancer, or is not at risk of developing cancer.

The term "normal subject" as used herein means a healthy subject, i.e. a subject having no clinical signs or symptoms of cancer. The normal subject is clinically evaluated for otherwise undetected signs or symptoms of cancer, which evaluation may include routine physical examination and/or laboratory testing.

The term "predetermined cutoff" and "predetermined level" as used herein means an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Prostate cancer" as used herein refers to a type of cancer that develops in the prostate. Prostate cancer may be slow growing or aggressive, in which the cancer cells metastasize from the prostate to other parts of the body, particularly the bones and lymph nodes. "Metastatic prostate cancer" refers to prostate cancer that spreads outside the prostate gland to the lymph nodes, bones, or other areas. "Castration resistant prostate cancer" refers to prostate cancer disease progression despite androgen-deprivation therapy which may present as one or any combination of a continuous rise in serum levels of prostate-specific antigen, progression of pre-existing disease, or appearance of new metastases.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

The term "reference activity level" or "reference" as used herein means an activity level of the biomarker in a sample group that serves as a reference against which to assess the activity level in an individual or sample group.

The term "risk assessment," "risk classification," "risk identification," or "risk stratification" as used herein interchangeably, means an evaluation of factors including biomarkers, to predict the risk of occurrence of future events including disease onset or disease progression, so that treatment decisions regarding the subject may be made on a more informed basis.

The term "sample," "test sample," "specimen," "biological sample," "sample from a subject," or "subject sample" as used herein interchangeably, means a sample or isolate of blood, tissue, urine, serum, plasma, amniotic fluid, cerebrospinal fluid, placental cells or tissue, endothelial cells, leukocytes, or monocytes, can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art.

The term also means any biological material being tested for and/or suspected of containing an analyte of interest. The sample may be any tissue sample taken or derived from the subject. In some embodiments, the sample from the subject may comprise protein. Any cell type, tissue, or bodily fluid may be utilized to obtain a sample. Such cell types, tissues, and fluid may include sections of tissues such as biopsy and autopsy samples, frozen sections taken for histological purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

Methods well-known in the art for collecting, handling and processing urine, blood, serum and plasma, and other body fluids, are used in the practice of the present disclosure. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples, a pre-processed archived sample, etc.), pretreatment of the sample is an option that can be performed for mere convenience (e.g., as part of a protocol on a commercial platform). The sample may be used directly as obtained from the subject or following pretreatment to modify a characteristic of the sample. Pretreatment may include extraction, concentration, inactivation of interfering components, and/or the addition of reagents.

"Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. For example, the linking agent can include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. For examples, the solid phase can be plastic, derivatized plastic, magnetic, paramagnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human. In some embodiments, the subject or subject may be a human or a non-human. In some embodiments, the subject may be a human subject at risk for developing or already having cancer.

"Treat", "treating" or "treatment" are each used interchangeably herein to describe reversing, alleviating, or inhibiting the progress of a disease, such as cancer, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

As described herein the ability for a cell to transition easily between epithelial-like and mesenchymal-like states (phenotypic plasticity) is a relevant determinant of malignant fitness more so than the properties of the end states. While these epithelial transitions are phenotypic, the propensity to transition (plasticity) among carcinoma cells may be determined by genotype. The majority of plastic cells may inhabit transitional intermediate states with properties of both epithelium and mesenchyme, and that these transitional cells may be particularly malignant. Such cells may be detected in: (1) tumors where the cancer cells have mixed histology, which indeed have been observed and have been classified as highly aggressive (e.g., clonal sarcomatous carcinomas of epithelial origin, which exhibit an extremely aggressive behavior, such as sarcomatoid renal cell carcinoma and carcinosarcoma of the prostate); and (2) cancer cells co-expressing epithelial and mesenchymal markers, as described herein.

The disclosure, as illustrated by the non-limiting embodiments in the Examples, provides for identification of cells that possess an intermediate phenotype—expressing epithelial and mesenchymal isoforms of FGFR2, having epithelial-like morphology and gene expression patterns, while also displaying mesenchymal cell-like migration, tumor formation, and metastases. In embodiments, these cells are identified in patients with advanced cancer, metastatic adenocarcinoma, and metastatic breast and prostate carcinomas. In some embodiments, the cells comprise CTCs. In some embodiments the CTCs co-expresses biomarkers including, for example, EpCAM, cytokeratin, and vimentin, which identify cells as both epithelial- and mesenchymal-like. In some embodiments, these CTCs in intermediate phenotypic states are identified by detecting EMT biomarkers and provide a diagnosis and/or prognosis of the state and/or degree of malignancy of a cancer.

In an aspect the disclosure provides a method for detecting CTCs in a biological sample, the method comprising detecting at least one EMT biomarker in the biological sample. In some embodiments such as illustrated in the Examples, biomarkers of EMT are present on the CTCs of patients with common epithelial malignancies. In some embodiments methods that include detection and identification of alternative splice variants of the FGFR2 gene are used to correlate to metastatic propensity and epithelial phenotypic in a CTC.

Thus, EMT biomarker expression may be used to detect CTCs. EMT biomarker expression, or detection of CTCs, or a combination thereof, may be used to assess cancer prognosis, tumor invasiveness, risk of metastasis, or to stage tumors. As mentioned above, the methods described herein can include any suitable method for evaluating EMT biomarker expression including, but not limited to, detection with antibodies, real time RT-PCR, Northern analysis, magnetic particles (e.g., microparticles or nanoparticles), Western analysis, and any method or system involving flow cytometry. In some embodiments, the methods and EMT biomarkers can be used in a commercially available system such as a system that has been approved by a regulatory agency (e.g., FDA) including, for example, CELLSEARCH® technology (Veridex LLC). Thus, the methods can incorporate standard protocols that are known in the art. For example, embodiments comprising CELLSEARCH® technology can include detecting the presence of an EMT biomarker, and correlated to quantifying the number of circulating tumor cells (CTCs) a biological sample, (e.g., blood collected from women in need of a new treatment regimen for metastatic breast cancer, or men in need of treatment for mCRPC). Typical protocols can include drawing blood sample sizes of about 15 mL that can be collected at any particular time (suitably when the patient starts the new therapy, and then again at three to four week intervals). The number of CTCs can be correlated with disease response or progression as determined by standard radiology studies (e.g., CT scans) performed every nine to 12 weeks.

In an aspect, the disclosure relates to a method for detecting a circulating tumor cell (CTC) in a biological sample, wherein the method comprises detecting at least one EMT biomarker in the biological sample. As noted above, a biological sample can be from any tissue or fluid from an organism. In some embodiments the biological sample is from a bodily fluid or tissue that is part of, or associated with, the lymphatic system or the circulatory system of the organism. In some embodiments the biological sample is a blood sample.

The EMT and cellular plasticity biomarkers used in the methods described herein are associated with circulating tumor cells (CTCs). Accordingly, in various embodiments the methods include detecting the presence of one or more EMT biomarker and correlating that detection with the presence of a CTC, optionally quantifying the number of CTCs in the sample. As discussed herein, EMT biomarkers can include any detectable biomolecule that is associated with a transitional cell that exhibits characteristics (e.g., phenotype, or surface antigen or gene expression profiles, etc.) of plasticity, stem-like properties, invasiveness, and/or chemo-resistance of a cell. In some non-limiting embodiments, the EMT biomarker includes any of vimentin, N-cadherin, O-cadherin, E-cadherin, FGFR2 splice variant isoforms (such as, for example FGFR2 that includes or excludes either exon IIIc or exon IIIb), or CD133, or any combination of two or more thereof In some embodiments, the EMT biomarker can include one or more of vimentin (polypeptide SEQ ID NO: 14 encoded by polynucleotide SEQ ID NO: 13), N-cadherin (polypeptide SEQ ID NO: 2 encoded by polynucleotide SEQ ID NO: 1; polypeptide SEQ ID NO: 16 encoded by polynucleotide SEQ ID NO: 15), O-cadherin (polypeptide SEQ ID NO: 4 encoded by polynucleotide SEQ ID NO: 3; polypeptide SEQ ID NO: 18 encoded by polynucleotide SEQ ID NO: 17), E-cadherin (polypeptide SEQ ID NO: 12 encoded by polynucleotide SEQ ID NO: 11; polypeptide SEQ ID NO: 24 encoded by polynucleotide SEQ ID NO: 23), FGFR2 (polypeptide SEQ ID NO: 8 encoded by polynucleotide SEQ ID NO: 7; polypeptide SEQ ID NO: 10 encoded by polynucleotide SEQ ID NO: 9; polypeptide SEQ ID NO: 22 encoded by polynucleotide SEQ ID NO: 21), and CD133 (polypeptide SEQ ID NO: 6 encoded by polynucleotide SEQ ID NO: 5; polypeptide SEQ ID NO: 20 encoded by polynucleotide SEQ ID NO: 19). In some embodiments, the EMT biomarker can include one or more of N-cadherin, for example human N-cadherin (for example SEQ ID NO: 16, CCDS ID No: CCDS11891.1); O-cadherin, for example human O-cadherin (for example SEQ ID NO: 18, CCDS ID No: CCDS10803.0); E-cadherin, for example human E-cadherin (for example SEQ ID NO: 24, CCDS ID No:

CCDS10869.1); CD133, for example human CD133 (for example SEQ ID NO: 20, CCDS ID No: CCDS47029.1); FGFR2, for example human FGFR2 (for example SEQ ID NO: 22, CCDS ID No: CCDS31298.1); and vimentin, for example human vimentin (for example SEQ ID NO: 14, Accession No. BC000163). It will be understood by one of skill in the art that when reference is made to polynucleotides that encode polypeptides in the above embodiments as well as embodiments throughout, the polynucleotide can be disclosed as either an RNA (e.g., mRNA) or a DNA (e.g., cDNA).

The EMT biomarkers can be associated with any organism (ortholog) and in certain embodiments are EMT biomarkers associated with a human. Any portion or the entirety of an EMT biomarker can be used for detecting in the methods described herein such as, for example, an epitope of an EMT biomarker protein that binds to an antibody, or a nucleic acid sequence of an EMT biomarker an expressed or transcribed mRNA molecule that is complementary to a reporter nucleic acid probe or primer. In some embodiments, the methods provide for detecting expression of at least two EMT biomarkers. In certain embodiments, expression of vimentin and E-cadherin are detected. In certain embodiments, expression of N-cadherin and O-cadherin are detected. This measure may be used alone or in combination with another method to detect CTCs. In certain embodiments, the methods described herein may be used as a supplemental method in conjunction with CELLSEARCH® Circulating Tumor Cell Test (noted above). Thus, embodiments provide for a method as part of a dual or complementary detection system that can be used to detect and optionally quantify CTCs in a sample (e.g., comprising the detection of EpCAM and at least one EMT biomarker). The expression of at least one EMT biomarker may be used to isolate CTCs. The expression of at least one EMT biomarker may be used to count or provide a relative number or amount of CTCs, using any known method for correlating detection of a biomarker to a cell, such as a CTC. CTCs may be detected at the time of, prior to, or after metastasis.

Cancers may include, but are not limited to, breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers. Thus, the disclosure is generally applicable to any type of cancer in which expression of an EMT biomarker occurs. In certain embodiments, the cancer is a solid tumor malignancy. In certain embodiments, the cancer is breast, colon, or prostate cancer.

Expression of at least one EMT biomarker may be detected using any suitable method known in the art, including but not limited to, binding with antibodies or fragment thereof, antibodies tethered to or associated with an imaging agent, expression reporter plasmids, flow cytometry, and any suitable array scanner technology. The antibody or fragment thereof may suitably recognize a particular intracellular protein, protein isoform, or protein configuration.

As used herein, an "imaging agent" or "reporter molecule" is any entity which enhances visualization or detection of the cell to which it is delivered. Any type of detectable reporter molecule/imaging agent can be used in the methods disclosed herein for the detection of one or more EMT biomarker. Such detectable molecules are known in the art and include, for example, magnetic beads, fluorophores, radionuclides, nuclear stains (e.g., DAPI). For example, an imaging agent can include a compound that comprises an unstable isotope (i.e., a radionuclide) or a fluorescent moiety, such as Cy-5, Alexa 647, Alexa 555, Alexa 488, fluorescein, rhodamine, and the like. Suitable radionuclides include both alpha- and beta-emitters. In some embodiments, the targeting vehicle is labeled. In other embodiments, suitable radioactive moieties include labeled polynucleotides and polypeptides which can be coupled to the targeting vehicle. In some embodiments, the imaging agent comprises a radionuclide such as, for example, a radionuclide that emits low-energy electrons (e.g., those that emit photons with energies as low as 20 keV). Such nuclides can irradiate the cell to which they are delivered without irradiating surrounding cells or tissues. Non-limiting examples of radionuclides that are can be delivered to cells include $^{137}$Cs, $^{103}$Pd, $^{111}$In, $^{125}$I, $^{211}$At, $^{213}$Bi, and $^{213}$Bi, among others known in the art. Further imaging agents suitable for delivery to a cell in accordance with some embodiments include paramagnetic species for use in MRI imaging, echogenic entities for use in ultrasound imaging, fluorescent entities for use in fluorescence imaging (including quantum dots), and light-active entities for use in optical imaging. A suitable species for MRI imaging is a gadolinium complex of diethylenetriamine pentacetic acid (DTPA). For positron emission tomography (PET), $^{18}$F or $^{11}$C may be delivered. Other non-limiting examples of reporter molecules are discussed throughout the disclosure.

In an aspect, the disclosure provides a kit for detecting CTCs in a sample. In embodiments, the kit comprises an antibody to at least one EMT biomarker. The antibody in the kit can be connected to or associated with an imaging agent. In embodiments, the kit can comprise an antibody to at least one EMT biomarker, wherein the antibody is associated a magnetic bead. The magnetic bead may be used for ferromagnetic separation and enrichment of CTCs.

Aspects also relate to methods of predicting responsiveness of a subject to a cancer drug. The methods may comprise determining the level of expression of at least one EMT biomarker in a sample from the subject. The level of expression of at least one EMT biomarker may be used to obtain a gene expression pattern in CTCs for the subject. The methods may further comprise predicting responsiveness of the subject to the cancer drug based on the gene expression pattern obtained. Genome variation in CTCs from the subject may also be determined.

Also provided are methods of providing a cancer prognosis to a subject. The methods may comprise determining the level of expression of at least one EMT biomarker in a sample from the subject. The level of expression of at least one EMT biomarker may be used to determine the number of CTCs in the sample. The CTCs may be captured using at least one EMT biomarker. The level of expression of at least one EMT biomarker may be used to determine a gene expression pattern in the CTCs for the subject. A prognosis may be provided to the subject based on the gene expression pattern obtained.

Also provided are methods for following the progress of cancer in a subject. The methods may comprise determining the level of expression of at least one EMT biomarker in samples from the subject at a first and a second time, and comparing the first and second levels of expression. The level of expression of at least one EMT biomarker in the sample may be determined over time, such as following initiation of a new cancer therapy. The level of expression of at least one EMT biomarker in the sample may be used to determine the number or amount of CTCs. An increase between the first and second levels may indicate progression of the cancer. A decrease between the first and second levels may indicate remission or response of the cancer to the therapy. No difference between the first and second levels may indicate arrest or stability in the progression of the cancer.

Also provided are methods of screening for cancer in a subject. The methods may comprise determining the level of expression of at least one EMT biomarker in a sample from the subject. The level of expression of at least one EMT biomarker may be used to determine the amount or number of CTCs in the subject. The level of expression of at least one EMT biomarker may be compared to a normal or control sample. An increased level of at least one EMT biomarker may indicate presence of cancer in the subject.

Also provided are methods of arresting cell growth or inducing cell death of a cancer cell expressing an EMT biomarker. The methods include contacting the cancer cell with a conjugate capable of mediating intracellular delivery of an agent, such as the antibodies to EMT markers described herein. The agent is capable of arresting or attenuating the growth of the cell or inducing cell death through any mechanism after agent internalization. The cancer cell may be contacted with the conjugate in vitro, in vivo, or ex vivo. These methods may be useful in treating cancer by directly targeting cancer cells expressing an EMT biomarker for delivery of agents capable of decreasing or arresting cell growth or inducing cell death.

The disclosure also provides for targeted therapeutic methods and molecules that comprise an anti-cancer agent linked to a binding agent that targets at least one EMT as described herein. In some embodiments the link between the anti-cancer agent and the binding agent is a covalent bond. In some embodiments the link is formed by strong electrostatic interactions (hydrogen bonds, hydrophilic/hydrophobic interaction, or oppositely charged moieties, and the like). Any anti-cancer agent can be used in such molecules and therapeutic methods, and can be selected by one of skill in the art based on the type of cancer to be treated, the progress/stage of the cancer, potential adverse drug interactions, dosage requirements, administration schedule, and the like.

Method of Isolating, Capturing, or Enriching Circulating Tumor Cells

With the importance of EP in metastasis, the disclosure identifies CTCs that have lost their epithelial phenotype in patients, such as patients with advanced prostate cancer, using a mesenchymal-based capture method. Such a method may complement or replace existing epithelial-based approaches by capturing cells that have reduced or absent EpCAM expression.

The present disclosure is directed to methods of isolating, capturing or enriching CTCs using any EMT biomarker, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby isolating, capturing, or enriching the circulating tumor cell. The EMT biomarker may include OB-cadherin, N-cadherin, vimentin, E-cadherin, FGFR2 splice variant isoforms, or CD133.

a) OB-cadherin

OB-cadherin, also known as cadherin-11 and O-cadherin, is encoded by the CDH11 gene and was first identified in mouse osteoblasts. OB-cadherin is a homophilic cell adhesion molecule that mediates osteoblast adhesion during bone development. Aberrant OB-cadherin expression has been recognized in breast, gastric, and prostate cancers. OB-cadherin may be involved in prostate cancer metastasis. OB-cadherin expression was shown in CTCs (see FIG. 1).

In human prostate cancer, examination by immunohistochemistry showed increased expression of OB-cadherin in bone metastases compared with the primary tumor. Although the exact mechanism of how OB-cadherin expression facilitates bone metastasis is unclear, OB-cadherin is known to mediate adhesion between PC cells and osteoblasts. Preclinically, in PC-3 cells, when OB-cadherin is silenced by shRNA and the silenced cells are injected into mice, fewer bone metastases develop, while metastases in other organs was unaffected. In addition, induction of OB-cadherin expression has been linked to EMT/EP biology in other model systems. Furthermore, androgen depletion leads to OB-cadherin upregulation, suggesting a role for OB-cadherin in castration-resistant disease progression. Finally, given that lethal metastatic prostate cancer invariably spreads to bone in the vast majority of men, OB-cadherin positive CTCs may be detectable in the blood of men with metastatic CRPC.

Antibodies directed against OB-cadherin were attached to iron particles to form a novel ferrofluid that may replace or complement EpCAM ferrofluid in the FDA-approved CELLSEARCH® technology. After OB-cadherin expressing cells are enriched from whole blood immunomagnetically, additional characterization steps follow to ensure that the captured cells are the cells of interest, such as measuring levels of an EMT-independent characterization protein, such as β-catenin. The antibody may bind to the extracellular domain of OB-cadherin.

b) N-cadherin

N-cadherin, also known as neural cadherin (NCAD) and cadherin-2 (CDH2) is encoded by the CDH2 gene. N-Cadherin is commonly found in cancer cells and provides a mechanism for transendothelial migration. When a cancer cell adheres to the endothelial cells of a blood vessel, it up-regulates the src kinase pathway, which phosphorylates beta-catenins attached to both N-cadherin and E-cadherins. This causes the intercellular connection between two adjacent endothelial cells to fail and allows the cancer cell to slip through. The antibody may bind to the extracellular domain of N-cadherin.

Methods of Confirming Circulating Tumor Cells

Given that CTCs are extraordinarily rare relative to other circulating cells, the isolation of CTCs involves the identification and exclusion of cells expressing the pan-leukocyte marker CD45. Circulating CD45 negative cells are not necessarily tumor-derived, however, but instead may represent normal blood vessel or stromal cells, circulating mesenchymal cells or stem cells, or other host cells that exist in rare quantities in the circulation. Circulating endothelial cells result from blood vessel wall turnover, and bone marrow-derived endothelial progenitor cells may circulate in the setting of neovascularization of ischemic tissue and tumor formation. These cells are all CD45 negative and CD31 positive. Also CD45 negative but CD31 negative, mesenchymal stromal cells (MSCs) are a more diverse group of cells that may be bone marrow-, peripheral blood-, or fat-derived. MSCs are multipotent cells that may differentiate into a variety of stromal cell types, circulate in inflammatory disorders, and are under active investigation for use in regenerative medicine and other conditions. The significance of circulating MSCs in cancer remains unclear. Thus, any CTC detection method involves distinguishing tumor cells from a range of other rare non-tumor cells in the circulation that may express non-epithelial biomarkers. Confirmation of CTCs may include detecting β-catenin, CD31, CD45, cytokeratin, and/or PSA, staining with DAPI, and/or detecting a prostate cancer-specific genomic event. For example, a CTC may be confirmed if DAPI staining is positive, β-catenin expression is positive, CD45 expression is negative, and CD31 expression is negative. The detection of β-catenin, CD31, CD45, cytokeratin, and/or PSA may be performed using antibodies against β-catenin, CD31, CD45, cytokeratin, and/or PSA, wherein the antibodies are labeled.

a) β-catenin

β-catenin, encoded by the CTNNB1 gene, has multiple functions in cancer cells, including cadherin-mediated cell adhesion and involvement in the Wnt signaling pathway. When Wnt ligands are absent, β-catenin is phosphorylated and degraded. When Wnt ligands are present, β-catenin moves to the nucleus and activates target genes linked to EMT/invasion, proliferation, and survival in multiple cancers. In prostate cancer specifically, β-catenin may act as cofactor with the androgen receptor and increased expression and change in localization has been observed in advanced disease. β-catenin expression may be a constant finding regardless of the epithelial or mesenchymal phenotypic nature of a CTC. Using β-catenin expression to identify CTC does not have the epithelial bias associated with using cytokeratin. An antibody that binds to β-catenin may be used to detect β-catenin.

b) CD31

Cluster of differentiation 31 (CD31), also known as platelet endothelial cell adhesion molecule (PECAM-1), is a encoded by the PECAM1 gene and plays a role in removing aged neutrophils from the body. CD31 is found on the surface of platelets, monocytes, neutrophils, and some types of T-cells, and makes up a large portion of endothelial cell intercellular junctions. CD31 is normally found on endothelial cells and used in immunohistochemistry to demonstrate the presence of endothelial cells in histological tissue sections. An antibody that binds to CD31 may be used to detect CD31.

c) CD45

Cluster of differentiation 45 (CD45), also known as protein tyrosine phosphatase, receptor type, C and leukocyte common antigen, is encoded by the PTPRC gene. CD45 is used to identify leukocytes. An antibody that binds to CD45 may be used to detect CD45.

d) Cytokeratin

Cytokeratins are keratin-containing intermediate filaments found in the intracytoplasmic cytoskeleton of epithelial tissue. Cytokeratin-expressing cancer cells lose their cytokeratin expression after undergoing epithelial-mesenchymal transition, with up to 20% of cells having no detectable cytokeratin. A protein other than cytokeratin may identify a pure mesenchymal CTC.

e) PSA

Prostate-specific antigen (PSA), also known as gamma-seminoprotein or kallikrein-3 (KLK3), is a glycoprotein enzyme encoded in humans by the KLK3 gene. PSA is a member of the kallikrein-related peptidase family and is secreted by the epithelial cells of the prostate gland. PSA is present in small quantities in the serum of men with healthy prostates, but is often elevated in the presence of prostate cancer or other prostate disorders.

f) DAPI

DAPI, also known as 4',6-diamidino-2-phenylindole, is a fluorescent stain that binds strongly to A-T rich regions in DNA. It is used extensively in fluorescence microscopy. DAPI can pass through an intact cell membrane therefore it can be used to stain both live and fixed cells.

g) Prostate Cancer-Specific Genomic Event

A CTC may be confirmed by detecting the presence or absence of at least one prostate cancer-specific genomic event. The at least one prostate cancer-specific genomic event may be androgen receptor amplification, phosphatase and tensin homolog (PTEN) loss, gene fusion of transmembrane protease, serine 2 (TMPRSS2) gene and ETS related (ERG) gene, and combinations thereof. For example, the detection of the presence of androgen receptor amplification, phosphatase and tensin homolog (PTEN) loss, gene fusion of transmembrane protease, serine 2 (TMPRSS2) gene and ETS related (ERG) gene may indicate and/or confirm that the CTC is a prostate cancer cell. The detection of a prostate cancer-specific genomic event may be performed using fluorescent in situ hybridization.

Method of Detecting or Identifying Circulating Tumor Cells

The present disclosure is directed to methods of detecting or identifying CTCs using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby detecting or identifying the circulating tumor cell.

Methods for Isolating or Capturing an Intact Cell From a Patient

The present disclosure is directed to methods of isolating or capturing an intact cell from a patient, wherein the intact cell is β-catenin positive, DAPI positive, and CD45 negative, using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby isolating or capturing the intact cell. The intact cell may be a mesenchymal phenotypic cell, such as mesenchymal CTC.

Method of Detecting Cancer in a Subject

The present disclosure is directed to methods of detecting cancer in a subject using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; comparing the level of circulating tumor cell to a reference level of circulating tumor cell; and detecting cancer in the subject if the level of circulating tumor cell is higher than the reference level of circulating tumor cell, cancer is detected in the subject. The cancer may be at least one cancer, as described above. The method may further include administering a therapy against cancer to the subject identified as having cancer.

Method of Monitoring Progression of Cancer in a Subject Undergoing Therapeutic Treatment The present disclosure is directed to methods of monitoring progression of cancer in a subject undergoing therapeutic treatment using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; and correlating the level of circulating tumor cell with the progression of cancer in the subject, wherein if the level of the circulating tumor cell is higher as compared to the level of the circulating tumor cell in an earlier biological sample from the subject, the subject is identified as having progression of cancer. The method may further include administering a therapy against cancer to the subject identified as having cancer.

Method of Determining a Cancer Prognosis in a Subject

The present disclosure is directed to methods of determining a cancer prognosis in a subject using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; comparing the level of circulating tumor cell to a reference level of circulating tumor cell; and determining the cancer prognosis in the subject, wherein if the level of circulating tumor cell is higher than the reference level of circulating tumor cell, the subject is identified as having cancer. The method may further include administering a therapy against cancer to the subject identified as having cancer.

Method of Predicting Responsiveness of a Subject Having Cancer to a Course of Treatment The present disclosure is directed to methods of predicting responsiveness of a subject having cancer to a course of treatment using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; and comparing the level of circulating tumor cell to a reference level of circulating tumor cell.

Treatment

The subject identified in the methods described above as having a level of circulating tumor cell higher than or equal to a reference level is identified as a patient having cancer. The subject is then treated for the cancer.

a) Prostate Cancer

The subject identified in the methods described above having levels of circulating tumor cell greater than or equal to a reference level is identified as a patient having prostate cancer. The subject is then treated for the prostate cancer. Treatments may include watchful waiting or active surveillance, surgery, cryosurgery, high-intensity focused ultrasound, radiation, hormone therapy, chemotherapy, and targeted therapy. Examples of surgery include pelvic lymphadenectomy, radical prostatectomy (retropubic prostatectomy and perineal prostatectomy), transurethral resection of the prostate, and laparoscopic prostatectomy. Examples of radiation therapy include high-energy x-rays (external and internal radiation therapy), proton beam radiation, and intensity-modulated radiation therapy. Examples of hormone therapy include luteinizing hormone-releasing hormone agonists, such as leuprolide (Lupron, Eligard), goserelin, triptorelin (Trelstar), histrelin (Vantas), and buserelin, antiandrogens, such as flutamide, bicalutamide (Casodex), and nilutamide (Nilandron), ketoconazole, orchiectomy, estrogen, and aminoglutethimide. Examples of chemotherapeutic drugs include abiraterone acetate (Zytiga), cabazitaxel, degarelix, docetaxel, enzalutamide (Xtandi), cabazitaxel (Jevtana), leuprolide acetate (Lupron, Lupron Depot, Lupron Depot-3 Month, Lupron Depot-4 Month, Lupron Depot-Ped, Viadur), prednisone, sipuleucel-T (Provenge), estramustine (Emcyt), mitoxantrone (Novantrone), vinorelbine (Navelbine), paclitaxel (Taxol), cyclophosphamide (Cytoxan), etoposide (VP-16), G-1 (a GPR30 agonist/stimulator), and docetaxel (Taxotere).

b) Breast cancer

The subject identified in the methods described above having levels of circulating tumor cell greater than or equal to a reference level is identified as a patient having breast cancer. The subject is then treated for the breast cancer. Treatment may include surgery, radiation therapy, bone-directed therapy, chemotherapy, hormone therapy, and targeted therapy. Examples of surgery include lumpectomy, quadrantectomy, mastectomy, such as simple mastectomy, skin-sparing mastectomy, modified radical mastectomy, prophylactic mastectomy, and radical mastectomy, prophylactic ovary removal, cryotherapy, and lymph node surgery, such as axillary lymph node dissection and sentinel lymph node biopsy. Examples of radiation therapy include external beam radiation, such as accelerated breast irradiation and 3D-conformal radiotherapy, and brachytherapy (internal radiation), such as interstitial brachytherapy, intracavitary brachytherapy, and intraoperative radiation. Examples of bone-directed therapy include bisphosphonates and denosumab. Examples of chemotherapy include anthracyclines, such as doxorubicin (Adriamycin, Doxil), epirubicin (Ellence), and daunorubicin (Cerubidine, DaunoXome), capecitabine (Xeloda), carboplatin (Paraplatin), cisplatin, cyclophosphamide (Cytoxan), eribulin (Halaven), fluorouracil (also called 5-fluorouracil or 5-FU; Adrucil), gemcitabine (Gemzar), ixabepilone (Ixempra), methotrexate (Amethopterin, Mexate, Folex), mitoxantrone (Novantrone), mutamycin (Mitomycin), taxanes, such as paclitaxel (Taxol, Abraxane), and docetaxel (Taxotere), thiotepa (Thioplex), vincristine (Oncovin, Vincasar PES, Vincrex), and vinorelbine (Navelbine). Examples of hormone therapy include aromatase inhibitors, such as anastrozole (Arimidex), exemestane (Aromasin), and letrozole (Femara), selective estrogen receptor modulators (SERMs), such as tamoxifen (Nolvadex), raloxifene (Evista), and toremifene (Fareston), and estrogen-receptor downregulators, such as fulvestrant (Faslodex). Examples of targeted therapy include trastuzumab (Herceptin), lapatinib (Tykerb), bevacizumab (Avastin), pertuzumab (Perjeta), and everolimus (Afinitor).

Kits

Provided herein is a kit, which may be used for isolating, capturing or enriching CTCs from a sample. The kit comprises at least one component for isolating, capturing or enriching CTCs from a sample and instructions for isolating, capturing or enriching CTCs from a sample. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one antibody that specifically binds to at least one EMT biomarker. The antibody may be an EMT biomarker capture antibody. The antibody may include an antibody against OB-cadherin or N-cadherin. The antibody may be associated with a solid support. The solid support may be a magnetic bead. The magnetic bead may be used for ferromagnetic separation and enrichment of CTCs.

The kit may also comprise at least one staining reagent. The at least one staining reagent may comprise an antibody which is detectably labeled. The antibody may include an antibody against a biomarker which is used to confirm the CTC. The biomarker may be β-catenin, CD45 or CD31. The at least one staining reagent may include of phycoerytherin-labeled anti-β-catenin antibody and an allophycocyanin-labeled anti-CD45 antibody.

The kit may also comprise a calibrator or control and/or at least one container for conducting the isolation, capturing, or enrichment of CTCs. The kit may comprise all components, i.e., reagents, standards, buffers, diluents, etc., which are necessary to perform the isolation, capturing, or enrichment of CTCs.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

EXAMPLES

Example 1

Materials and Methods

Plasmids and cell culture. The minigene used (pRIIIcI$^2$) was previously described (S. Oltean et al., *Proc Natl Acad Sci USA* 2006, 103, 14116, incorporated herein by reference in its entirety). All cell lines were cultured in low glucose DMEM (Invitrogen) with 10% FBS and 15 IJg/mL blasticidin. Single cell progenies were isolated from a population of AT3 cells stably transfected with pRIIIcI$^2$ minigene by limiting dilution to produce a concentration of 1 cell/10 wells and plated on 96-well plates. Cells were counted using a hemocytometer to obtain an initial concentration of 1×10$^5$ cells/mL. Through a series of progressive dilutions a final concentration of 1 cell/mL was obtained and 100 IJl were pipetted in each well of three 96-well plates. All wells were monitored through bright field microscopy, those appearing to contain more than one cell were excluded, and those containing single cells were further cultured into 25 mL flasks. 16 of an expected 27 clones were obtained using this procedure in a first round.

To measure cell population growth rate in vitro, cells were plated at 50,000/well in 6-well dishes. Viable cells were counted using Trypan Blue staining at 24, 48, 72, and 96 h.

Animals and tumor cell implantation. Cells were trypsinized, washed, and resuspended in PBS at a final concentration of $3\times10^5$ cells/mL, and kept on ice for less than 30 minutes before implantation. Cells ($3\times10^5$) were injected subcutis in both flanks of Copenhagen 2331 rats (Harlan Labs, Indianapolis, Ind.; 75-90 g, 2 months of age). Animals were continuously monitored for tumor growth. All animal procedures were approved by the Duke University Institutional and Animal Care and Use committee and followed NIH guidelines. Sacrifice curves were compared using a Mantel-Haenszel logrank test. Tumor volume was compared using an unpaired t test. Prism 4.0 c for the Macintosh (Graphpad, La Jolla, Calif.) was used for statistical analyses.

Histological sections and analysis. Excised tumors and lungs were washed in PBS at room temperature. Depending on the size of the lungs, they were frozen either together or separately. The tumor sections and the lungs were placed in cryomolds, embedded in optimal-cutting-temperature tissue sectioning medium (Sakura Finetek, Torrance, Calif.), snap-frozen in liquid nitrogen, and stored at 80° C. Slides for fluorescence imaging were prepared as follows: the tissue was incubated for 2-3 h at −20° C. to equilibrate the temperature and then sectioned with a microtome. The sections (15 μm) were placed on glass slides, fixed in 4% (wt/vol) paraformaldehyde for 30 min at room temperature, and rinsed in PBS at room temperature. The slides were mounted with gel/mount media (Biomeda, Foster City, Calif.). The sections were analyzed by using an Olympus (Melville, N.Y.) IX 71 epifluorescence microscope, and images were acquired by using an Olympus DP70 digital camera. Image processing was done with DP Controller software (Olympus). For hematoxylin-eosin staining after fluorescence imaging, the slides were incubated in warm water for 15-20 minutes for the cover slip to come off, slides were dried, and staining was performed according to standard procedure.

RNA extraction from tumor sections. Sections were fixed in 4% (wt/vol) paraformaldehyde for 5 minutes, rinsed in PBS, and imaged. DsRED+ and DsRED− regions of the sections were marked on the slide. The slide was immersed in warm water for 5 minutes to remove the coverslip and the DsRED+ and DsRED− regions scraped off. RNA isolation was further performed as described before (N. Masuda, T. Ohnishi, S. Kawamoto, M. Monden, K. Okubo, Nucleic Acids Res 1999, 27, 4436, incorporated herein by reference in its entirety). Briefly, samples were treated with proteinase K in digestion buffer containing SDS, and further isolation of RNA was performed using the RNeasy kit (QIAGEN, Valencia, Calif.).

Immunoblots. Cells were collected from confluent 25 cm² tissues flasks by scraping, washed in PBS, and lysed in sample buffer. Whole cell lysates were serially diluted in sample buffer, fractionated via 7.5% SDS-PAGE, and transferred to PVDF. Membranes were cut in half The bottom half was probed with anti-β-actin at 1:1000 or 1:5000 (Santa Cruz Biotechnology, CA, 47778) as an internal loading control, while the top half was probed with anti-CD 133 (Santa Cruz Biotechnology, CA, 30219) at 1:200 or anti-CD44 (Santa Cruz Biotechnology, CA, 7946) at 1:200.

Gene expression analysis. Triplicate cultures of AT3-M and AT3-T cells were grown to ~60% confluency. Total RNA was isolated using the RNeasy kit (Qiagen, Valencia, Calif.), and triplicate samples were submitted to the Duke Microarray Facility. Gene expression analysis was performed using the R027K rat spotted arrays 3.0 (Operon, Huntsville, Ala.). Bioinformatical analysis of expression differences between AT3-M and AT3-T cells was done using the GeneSpring GX software version 7.3.1 (Agilent Technologies, Durham, N.C.). The data files (representing signals for 26,986 gene probes in all six data points, three for AT3-M and three for AT3-T) were normalized using the feature: per Spot and per Chip—intensity dependent (lowess) normalization. The resulting gene list was used to determine the significantly differentially expressed genes between AT3-M and AT3-T using the "Filtering on Volcano plot" feature with the following characteristics: (1) Test type: Parametric test, did not assume variances equal; (2) Multiple testing correction: None; (3) Fold Difference: Twofold or greater and a P-value cutoff of 0.05.

Analysis of human circulating tumor cells. Patients eligible for the CTC biomarker protocols included (1) men with progressive CRPC, with metastatic progression by PSA (two consecutive rises over nadir separated by >1 week) or radiologic criteria (RECIST or new bone scan lesions), a PSA ≥5, age ≥18 years; or (2) women with mBC with disease progression or with initiation of a new systemic therapy, who were >18 years of age, and who were at least 7 days from treatment with an anthracycline-containing regimen. Blood (15 mL) was collected from patients and processed within 48 hours at the Duke University CTC lab using the Cell Search System (Veridex, Raritan, N.J.). Veridex profile kits were used, which isolate EpCAM positive cells without additional staining. The isolated cells were either processed immediately or stored overnight in 4% paraformaldehyde and processed the next day. Immunostaining was done on teflon coated slides. Briefly, cells were pipetted into the wells of the slides and left to settle for ~30 minutes followed by standard immunostaining procedures with careful aspiration to minimize cell loss. An initial ferromagnetic wash using a benchtop magnet was performed to further isolate CTCs, with resuspension of the cell pellet after magnet release 100 uL PBS. Following 4% PFA fixation and permeabilization with PBT (PBS with 2% Triton) and blocking with 10% goat serum for 30 minutes, triple immunostaining was performed using CD45 antibody (AbCam #33533-50) labeled with Alexa 647, cytokeratin (AbD Serotec #MCA 1907HT) labeled with Alexa 555, and Vimentin (BD Biosciences, San Jose, Calif. #550513) labeled with Alexa 488. Nuclear staining with 4',6-diamidino-2phenylindole (DAPI) was then performed. A mesenchymal CTC (an event) was defined as an intact cell by microscopic examination, containing an intact nucleus and expressing cytokeratin but lacking CD45 staining, using appropriate controls (see Table 1 for antibodies and controls). Human peripheral blood mononuclear cells (PBMCs), obtained by Ficoll purification of buffy coats from normal donors, were kindly provided by Micah Luftig (Duke University, Durham N.C.) and used as control cells for CD45 expression. Linear regression analysis was performed to compare CTC count (standard Cellsearch method) against the proportion of CTCs that co-express vimentin. Goodness of fit was tested by analysis of variance.

TABLE 1

EMT/Stemness Antigens to be assessed in CTCs.

| Antigen | Product | Positive Control | Negative Control | Leukocyte Expression | Dilution |
|---|---|---|---|---|---|
| Vimentin | BD Biosciences, mouse monoclonal IgG1 | PBMCs, PC-3, DU145 | T47D, LnCAP | Yes | 2:225 |

TABLE 1-continued

EMT/Stemness Antigens to be assessed in CTCs.

| Antigen | Product | Positive Control | Negative Control | Leukocyte Expression | Dilution |
|---|---|---|---|---|---|
| N-cadherin | DAKO, mouse monoclonal IgG1, 6G11 | Sarcoma, rat brain, PC-3 | DU145, T47D, mock | No | 4:225 |
| Cytokeratin (pan) | AbD Serotec, mouse monoclonal IgG1, MCAI907HT, clone AE1/AE3 | T47D, DU145 | PC-3, PBMCs | No | 2:45 |
| CD45 | Invitrogen, mouse IgG1, HI30, MHCD4500 | PBMC | PC-3, DU145 | Yes | 1:45 |
| CD133 | Santa Cruz mouse monoclonal IgG, sc-130127 | CaCo-2 colon cancer cells | Mock | Variable | 4:225 |

The slides were mounted with gel/mount media (Biomeda, Foster City, Calif.). The slides were analyzed with an Olympus (Melville, N.Y.) IX 71 epifluorescence microscope, and images were acquired using an Olympus DP70 digital camera. Image processing was done with DP controller software (Olympus). All fields were analysed, with each cytokeratin positive nucleated cell that was CD45 negative being counted as a CTC. Positive control cells for each antibody included PC-3 cells for vimentin, peripheral blood mononuclear cells (PBMCs) for CD45, and T47D breast cancer cell lines for cytokeratin. A similar volume of reaction mix without antibody was used for negative controls.

Media exchange experiments. The cells of AT3-T or AT3-M clones were plated at a concentration of 150,000 cells/2 mL of media in 6-well plates and allowed to incubate for 24 h. The conditioned media was then filtered using a 0.22 µm filter, and then immediately allowed to incubate with cells of the other clone, which was plated at the same concentration and had its media aspirated and cells washed with 2 mL of PBS. All cells with media replaced were incubated for 72 h, and phase and epifluorescent microscopy was used to monitor cell phenotypes 24, 48, and 72 h after treatment. Control plates, in which media was conditioned, cells washed with PBS and media added back to the same cells, were also used.

Scratch-wound assay. Cells were plated and left to grow to nearly 100% confluency in 6-well dishes. A wound was simulated by scratching the cells with a sterile 200 IJI pipette tip. The wells were washed twice with PBS and fresh media added. Pictures were taken in the same marked spot at 0, 24, and 48 h. Percent migration was calculated as (width at 0 h−width at 24 or 48 h) 1 width at 0 h×100. Relative migration was compared using two-way analysis of variance via Prism 4.0 c for the Macintosh (Graphpad, La Jolla, Calif.).

Matrigel assay. Matrigel assay was performed per manufacturer's indications (BD Biosciences). Briefly, after rehydration, $2\times10^5$ cells were plated either in the control or in the matrigel-coated inserts and incubated for 22 h. Following incubation, the non-invading cells from the upper-part of the inserts were removed using cotton-tipped swabs. The cells from the lower part of the membrane were stained with hematoxylin-eosin, membranes were removed, placed on a slide and observed under the microscope.

Immunohistochemical (IHC) analysis of metastases. Under the same informed consent protocol as the analysis of human circulating tumor cells described above, men undergoing CTC collection additionally consented to have a radiologic-guided metastatic biopsy for analysis of biomarker expression by IHC. Samples were obtained through core needle biopsies during light sedation, and immediately formalin-fixed and paraffin embedded. For analysis, slides were deparaffinized, rehydrated, and endogenous peroxidase was inactivated for 30 min. in 0.3% $H_2O_2$ (hydrogen-peroxide) in methanol. Specific antigen retrieval steps were performed for individual antigens. Three markers were evaluated by IHC: vimentin (M7020, Dako, 1:150; antigen retrieval with pepsin treatment at 37° C. for 15 minutes), cytokeratin cocktail (18-0132, Invitrogen, 1:50 and 349205, BD Biosciences 1:50, antigen retrieval with pepsin treatment at 37° C. for 15 minutes), and CD45 (M0701, Dako, 1:200; antigen retrieval with sodium citrate 10 mM, pH 6.0 at 100° C. for 30 minutes). Primary antibody was incubated for 60 minutes at room temperature. Dako Envision horseradish peroxidase secondary antibody was used for 30 minutes at room temperature and the signal was detected with DAB reagent (Vector kit SK 4100). Slides were counter stained with hematoxylin and eosin and assessed by a trained pathologist for expression using appropriate positive (localized prostate tissue microarray sections) and negative controls (mock antibody) for each marker.

Statistical analyses. To determine the significantly differentially expressed genes between AT3-M and AT3-T the GeneSpring GX "Filtering on Volcano plot" feature was used with the following characteristics: (1) Test type: Parametric test, don't assume variances equal; (2) Multiple testing correction: None; (3) Fold Difference: Twofold or greater and a P-value cutoff of 0.05. To compare CTC count (standard CELLSEARCH® method) against the proportion of CTCs that co-express vimentin, N-cadherin, or CD133, linear regression analysis was performed. Goodness of fit was tested by analysis of variance.

Example 2

Isolation of Individual AT3 Clones that Inhabit an Intermediate Phenotypic State The alternative splicing of FGFR2 transcripts, which produces either FGFR2-IIIb or—IIIc variants in epithelial and mesenchymal cells respectively, is exquisitely regulated (FIG. 1A). In FIG. 1A is a schematic representation of the IIIb and IIIc alternatively spliced isoforms of FGFR2. FGFR2 contains an extracellular domain (with three IgG-like domains), a transmembrane domain (TM), and two intracellular tyrosine kinase domains. The IIIb isoform is found in epithelial cells while the IIIc isoform in mesenchymal cells. Exons IIIb and IIIc are regulated coordinately to provide mutually exclusive expression of the two isoforms and transcripts including both exons are destabilized by nonsense-mediated decay. We have previously used FGFR2 alternative splicing reporters, in particular constructs that measure the epithelial-specific silencing of exon IIIc (e.g., pRIIIcI$^2$ in FIG. 1B), to report on the phenotypic state of cells in vitro and in vivo. In FIG. 1B is a schematic of the pRIIIcI$^2$ minigene and the fluorescence read-out. The minigene contains the DsRED open reading frame interrupted by exon IIIc and flanking introns of the FGFR2 gene. In epithelial cells exon IIIc is skipped, DsRED open reading frame is formed and results in fluorescence signal. In mesenchymal cells, exon IIIc is included and the DsRED open reading frame is disrupted, resulting in low or close-to-background fluorescence signal. The pRIIIcI$^2$ splicing reporter, which produces a variant red fluorescent protein (DsRED) when exon IIIc is silenced, revealed MET in primary tumors derived from AT3 cells implanted in the flanks of Copenhagen white rats. While most tumors contained MET foci, each tumor had very few foci and these were not randomly distributed but rather were associated with collagenous stroma. In contrast to the low frequency of MET in primary tumors, a high incidence of MET among lung metastases in these animals was observed, suggesting an unexpected association between the more epithelial phenotype and aggressive behavior. These studies could not ascertain whether the epithelial-like AT3 cells found in the lungs had undergone MET in the primary tumors or during the process of metastasis.

In an attempt to find post-MET cells in vitro, limiting dilution was used to obtain clones from AT3 cells stably transfected with the pRIIIcI$^2$ reporter. A total of 16 clones of a maximum calculated recovery of 27 were obtained, which is ~60% cloning efficiency. Eleven of these sixteen clones expressed RIIIcI$^2$ transcripts (italicized in Table 2), and of these, eight expressed DsRED (Table 2). Some of the clones had an epithelial-like morphology (cells with cobblestone appearance and adherent to each other), while others had a mesenchymal-like morphology (spindle-shaped), as well as clones that displayed a mixed phenotype. It is important to note that given the high cloning efficiency and the high frequency of DsRED+ clones, it is highly unlikely for these epithelial-like clones to come from a very small population within the parental AT3 cells. Rather, the process of sub-cloning induced a phenotypic transition in a significant number of the AT3 cells.

TABLE 2

Properties of AT3 clones.

| AT3 Clones | Cellular morphology[3] | DsRED expression[2] | Detection of exon IIIc skipping among RIIIcI3 transcripts[1] | FGFR2 transcripts detected[3] |
| --- | --- | --- | --- | --- |
| 1 | Epithelial | High | + | IIIc |
| 2 | Epithelial | High | + | IIIc > IIIb |
| 3 | Epithelial | Low | ND | IIIc > IIIb |
| 4 | Epithelial | Low | ND | IIIc |
| 5 | Epithelial | High | + | IIIc > IIIb |
| 6 | Mesenchymal | Low | ND | IIIc |
| 7 | Mixed | Low | ND | IIIc |
| 8 | Mixed | High | + | IIIc |
| 9 | Mixed | Low | ND | IIIc |
| 10 | Mixed | High | + | IIIc |
| 11 | Mesenchymal | Low | − | IIIc |
| 12 | Mesenchymal | Low | − | IIIc |
| 13 | Epithelial | High | −1 | IIIc > IIIb |
| 14 | Epithelial | Low | − | IIIc |
| 15 | Epithelial | High | + | IIIc |
| 16 | Mixed | High | −2 | IIIc |

[1]See FIG. 1C. A "+" indicates detection of RIIIcI$^2$ transcripts missing exon IIIc, a "−" all RIIIcI$^2$ transcripts include exon IIIc, ND means that no RIIIcI$^2$ transcripts were detected.
[2]Determined by epifluorescence microscopy (high is defined as fluorescence above background of naive AT3 cells and low undistinguishable from the same cells).
[3]Discussed further herein and illustrated in FIG. 1C.

All of the clones obtained by limiting dilution were analyzed to determine the splicing status of RIIIcI$^2$ and endogenous FGFR2 transcripts. We could not detect exon IIIc skipping among pRIIIcI$^2$ transcripts or any evidence of exon IIIb inclusion among endogenous FGFR2 transcripts in clones with a mesenchymal-like morphology (FIG. 1C and Table 2). FIG. 1C shows RT-PCR analysis of the reporter (upper panel) and endogenous FGFR2 (lower panel). Primers used for the reporter are designed in the DsRED regions flanking exon IIIc. RT-PCR shows a higher percentage of the skipped product in clone AT3-T compared to clone AT3M. Reactions that did not include RT (-RT) reveal a contaminating product that is out-competed by the presence of a bona fide cDNA template (AT3-M lanes). Since exons IIIb and IIIc differ in size by only 3 nucleotides, analysis of the presence of IIIb or IIIc exons in FGFR2 gene was done by using primers in the flanking exons and specific restriction digestion of the resulting RT-PCR products. Exon IIIb is digested by AvaI (A) and IIIc by HincII (H). There is a higher percentage of exon IIIb in clone AT3-T. The RT-PCR are replicates from three different cultures of the two clones. These clones did not express detectable levels of DsRED (FIG. 1D and Table 2). FIG. 1D shows epifluorescence and phase-contrast pictures of clones AT3-M and AT3-T shows the difference in fluorescence intensity and morphology between the two clones. Epifluorescence pictures were taken at the same exposure. All pictures were acquired at 200× magnification. While the skipping of exon IIIc among pRIIIcI$^2$ transcripts from epithelial-like clones could be expected, the observation that all of these clones both skipped and included exon IIIc was unexpected (FIG. 1C, Table 2 and data not shown). Analysis of endogenous FGFR2 transcripts revealed that four of the clones with epithelial morphology and DsRED expression had clear evidence of coexpression of both IIIb and IIIc isoforms (Table 2, and FIGS. 1C and 1D). As shown in FIG. 1, AT3-T cells expressed epithelial and mesenchymal isoforms of FGFR2. The expression of DsRED in all the cells suggested that each cell in the culture was expressing both isoforms (FIG. 1C).

We followed two clones with epithelial morphology, high DsRED levels and co-expression of FGFR2-IIIb and -IIIc transcripts (clone 2 and clone 5 (clone 5 herein AT3-T)) and noted that the phenotypic characteristics described above were stable for over six months. Equally, we followed clone 11 (clone 11 herein AT3-M) and clone 12 for six months, and noted that the mesenchymal morphology, undetectable DsRED expression and exclusive production of FGFR2-IIIc were also stable. We concluded from these observations that AT3 cells were plastic and were coaxed by sub-cloning to populate intermediate phenotypic states, with properties of epithelial and mesenchymal cells.

Figure 2:
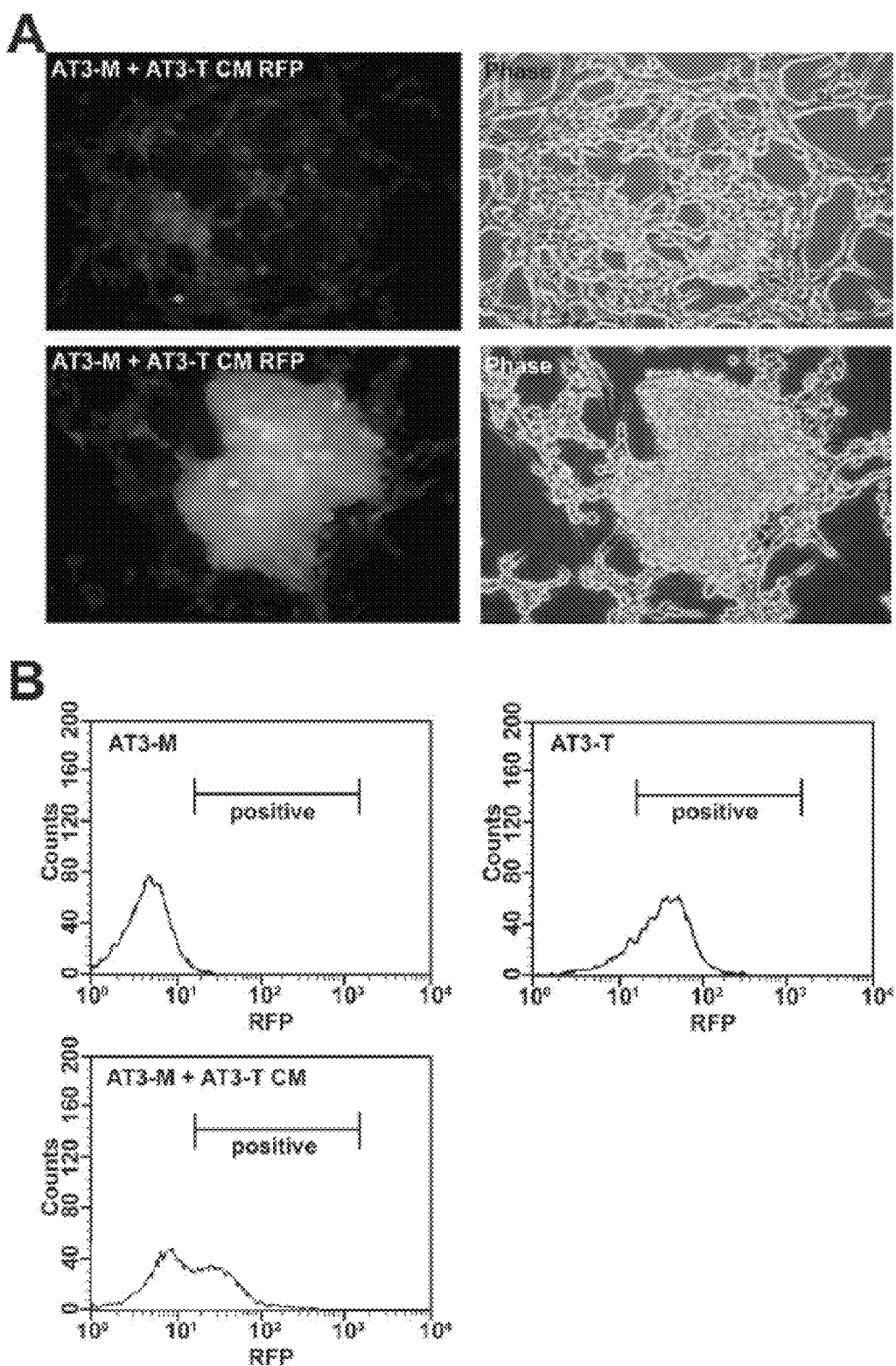
FIG. 2. (A) depicts examples of clusters of DsRED positive cells formed by AT3-M cells upon treatment with conditioned media from clone AT3-T. (B) depicts flow cytometry analysis of the same experiment.

A media exchange experiment was used to investigate whether or not the splicing of RIIIcI$^2$ transcripts in the DsRED expressing clones was regulated by soluble factors. Media conditioned by DsRED expressing clones (clone 5 in Table 2) was filtered and added to DsRED negative clones (clone 11 in Table 2). DsRED+ cells were observed among DsRED-cells incubated with DsRED+ conditioned media (FIG. 2). FIG. 2A shows examples of clusters of DsRED positive cells formed by AT3-M cells upon treatment with conditioned media from clone AT3-T. Media was conditioned for 24 h, filtered and added on AT3-M cells. Pictures (acquired at 200×) are taken 48 h following media exchange. FIG. 2B shows results from flow cytometry analysis of the same experiment. Left upper panel represents clone AT3-M conditioned with media from the same clone, as a negative control. Right upper panel represents clone AT3-T, which is DsRED positive. The lower panel represents clone AT3-M 48 h after conditioned media from clone AT3-T was added. Different lots of fetal bovine serum caused variation in this effect. This effect was quantified by flow cytometry and these data suggested that about half of the DsRED− cells were induced to express DsRED at levels equivalent to those seen in DsRED+ cells (FIG. 2). The changes observed were not due to prolonged culture of the cells in the same wells because conditioned media from a separate DsRED− culture did not induce DsRED expression. As shown in FIG. 2, AT3-T conditioned media induced AT3-M cells to express DsRED. These observations suggest that soluble factors secreted by the DsRED+ clones or dilution of factors extant in the DsRED− conditioned media may contribute to plasticity.

Example 3

AT3-M and AT3-T Cells are Tumorogenic

The initial characterization of the AT3-T revealed that these transitional cells grew slower and reached a lower confluent density than the AT3-M (FIG. 3A). FIG. 3A shows growth curves for clones AT3-T and AT3-M. Cells were plated at 0 h time-point, trypsinized, and counted at the indicated times. Data are the mean ±S.D. (n=3). To investigate their growth in vivo AT3-M and AT3-T cells were co-transfected with pGint a plasmid that expresses EGFP (herein GFP) in both mesenchymal and epithelial cells, and sorted stable populations of each cell line using flow cytometry for uniform GFP intensity. The GFP expressing cells maintained the morphological characteristics, the differential DsRED expression, and the differences in the splicing of pRIIIcI$^2$ and FGFR2 transcripts first observed after subcloning.

Figure 3:
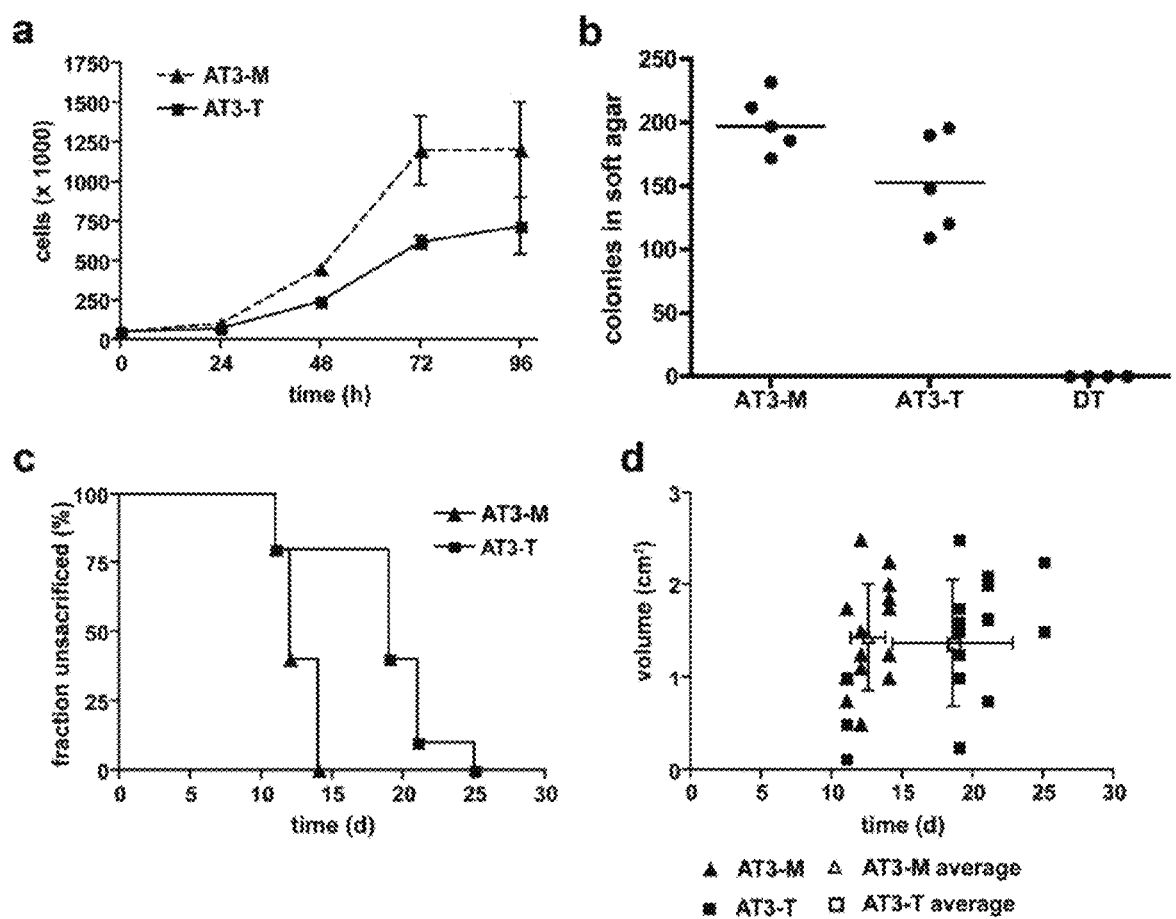
FIG. 3. (A) depicts growth curves for clones AT3-T and AT3-M. (B) is graph of growth of AT3-M, AT3-T, and DT cells in soft agar. (C) depicts a sacrifice curve for rats injected with AT3-M or AT3-T cells. (D) depicts a comparison of tumor volumes resulting from AT3-T and AT3-M injection.

We injected 3×10$^5$ GFP-expressing AT3-T or AT3-M cells subcutis in both flanks of Copenhagen white 2331 male rats. All of the animals developed bilateral tumors, indicating that both AT3-M and AT3-T cells were highly tumorogenic in these syngeneic rats. As a humane endpoint, rats were sacrificed when tumor length estimated by palpation reached 1 cm. The in vivo growth curves for the AT3-M and AT3-T tumors were significantly different, as determined by a logrank test (p=0.0020; FIG. 3B). FIG. 3B is a sacrifice curve for rats injected with AT3-M or AT3-T cells. FIG. 3C shows comparison of tumor volumes resulting from AT3-T and AT3-M injection. The Y-axis represents tumor volumes at the time of sacrifice of the animals and the X-axis days from the time of implantation to the time of sacrifice. Average tumor volumes and average days until sacrifice are represented with S.D. bars. Some points represent more than one tumor with the same volume on the same day. Tumor volume was measured (FIG. 3C) and although most AT3-T animals were sacrificed later, there was no significant difference in tumor size (p=0.76). As shown in FIG. 3, AT3-T cells grew more slowly than the mesenchymal-like AT3-M cells in vitro and in vivo, but both were equally tumorogenic. We concluded that whereas AT3-T cells grew more slowly in vitro and in vivo relative to their more mesenchymal siblings, these transitional cells were capable of forming tumors.

Example 4

Both AT3-M and AT3-T are Plastic

Figure 4:
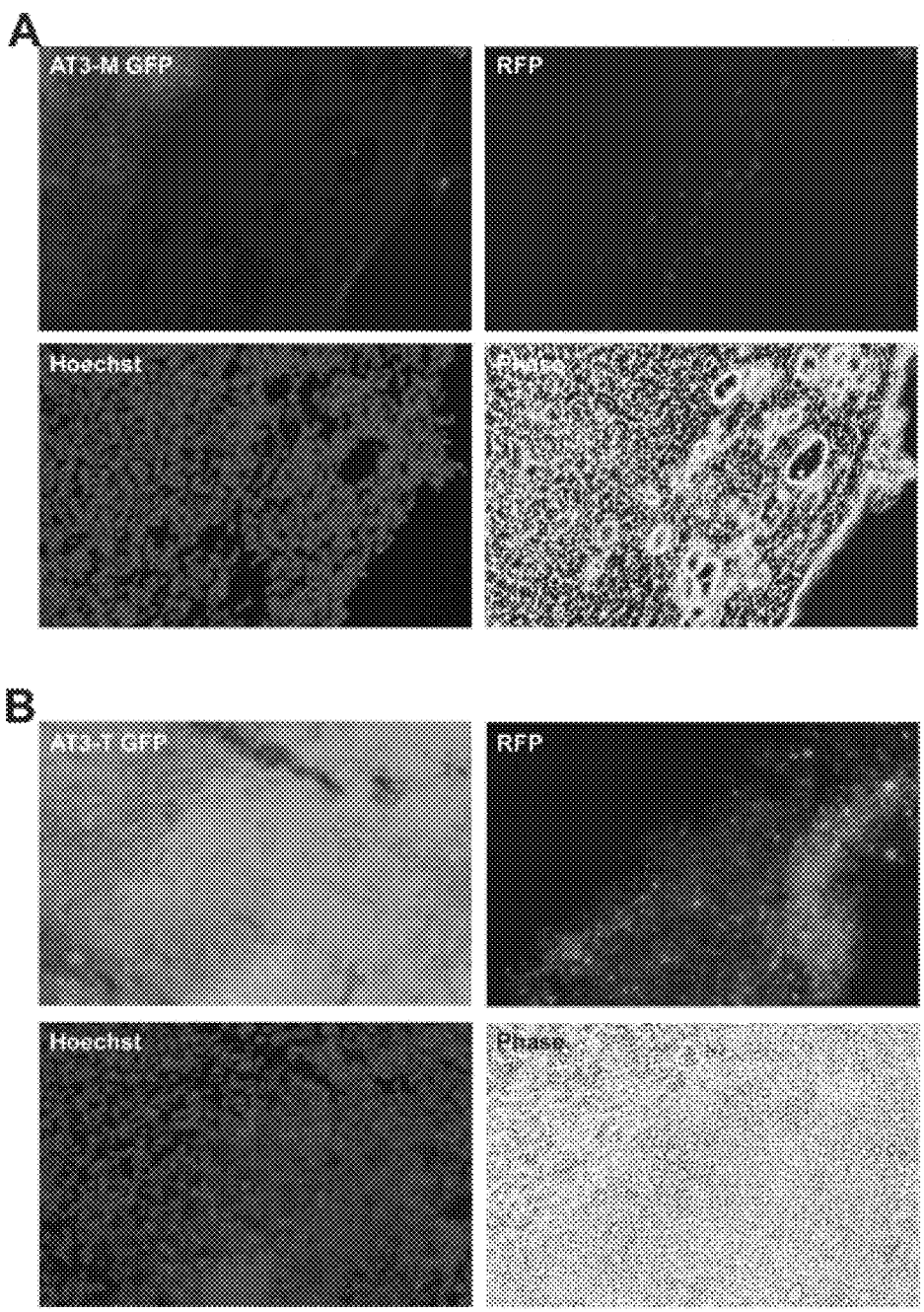
FIG. 4. (A) depicts a representative example of cells that express both RFP and GFP at the periphery of an AT3-M tumor stably transfected with Gint and pRIIIcI$^2$ reporters. (B) a representative example of a section from an AT3-T tumor stably transfected with GFP and pRIIIcI$^2$ reporters.
Figure 5:
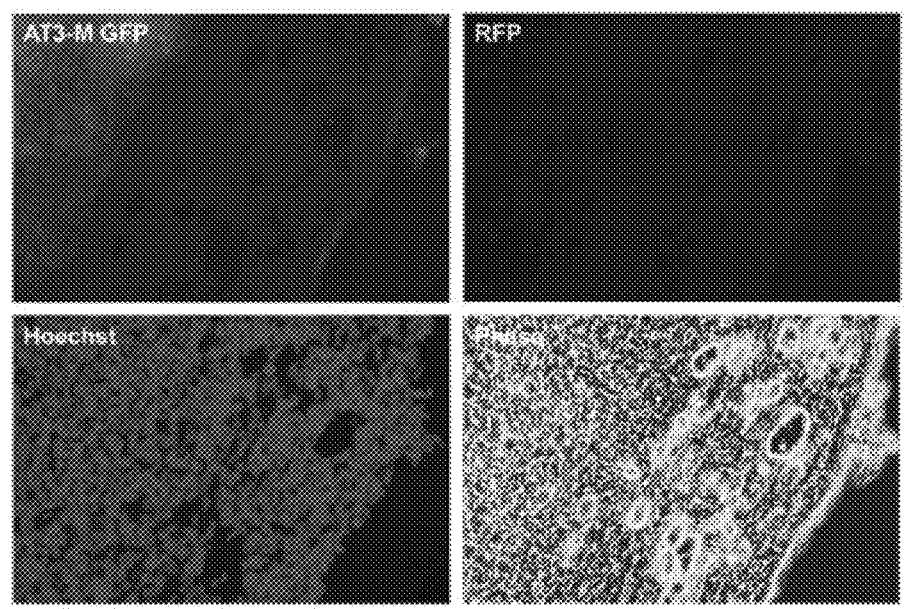
FIG. 5 depicts a representative example of cells that express both RFP and GFP at the periphery of an AT3-M tumor stably transfected with Gint and pRIIIcI$^2$ reporters.

Since the implanted AT3-M and AT3-T cells could be tracked by GFP expression, and epithelial character could be interrogated by DsRED expression, the plasticity of the tumors were able to be investigated. The overwhelming majority of cells in AT3-M tumors expressed GFP but not DsRED (FIG. 4A). As shown in FIG. 4, tumors from both AT3-T and AT3-M clones have evidence of plasticity. FIG. 4A shows representative example of cells that express both RFP and GFP at the periphery of an AT3-M tumor stably transfected with Gint and pRIIIcI$^2$ reporters. Pictures were taken at 200× magnification. To compensate for a low RFP signal, the color curve of the entire picture was adjusted. Nonetheless, groups of cells were observed expressing both GFP and DsRED in many AT3-M tumor sections, especially near the tumor capsule, (FIG. 4A; see also FIG. 5). FIG. 5 shows a representative example of cells that express both RFP and GFP at the periphery of an AT3-M tumor stably transfected with Gint and pRIIIcI$^2$ reporters. Pictures were taken at 200× magnification. In this version, overall RFP signal was not adjusted via color curve after the image was captured. RFP positive cells were clearly above background level.

Many sections from AT3-T tumors co-expressed GFP and DsRED; however, large areas were observed that expressed GFP but not DsRED in all 64 sections surveyed (FIG. 4B). FIG. 4B shows representative example of a section from an AT3-T tumor stably transfected with GFP and pRIIIcI$^2$ reporters. Pictures were taken at 200× magnification. RNA extracted from these regions of AT3-T tumors confirmed the presence of the pRIIIcI$^2$ transcripts. Both AT3-T and AT3-M cells were plastic and produced tumors with cells that displayed a range of epithelial-mesenchymal properties.

Example 5

AT3-T Cells are Motile In Vitro and Metastatic In Vivo

Figure 6:
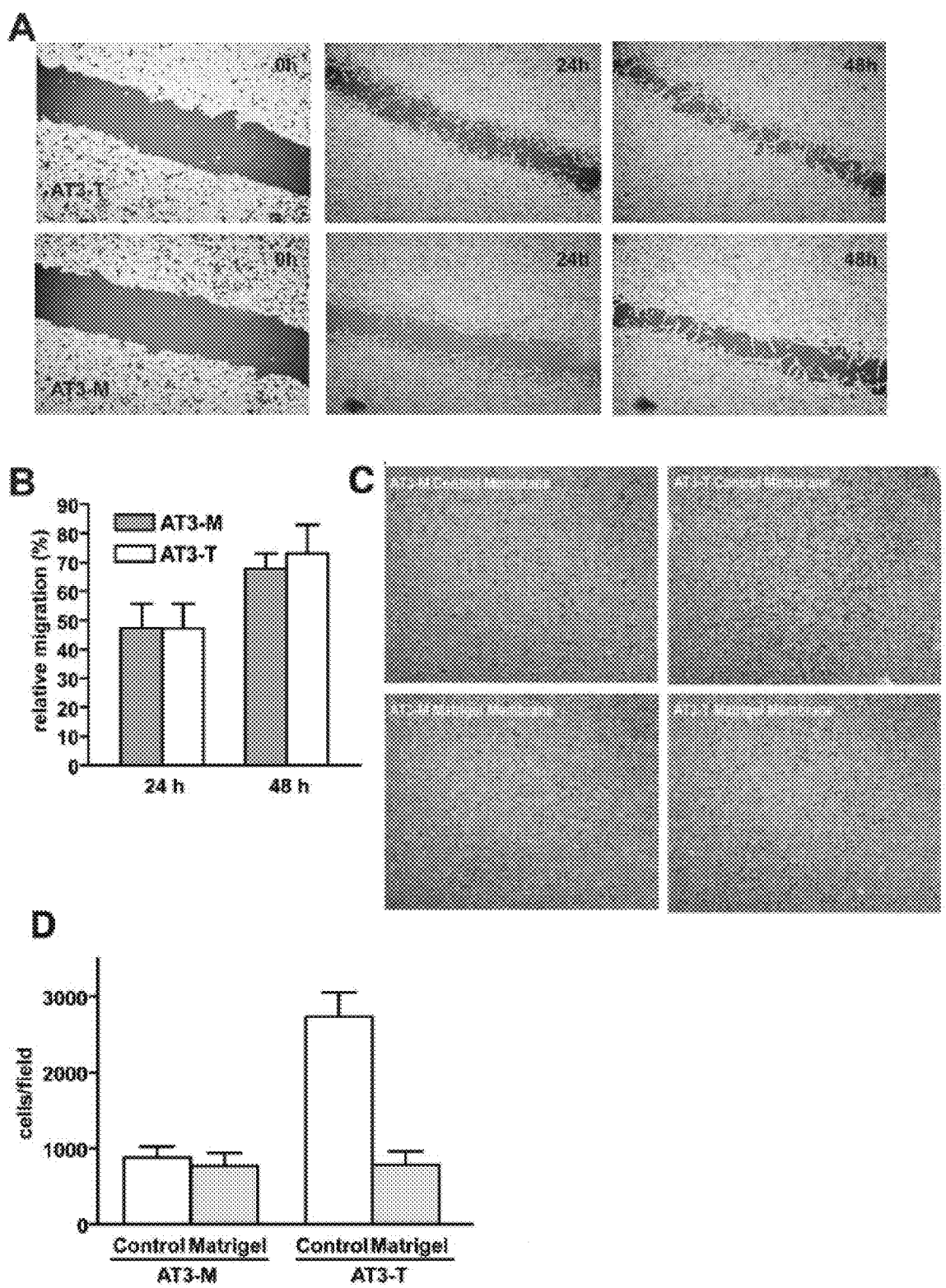
FIG. 6. (A) depicts representative pictures of cells for the scratch-wound assay. (B) a quantification of migration. (C) an invasion assay using Matrigel coated membranes. (D) a quantification of invasion assay results.

Comparison of AT3-T and AT3-M mobility and invasive potential was performed in culture. Motility was measured in culture by a "wound closure" assay, and no significant motility difference (p=0.59) was found between cell lines 24 and 48 hours after a scratch-wound had been made in the cultures (FIG. 6). FIG. 6A shows representative pictures for the scratch-wound assay (experiment done in triplicate for each clone). Pictures were taken at 40× magnification. FIG. 6B shows quantification of migration as explained in Methods. Mean and SO values were derived from triplicate experiments. FIG. 6C shows invasion assay using Matrigel coated membranes. Representative pictures of each clone and for both control membranes and Matrigel-coated membranes (n=5). Cells were stained with hematoxylin-eosin. Pictures were taken at 40× magnification. FIG. 6D shows quantification of invasion assay results. Mean and SD values were derived from five individual experiments. To gauge invasive properties of the cells we measured the number of cells traversing through Matrigel membranes in a 22-hour period. The same number of AT3-T and AT3M cells was observed on the Matrigel membranes suggesting that the two cell lines were equally capable of invading this membrane (FIG. 6). While a higher number of cells from clone AT3-T were observed on the control membrane compared to clone AT3-M, these studies nevertheless indicated that the more epithelial AT3-T cells had similar motility and invasive potential as the AT3-M cells. As shown in FIG. 6, AT3-M and AT3-T cells exhibited similar migration in vitro.

Figure 7:
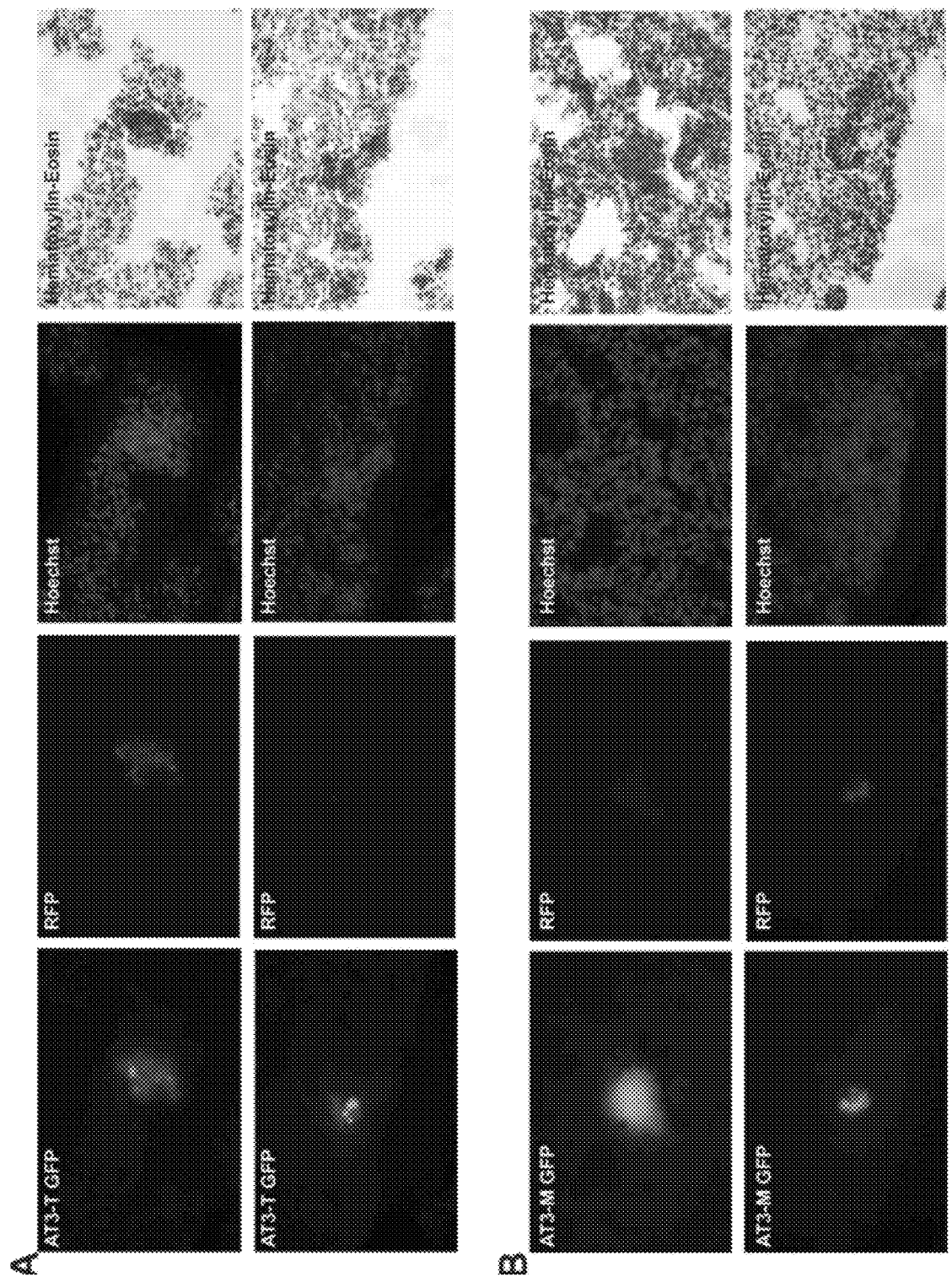
FIG. 7 are metastatic foci in lungs from animals with tumors from either AT3-T or AT3-M clones (stably transfected with GFP and pRIIIcI$^2$ reporters). (A) (upper panel) is an example of a section exhibiting the pattern for clone AT3-T (i.e. GFP+, DsRED+) in a metastatic focus and (lower panel) an example of a section exhibiting a plastic pattern for clone AT3-T (i.e. GFP+, DsRED−) in a metastatic focus. (B) (upper panel) is an example of a section exhibiting the pattern for clone AT3-M (i.e. GFP+, DsRED−) in a metastatic focus and (lower panel) an example of a section exhibiting a plastic pattern for clone AT3-M (i.e. GFP+, DsRED+) in a metastatic focus.

In order to assess invasiveness in vivo lungs from the twenty animals harboring AT3-M and AT3-T tumors were examined for presence of metastatic foci. No macroscopic metastatic nodules were observed in any of the lungs, which was likely due to the sacrificing protocol used on the animals when the tumors reached a specified size instead of using survival as the end-point. The GFP expression from the Gint reporter was examined to evaluate the presence of micro-metastases by epifluorescence microscopy. To assure a comprehensive evaluation, 7-8 equally spaced sections from each lung were surveyed (total of 150 sections for each clone). The presence of metastatic foci was determined by GFP fluorescence, followed by counter-staining of the sections with hematoxylineosin (FIG. 7). FIG. 7A shows (upper panel) an example of a section exhibiting the expected pattern for clone AT3-T (i.e. GFP+, DsRED+) in a metastatic focus, and (lower panel) an example of a section exhibiting a plastic pattern for clone AT3-T (i.e. GFP+, DsRED−) in a metastatic focus. FIG. 7B shows (upper panel) an example of a section exhibiting the expected pattern for clone AT3-M (i.e. GFP+, DsRED−) in a metastatic focus, and (lower panel) an example of a section exhibiting a plastic pattern for clone AT3-M (i.e. GFP+, DsRED+) in a metastatic focus. As shown in FIG. 7, metastatic foci in lungs from animals with tumors from either AT3T or AT3-M clones (stably transfected with GFP and pRIIIcI$^2$ reporters) had evidence of plasticity. Metastatic foci were found in 7 out of 10 lungs for clone AT3-M and 6 out of 10 lungs for clone AT3-T.

Evaluation of the plasticity of the metastatic foci using the combined output of the GFP and DsRED reporters revealed plastic foci (DsRED+ for AT3-M and DsRED− for AT3-T) in the case of both clones: 3 out of 12 for clone AT3-T and 13 out 16 for clone AT3-M (FIG. 7). These studies indicated phenotypic plasticity for the AT3-M cells and suggested it for the AT3-T cells. Importantly, both cell lines were metastatic despite differences in the original epithelial vs. mesenchymal phenotype.

Plasticity and metastatic behavior of cancer cells. Both the mesenchymal AT3-M and the more epithelial AT3-T cells metastasized efficiently. The drivers of metastasis, however, may be different in these two cells. The gene expression comparison between the AT3-M and AT3-T clones revealed at least one intriguing possibility: microarray analysis showed a 12-fold increase in the expression of junctional adhesion molecule C (JAM-C) in AT3-T compared to AT3-M, and this was confirmed by RT-PCR and immunoblot analysis. JAMs were present in leukocytes and at the tight junctions of epithelial and endothelial cells and have been shown to be involved in transendothelial migration of monocytes. JAM-C is expressed in several cell lines with high metastatic potential and knock-down of this molecule in the HT1080 human fibrosarcoma line significantly decreases its metastatic properties in vivo. Moreover, JAM-C is also present in the gene sets associated with stemness that had significant overlaps with genes that define clone AT3-T. Therefore clone AT3-T, by over-expression of different adhesion molecules may acquire metastatic capabilities. In addition, the overexpression of the downstream Hedgehog pathway effector GLI3 may be significantly upregulated in the more epithelial and stem cell-like AT3-T cells as compared to the more mesenchymal AT3-M cells. Hedgehog signaling has been linked to EMT, stemness, and metastasis/aggressiveness in several tumor types, and thus differential expression or regulation of developmental programs may underly these phenotypical differences across these cell lines. Increased expression of Patched, a Hedgehog pathway component, has been linked to prostate tumors during progression to androgen independence and in circulating tumor cells of men with metastatic castration-resistant prostate cancer.

Example 6

AT3-T Cells Display a Stem Cell-Like Gene Expression Signature

Figure 8:
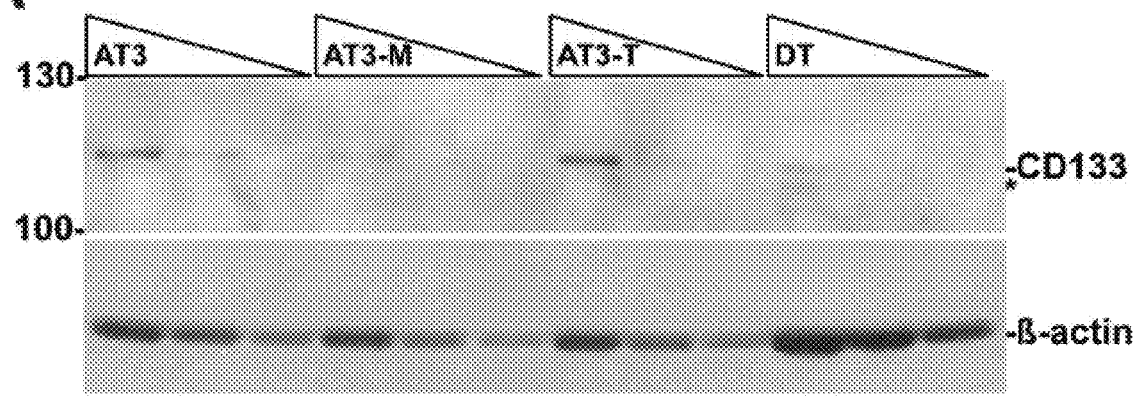
FIG. 8A depicts a membrane with serial two-fold dilutions of whole cell lysates cut in half and immunoblotted for CD133 (upper panel) or (β-actin (lower panel). (B) a membrane with serial twofold dilutions of whole cell lysates cut in half and immunoblotted for CD44 (upper panel) or β-actin (lower panel).
Figure 8:
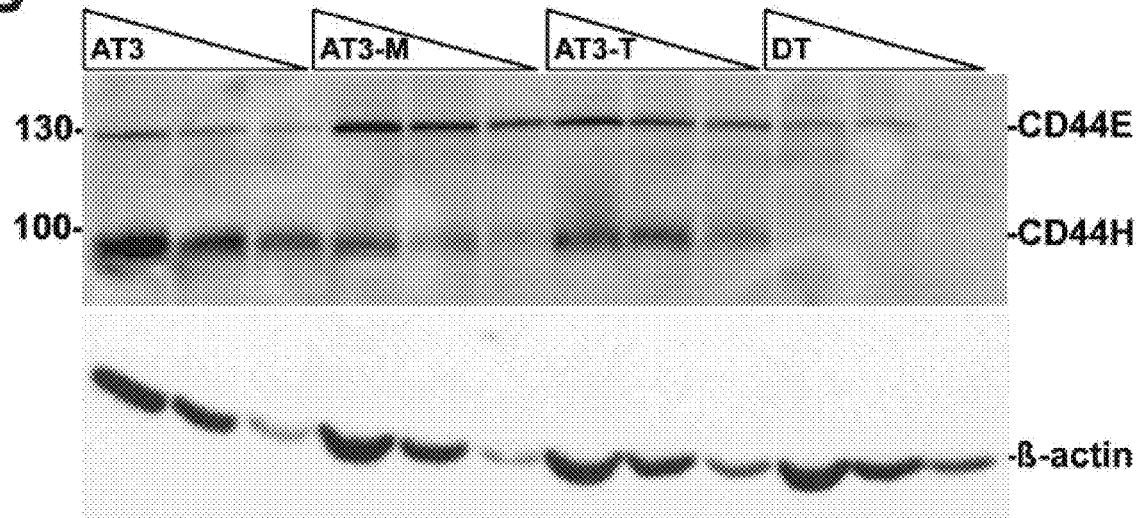

AT3-T cells sometimes formed tight clusters resembling protospheres. While sphere formation is not an exclusive property of stem cells, it has been associated with stemness in many different systems. Given these observations and the high tumorogenicity of AT3-T and AT3-M cells, they were tested for the expression of markers associated with cancer stem-like cells. Also included were the parental AT3 cells and another Dunning tumor cell line, DT cells, which display epithelial markers and are only weakly tumorogenic in Copenhagen white rats. The DT cells expressed very low levels of CD44 and CD133, which are associated with highly malignant cancer stem-like cells (FIG. 8). CD133 was detectable in DT lysates only when four fold more lysate was loaded. The mesenchymal-like AT3 cells expressed much higher levels of both CD44 and CD133 than the DT cells (note that the lanes for the DT samples are overloaded in FIG. 8A), which is consistent with recent reports that EMT induces stemness in mammary epithelial carcinoma cells. FIG. 8A shows a membrane with serial twofold dilutions of whole cell lysates was cut in half and immunoblotted for CD133 (upper panel) or β-actin (lower panel). Size markers are in kDa. A faster migrating CD133 band repeatably detected only in DT lysates is marked (*), suggesting possible post-translational regulation. FIG. 8B shows a membrane with serial twofold dilutions of whole cell lysates was cut in half and immunoblotted for CD44 (upper panel) or β-actin (lower panel). Representative blots from two independent sets of lysates are shown. AT3-T expressed CD44 and CD133. Interestingly, the AT3-T cells expressed overall higher levels of CD44 and CD133 than the more mesenchymal AT3-M. Moreover, AT3-T cells expressed a higher ratio of CD44H to CD44E when compared to AT3-M cells. The CD44H isoform has been associated with malignancy while CD44E is not. This suggests a more complex relationship between epithelial transitions and acquisition of stem cell-like properties. Consistent with expression of stem-like markers, both AT3-M and AT3-T cells formed colonies in soft agar and tumors when injected into Copenhagen white rats, and these tumors led to extensive metastases similar to parental AT3 cells (FIG. 3B).

To further explore these connections between transitions and stemness, global gene expression in AT3-M and AT3-T cells was compared. This analysis showed that 422 genes were differentially expressed (≥2-fold; p-value <0.05) in these two cells (Table 3). Many of the genes that were upregulated in AT3-T relative to AT3-M were preferentially expressed in epithelial cells and vice versa for those preferentially expressed in mesenchymal cells (Table 4). There were exceptions to this, however. Expression of the gene disintegrin-like and metalloprotease was consistent with a mesenchymal phenotype, but this mRNA level was 4-fold higher in AT3-T compared to AT3-M. Integrin β-4, normally associated with epithelial-like cells, was expressed 3-fold lower in AT3-T compared to AT3-M. These observations were consistent with the characterization of AT3-T cells as displaying more epithelial features than AT3-M cells and as populating an intermediate phenotypic state.

TABLE 3

| x Fold change (AT3-T/AT3-M) | Gene Symbol (Human) | Gene Symbol (Rat) |
| --- | --- | --- |
| 0.00771 | P2RX5 | P2rx5 |
| 0.011 | CCNB1lP1 | #N/A |
| 0.0296 | STRA6 | Stra6 |
| 0.0327 | G0S2 | G0s2 |
| 0.0835 | SERPINF1 | Serpinf1 |
| 0.101 | GSTA1 | #N/A |
| 0.107 | RSNL2 | Clip4 |

TABLE 3-continued

| x Fold change (AT3-T/AT3-M) | Gene Symbol (Human) | Gene Symbol (Rat) |
|---|---|---|
| 0.115 | ADAMTS7 | #N/A |
| 0.134 | GZMB | #N/A |
| 0.137 | SPON2 | #N/A |
| 0.156 | MMP3 | #N/A |
| 0.191 | ATP8A1 | #N/A |
| 0.197 | EVPL | Evpl |
| 0.21 | LGALS3BP | Lgals3bp |
| 0.216 | SERPINB2 | Serpinb2 |
| 0.219 | NETO2 | Neto2 |
| 0.223 | PTX3 | #N/A |
| 0.23 | SERPINB7 | Serpinb7 |
| 0.233 | RASIP1 | #N/A |
| 0.235 | OMD | #N/A |
| 0.239 | HLA-G | #N/A |
| 0.239 | HLA-A | #N/A |
| 0.247 | CD97 | Cd97 |
| 0.251 | GJA4 | Gja4 |
| 0.254 | DSU | #N/A |
| 0.257 | MGLL | Mgll |
| 0.261 | SPHK1 | #N/A |
| 0.268 | HRBL | Zcwpw1 |
| 0.268 | ZCWPW1 | Zcwpw1 |
| 0.27 | ENPP3 | Enpp3 |
| 0.275 | PTGS1 | Ptgs1 |
| 0.278 | RAMP1 | Ramp1 |
| 0.281 | DHRS3 | Dhrs3 |
| 0.282 | FAM117A | Fam117a |
| 0.284 | TUBB2A///TUBB2B | Tubb2b |
| 0.284 | TUBB2B | Tubb2b |
| 0.285 | C10orf10 | LOC500300 |
| 0.289 | SYTL2 | #N/A |
| 0.291 | SLC39A4 | Slc39a4 |
| 0.292 | CHRD | Chrd |
| 0.292 | GIP | Gip |
| 0.293 | CKLF | Cklf |
| 0.294 | PLAU | Plau |
| 0.295 | GUF1 | #N/A |
| 0.307 | CGI-38 | Tppp3 |
| 0.311 | LECT2 | Lect2 |
| 0.318 | NQO2 | #N/A |
| 0.32 | C11orf75 | RGD1309410 |
| 0.324 | DOCK2 | #N/A |
| 0.325 | LGALS2 | #N/A |
| 0.326 | CASP4 | Casp1 |
| 0.326 | LTBP4 | Ltbp4 |
| 0.334 | HSPB1 | Hspb1 |
| 0.335 | ITGB4 | Itgb4 |
| 0.34 | BPHL | Bphl |
| 0.341 | FOXF2 | #N/A |
| 0.345 | MYH1 | #N/A |
| 0.345 | SMAD6 | Smad6 |
| 0.348 | TGFB1 | Tgfb1 |
| 0.351 | MMP10 | #N/A |
| 0.363 | MMP9 | Mmp9 |
| 0.363 | COL18A1 | Col18a1 |
| 0.366 | HES1 | #N/A |
| 0.369 | SLC35D2 | #N/A |
| 0.377 | ADORA2B | Adora2b |
| 0.377 | COL3A1 | Col3a1 |
| 0.379 | DPEP2 | Dpep2 |
| 0.382 | GPR153 | Gpr153 predicted |
| 0.383 | LOC55908 | #N/A |
| 0.389 | SELPLG | #N/A |
| 0.394 | P2RX1 | Atp2a3 |
| 0.394 | ATP2A3 | Atp2a3 |
| 0.394 | ADD3 | Add3 |
| 0.395 | TSPAN9 | Tspan9 |
| 0.399 | LOC54103 | #N/A |
| 0.4 | BFSP2 | #N/A |
| 0.4 | FLJ14213 | RGD1309969 |
| 0.4 | PGGT1B | Pggt1b |
| 0.401 | HCN2 | Hcn2 |
| 0.403 | C2orf33 | RGD1310230 |
| 0.404 | TMEPAI | #N/A |
| 0.405 | INHA | Inha |
| 0.406 | HPSE | #N/A |
| 0.409 | CRY1 | Cry1 |
| 0.413 | IL3RA | Il3ra |
| 0.413 | CDC42EP1 | #N/A |
| 0.416 | ARG1 | Arg1 |
| 0.417 | MAPK14 | Mapk14 |
| 0.419 | FLJ22028 | #N/A |
| 0.421 | GALR2 | Galr2 |
| 0.422 | TSPAN8 | Tspan8 |
| 0.422 | FAM77C | RGD1561205 |
| 0.422 | USP2 | Usp2 |
| 0.422 | LAMA3 | #N/A |
| 0.424 | CCNE1 | Ccne1 |
| 0.424 | NSF | Nsf |
| 0.428 | ST3GAL5 | St3gal5 |
| 0.429 | SYNJ2 | Synj2 |
| 0.43 | ADA | Ada |
| 0.43 | PCBP3 | Pcbp3 |
| 0.433 | ZNF43 | #N/A |
| 0.433 | C14orf130 | Ubr7 |
| 0.436 | SOS2 | #N/A |
| 0.436 | RASSF3 | #N/A |
| 0.436 | GLMN | Glmn |
| 0.438 | OSR2 | Osr2 |
| 0.44 | AGTPBP1 | Agtpbp1 |
| 0.444 | DBNDD2 | RGD1311642 |
| 0.445 | SGCB | #N/A |
| 0.446 | HBLD2 | Isca1 |
| 0.448 | SCARB1 | Scarb1 |
| 0.448 | EVI2A | Evi2a |
| 0.448 | AP4M1 | #N/A |
| 0.451 | IGF2BP3 | #N/A |
| 0.452 | FLJ10404 | Ddx41 |
| 0.454 | TGFB2 | Tgfb2 |
| 0.459 | PASK | Pask |
| 0.461 | C19orf37 | Zfp428 |
| 0.462 | BMP1 | Bmp1 |
| 0.464 | PTPN13 | Ptpn13 |
| 0.47 | PTPRG | #N/A |
| 0.47 | EFNB1 | Efnb1 |
| 0.472 | PER2 | Per2 |
| 0.472 | IRS3L /// LOC442715 | Irs3 |
| 0.472 | HRBL | Irs3 |
| 0.472 | MAP3K3 | Kcnh6 |
| 0.472 | WDR68 | Kcnh6 |
| 0.472 | KCNH6 | Kcnh6 |
| 0.472 | CCDC44 | Kcnh6 |
| 0.473 | CIB2 | Cib2 |
| 0.475 | MPZL1 | Mpzl1 |
| 0.475 | FADS2 | #N/A |
| 0.48 | ZNF185 | #N/A |
| 0.482 | SLC29A1 | Slc29a1 |
| 0.487 | RUNX3 | Runx3 |
| 0.488 | NINJ1 | Ninj1 |
| 0.489 | RASL11B | Rasl11b |
| 0.49 | ECE2 | Ece2 |
| 0.49 | TNNC2 | Tnnc2 |
| 0.491 | WASPIP | Wipf1 |
| 0.492 | FN1 | Fn1 |
| 0.494 | NDE1 | Nde1 |
| 0.494 | CAMK2G | Camk2g |
| 0.495 | CUTL1 | Cux1 |
| 0.495 | ABHD6 | Abhd6 |
| 0.495 | PTPN14 | Ptpn14 |
| 0.497 | FLJ13946 | #N/A |
| 0.498 | BAIAP2 | Baiap2 |
| 0.499 | MSL3L1 | Msl3l1 |
| 0.499 | DYNLT1 | Dynlt1 |
| 0.499 | GSTM3 | Gstm5 |
| 2 | CHES1 | Foxn3 |
| 2.004 | AQR | Aqr /// Znf770 |
| 2.006 | EPN1 | Epn1 |
| 2.011 | PPBP | Ppbp |
| 2.019 | SLC35D1 | #N/A |
| 2.022 | PTPRC | #N/A |
| 2.031 | USP47 | Usp47 |
| 2.041 | DHX29 | #N/A |
| 2.047 | HMOX1 | #N/A |
| 2.05 | CAV1 | Cav1 |

TABLE 3-continued

| x Fold change (AT3-T/AT3-M) | Gene Symbol (Human) | Gene Symbol (Rat) |
|---|---|---|
| 2.053 | BUB1B | Bub1b |
| 2.069 | KCNIP4 | #N/A |
| 2.072 | — | #N/A |
| 2.072 | ADAM10 | #N/A |
| 2.073 | KIAA1155 | #N/A |
| 2.074 | PSTPIP2 | #N/A |
| 2.083 | MAML1 | #N/A |
| 2.084 | RAB32 | #N/A |
| 2.089 | FAM111A | #N/A |
| 2.095 | ATRNL1 | #N/A |
| 2.101 | PPIC | Ppic |
| 2.101 | CHD4 | Chd4 |
| 2.109 | IDE | Ide |
| 2.117 | PITPNM3 | #N/A |
| 2.121 | NFE2L1 | Nfe2l1 |
| 2.121 | MFSD1 | #N/A |
| 2.133 | KITLG | Kitlg |
| 2.161 | ING3 | Ing3 |
| 2.167 | CD24 | #N/A |
| 2.169 | IDS | #N/A |
| 2.177 | MGC3196 | LOC686289 /// LOC690285 |
| 2.185 | FBXL11 | Fbxl11 |
| 2.185 | — | Fbxl11 |
| 2.191 | ZC3H12A | #N/A |
| 2.195 | RKHD2 | #N/A |
| 2.201 | LAMC2 | Lamc2 |
| 2.217 | KIF11 | Kif11 |
| 2.242 | SNAPC5 | Snapc5 |
| 2.252 | THRAP3 | #N/A |
| 2.261 | HS6ST1 | #N/A |
| 2.264 | OXCT1 | #N/A |
| 2.266 | TEK | #N/A |
| 2.268 | HIST2H4///H4/o/// LOC648164 | #N/A |
| 2.271 | TMF1 | Tmf1 |
| 2.273 | ZBTB7B | Zbtb7b |
| 2.274 | CAMSAP1L1 | RGD1310950 |
| 2.279 | CYP3A5 | Cyp3ai |
| 2.279 | CYP3A7 | Cyp3a9 |
| 2.279 | CYP3A4 | Cyp3a9 |
| 2.282 | PENK | Penk1 |
| 2.283 | KIAA2010 | Smek1 |
| 2.284 | CHRNA1 | #N/A |
| 2.299 | BAT3 | Bat3 |
| 2.302 | ROM1 | Rom1 |
| 2.306 | HOXB8 | #N/A |
| 2.309 | KLK14 | #N/A |
| 2.31 | SUV39H1 | #N/A |
| 2.315 | LOC440354///BOLA2/// LOC595101 | RGD1564579 |
| 2.315 | UBN1 | Ubn1 |
| 2.323 | C1orf103 | #N/A |
| 2.333 | EYA2 | Eya2 |
| 2.347 | MT2A | #N/A |
| 2.353 | KIAA1815 | Ermp1 |
| 2.355 | SETD1B | #N/A |
| 2.369 | MPHOSPH1 | Kif20b |
| 2.38 | EFNA1 | Efna1 |
| 2.392 | ABCF2 | Abcf2 |
| 2.397 | LIMA1 | Lima1 |
| 2.418 | EXTL3 | Extl3 |
| 2.418 | ARL6IP2 | Arl6ip2 |
| 2.442 | GRAMD3 | Gramd3 |
| 2.456 | JARID1A | Jarid1a |
| 2.476 | ARHGEF9 | Arhgef9 |
| 2.485 | CAD | Cad |
| 2.493 | RAI17 | #N/A |
| 2.526 | KIAA0284 | #N/A |
| 2.529 | SGPP1 | Sgpp1 |
| 2.531 | ABCB1 | #N/A |
| 2.531 | ABCB1///ABCB4 | #N/A |
| 2.542 | KIF1C | #N/A |
| 2.553 | KIAA0020 | LOC499339 |
| 2.563 | ADAM15 | Adam15 |
| 2.577 | UBE1 | Uba1 |
| 2.577 | INE1 | Uba1 |

TABLE 3-continued

| x Fold change (AT3-T/AT3-M) | Gene Symbol (Human) | Gene Symbol (Rat) |
|---|---|---|
| 2.58 | GRIP2 | Grip2 |
| 2.59 | PPEF1 | #N/A |
| 2.619 | SC65 | Sc65 |
| 2.62 | FER1L3 | #N/A |
| 2.62 | NOC3L | #N/A |
| 2.62 | RBP4 | #N/A |
| 2.645 | SPINK4 | Spink4 |
| 2.653 | ATXN2L | #N/A |
| 2.711 | AHCYL1 | Ahcyl1 |
| 2.723 | TUBB3 | Tubb3 |
| 2.723 | MC1R | Tubb3 |
| 2.729 | AGPAT7 | Lpcat4 |
| 2.749 | HOXC11 | #N/A |
| 2.766 | APH1A | Aph1a |
| 2.785 | CNOT1 | RGD1308009 |
| 2.785 | CSNK2A2 | RGD1308009 |
| 2.794 | STAC | #N/A |
| 2.904 | STAG1 | #N/A |
| 2.942 | MBNL1 | #N/A |
| 2.982 | MNT | Mnt |
| 3.007 | RANBP5 | Ipo5 |
| 3.014 | HERC1 | Herc1 |
| 3.065 | ALDOC | Aldoc |
| 3.122 | KIAA0460 | — |
| 3.174 | FLT3 | #N/A |
| 3.278 | CXCL6 | Cxcl6 |
| 3.366 | GLI3 | #N/A |
| 3.489 | SSR3 | #N/A |
| 3.585 | BCAN | Bcan |
| 3.824 | FKBP10 | Fkbp10 |
| 3.903 | GSTK1 | Gstk1 |
| 3.931 | PSCDBP | #N/A |
| 3.974 | ALCAM | Alcam |
| 4.056 | ADAMTS13 | |
| 4.203 | SPRR2B | #N/A |
| 4.276 | GPR126 | #N/A |
| 5.169 | SULF1 | Sulf1 |
| 5.529 | TFF1 | Tff1 |
| 6.52 | PTN | Ptn |
| 8.591 | MLF1 | Mlf1 |
| 9.012 | THBS2 | Thbs2 |
| 10.79 | HEPH | Heph |
| 12.53 | JAM3 | Jam3 |

TABLE 4

Examples of epithelial or mesenchymal genes in the expression data analysis of clones AT3-T and AT3-M.

| Gene name | x Fold change in AT3-T vs. AT3-M |
|---|---|
| Junctional adhesion molecule C | 12.53 |
| Disintegrin-like and metalloprotease | 4.05 |
| Activated leukocyte cell adhesion molecule | 3.97 |
| Tubulin | 2.73 |
| Epithelial protein lost in neoplasm | 2.39 |
| Laminin | 2.20 |
| TGFβ2 | 0.45 |
| MMP9 | 0.36 |
| Collagen, type XVIII | 0.36 |
| MMP10 | 0.35 |
| Integrin β4 | 0.33 |
| TGFβ1 | 0.31 |
| Urokinase plasminogen activator | 0.29 |
| MMP3 | 0.15 |

Two gene sets were assembled: one composed of gene products upregulated in AT3-T (relative to AT3-M) and the second of those downregulated in AT3-T (relative to AT3-M). The two gene sets were compared for overlap with 5,452 gene sets from the Molecular Signature Database collections (Gene Set Enrichment Analysis (GSEA) http://www.broad-.mit.edu/gsea/). Analysis of genes over-expressed in AT3-T relative to AT3-M for overlap with 5,452 gene sets from the Molecular Signature Database collections via Gene Set Enrichment Analysis (GSEA) did not show any significant enrichment of sets associated with EMT or MET. In this regard, both AT3-M and AT3-T resembled the mesenchymal-like, parental AT3 line. Among the 15 most significant overlaps for the genes overexpressed in AT3-T there were three sets of genes activated in hematopoetic stem cells ($p=3.24\times10^{-8}$), neural stem cells ($p=3.07\times10^{-7}$) and embryonal murine stem cells ($p=5.14\times10^{-6}$), (Table 5) while among the 20 most significant overlaps for the genes that are relatively downregulated in AT3-T cells were two gene sets associated with development of mature cell types. Expression of the downstream hedgehog pathway effector GLI3 was found to be 3.4-fold overexpressed in AT3-T cells compared to AT3-M cells, indicating that regulation of this developmental/stemness pathway in prostate cancer may be tied to the underlying phenotypic state during EMT/MET, similar to what has been reported in other tumors. These data indicated that AT3-T cells have gene expression profiles similar to stem cells, and, in concordance with the analysis of CD44 and CD133 protein expression, suggested that AT3-T cells exist in a more stem cell-like state than the more mesenchymal AT3-M cells.

TABLE 5

| GSEA Collections: | | | C1, C3, C2, C5, C4 | | |
|---|---|---|---|---|---|
| # overlaps shown: | | | 20 | | |
| # gene sets in collections: | | | 5452 | | |
| # genes in comparison (N) | | | 127 | | |
| # genes in collections (N) | | | 39655 | | |
| gene set name | # genes in gene set (k) | Description | # genes in overlap (k) | k/K | p value |
| TATAAA_V$TATA_O1 | 1333 | Genes with promoter regions [−2 kb, 2 kb] around transcription start site containing the motif TATAAA which matches annotation for TAF<br> TATA | 20 | 0.015 | 8.07E−09 |
| STEMCELL_HEMATOPOIETIC_UP | 1452 | Enriched in mouse hematopoietic stem cells, compared to differentiated brain and bone marrow cells | 20 | 0.0138 | 3.24E−08 |
| GNF2_RAP1B | 37 | Neighborhood of RAP1B | 5 | 0.1351 | 1.23E−07 |
| STEMCELL_NEURAL_UP | 1838 | Enriched in mouse neural stem cells, compared to differentiated brain and bone marrow cells | 21 | 0.0114 | 3.07E−07 |
| module_2 | 383 | Genes in Module_2 | 10 | 0.0261 | 4.34E−07 |
| CTTTGA_V$LEF1_Q2 | 1270 | Genes with promoter regions [−2 kb, 2 kb] around transcription start site containing the motif CTTTGA which matches annotation for LEF1: lymphoid enhancer-binding factor 1 | 17 | 0.0134 | 5.48E−07 |
| SIGNAL_TRANSDUCTION | 1637 | Genes annotated by the GO term GO:0007165. The cascade of processes by which a signal interacts with a receptor, causing a change in the level or activity of a second messenger or other downstream target, and ultimately effecting a change in the functioning of the cell. | 19 | 0.0116 | 9.33E−07 |

TABLE 5-continued

| | | | | | |
|---|---|---|---|---|---|
| module_385 | 28 | Genes in module 385 | 4 | 0.1429 | 1.91E06 |
| V$MYCMAX_01 | 261 | Genes with promoter regions [−2 kb, 2 kb] around transcription start site containing the motif NNACCACGTGG TNN which matches annotation for MYC: v-myc myelocytomatosis viral oncogene homolog (avian)<br> MAX: MYC associated factor X | 8 | 0.0307 | 1.98E06 |
| GGGCGGR_V$SP1_Q6 | 3053 | Genes with promoter regions [−2 kb, 2 kb] around transcription start site containing the motif GGGCGGR which matches annotation for SP1: Sp1 transcription factor | 26 | 0.0085 | 2.59E−06 |
| AACTTT_UNKNOWN | 1963 | Genes with promoter regions [−2 kb, 2 kb] around transcription start site containing motif AACTTT. Motif does not match any known transcription factor | 20 | 0.0102 | 3.29E−06 |
| V$AP1_C | 281 | Genes with promoter regions [−2 kb, 2 kb] around transcription start site containing the motif NTGASTCAG which matches annotation for JUN: jun oncogene | 8 | 0.0285 | 3.38E−06 |
| MEMBRANE_PART | 1673 | Genes annotated by the GO term GO:0044425. Any constituent part of a membrane, a double layer of lipid molecules that encloses all cells, and, in eukaryotes, many organelles; may be a single or double lipid bilayer; also includes associated proteins. | 18 | 0.0108 | 5.09E−06 |
| STEMCELL_EMBRYONIC_UP | 1344 | Enriched in mouse embryonic stem cells, compared to differentiated brain and bone marrow cells | 16 | 0.0119 | 5.14E−06 |
| INTRINSIC_TO_MEMBRANE | 1350 | Genes annotated by the GO term GO:0031224. Located in a membrane such that some covalently attached portion of the gene product, for example part of a | 16 | 0.0119 | 5.43E−06 |

TABLE 5-continued

| | | | | | |
|---|---|---|---|---|---|
| | | | peptide sequence or some other covalently attached moiety such as a GPI anchor, spans or is embedded in one or both leaflets of the membrane. | | | |
| CELL_SURFACE | | 79 | Genes annotated by the GO term GO:0009986. The external part of the cell wall and/or plasma membrane. | 5 | 0.0633 | 5.58E−06 |
| UVC_XPCS_8HR_DN | | 408 | Down-regulated at 8 hours following treatment of XPB/CS fibroblasts with 3 J/m^2 UVC | 9 | 0.0221 | 6.35E−06 |
| NOTCH_SIGNALING_PATHWAY | | 12 | Genes annotated by the GO term GO:0007219. The series of molecular signals initiated by binding of an extracellular ligand to a Notch receptor on the surface of the target cell. | 3 | 0.25 | 6.86E−06 |
| LEI_MYB_REGULATED_GENES | | 325 | Myb-regulated genes | 8 | 0.0246 | 9.62E−06 |
| MORF_DDB1 | | 246 | Neighborhood of DDB1 | 7 | 0.0285 | 1.40E−05 |

Figure 9:
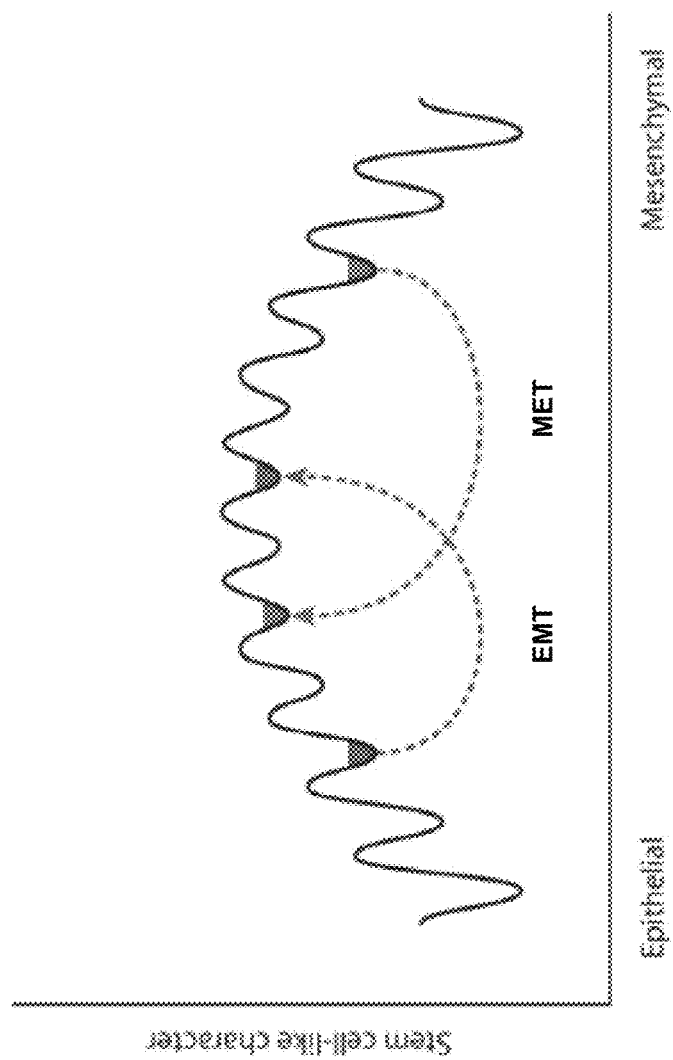
FIG. 9 depicts a model comparing stem cell-like character and epithelial mesenchymal phenotype.

Epithelial plasticity and stem cell-like behavior. It is well appreciated that cells induced to undergo EMT activate stem cell pathways. Work presented here shows that AT3 cells that transitioned towards a more epithelial state, i.e. were involved in MET, also activated expression of stem cell-like markers. This finding suggested a broader relationship between plasticity and stem cell-like character or stemness, which was modeled using a Gibbs free energy diagram (FIG. 9). FIG. 9 shows a model comparing stem cell-like character and epithelial-mesenchymal phenotype. The x-axis represents the spectrum of epithelial to mesenchymal phenotypes and the y-axis represents the stem cell-like character of the cells. The left arrow represents an EMT and the right arrow represents an MET. The model posits that as cells transition back and forth along the epithelial and mesenchymal x-axis they course through states of varying stemness, and this property peaks at intermediate states between epithelial and mesenchymal phenotypes. The number of different states and the exact height of the barriers between states are speculative and are not meant to be taken as proportional. Two phenotypic transitions are shown, the first is a partial EMT (left arrow) and the second is a partial MET (right arrow). Both of these transitions result in states with higher stem cell-like character. It should be noted that the model also predicts that some EMTs, and equally some METs, will result in a decrease in stemness and indeed this has been observed when the highly aggressive human DKAT basal-type breast cancer cell line is induced to undergo EMT (N. D'Amato and V. Seewaldt, personal communication). The model also suggests a link between stemness, plasticity, and metastatic propensity, perhaps explained by activation of certain oncogenic pathways (e.g., PI3 kinase/Akt) and developmental pathways.

The model also predicts that cells with maximal stem-cell character, which by definition will be highly malignant, should display both epithelial and mesenchymal traits, because they inhabit intermediate states in the epithelialmesenchymal axis. The highly malignant rat adenocarcinoma AT3-T cells are in this type of state. Importantly, in humans with metastatic breast and prostate carcinomas many CTCs also exist in these intermediate states. These cells correlate with disease progression and are believed to be highly aggressive. A population of cells enriched in CTCs expressed RNAs encoding mesenchymal markers; however, the data did not indicate whether or not epithelial and mesenchymal markers were co-expressed in the same cell. Another clinical example of cells in intermediate states is found in sarcomatoid renal cell carcinomas, which have been shown to co-express epithelial markers, such as epithelial membrane antigen, and mesenchymal ones, like vimentin. These tumors, though rare (1-8% of renal tumors) are highly aggressive and difficult to treat. A similar situation may be found in carcinosarcomas of both the prostate and breast, highly aggressive, rare tumors with mixed epithelial and mesenchymal components but of clonal origin. It is not completely clear whether or not single cells in these tumor co-express epithelial and mesenchymal markers and are thus truly in intermediate states.

Finally, the model suggests that as sarcomas undergo MET they will activate stem cell-like pathways and become more aggressive. Indeed, there are many descriptions of sarcomas with mixed epithelial and mesenchymal components in close proximity as seen in some synovial- and osteo-sarcomas. New genetically-defined mouse models of soft tissue sarcoma should shed light on the existence and importance of cells intermediate cell states in progression of these tumors.

Example 7

Phenotypic Plasticity Among Human Circulating Tumor Cells

The experiments described above indicated that Dunning rat prostate adenocarcinoma cells that inhabit an intermediate phenotypic state are tumorogenic, metastatic, and possess stem cell-like antigens and cellular programs. To investigate whether or not similar transitional cells could play a role in human cancer, cancer cells isolated from blood of men with metastatic castrate resistant progressive prostate cancer (CRPC) or women with progressive metastatic breast cancer (mBC) were examined. Circulating tumor cells (CTCs) represent an ideal source of tissue to investigate evidence of this plasticity in vivo, given that these cells are likely to be in circulation prior to and during metastatic colonization. CTCs have both independent prognostic and predictive significance in multiple epithelial malignancies, including breast and prostate cancer. These cells can be collected, isolated, and analyzed for a variety of biomarkers relevant to cancer biology.

Figure 10:
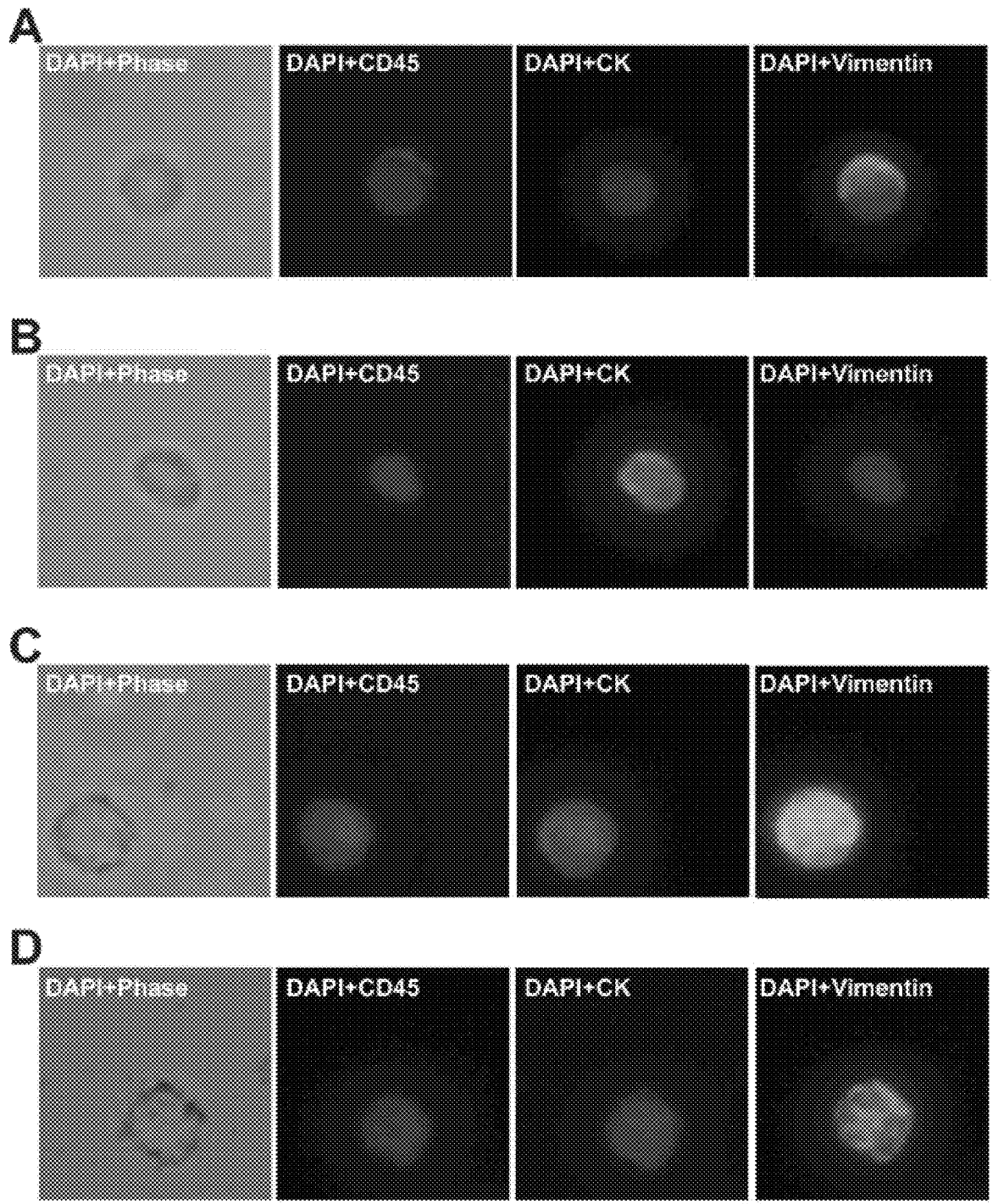
FIG. 10 depicts CTCs from patients with prostate adenocarcinoma. (A) illustrates an example of a leukocyte from a human peripheral blood mononuclear cell (PMBC) sample: CD45 (+), CK (−), and vimentin (+). (B) illustrates an example of a CD45 (−), CK (+), and vimentin (−) cell from a patient with metastatic breast cancer. (C) illustrates an example of a CD45 (−), CK (+), vimentin (+) from a patient with metastatic breast cancer (mBC). (D) illustrates an example of a CD45 (−), CK (+), vimentin (+) from a patient with metastatic progressive castrate-resistant prostate cancer (mCRPC).

It was tested whether there was a high likelihood of finding transitional cells within a population of CTCs captured by FDA-approved EpCAM (Epithelial Cell Adhesion Molecule)-targeted ferromagnetic antibodies. These cells were interrogated for expression of CD45 (expressed in many leukocytes; FIG. 10A), cytokeratin (CK; an epithelial marker), and vimentin (a mesenchymal marker) by immunofluorescence. CTCs were defined as CD45-negative and CK-positive nucleated intact cells (FIG. 10B) and transitional CTCs were so defined if they additionally co-expressed vimentin (FIG. 10C-D). FIG. 10 shows that CTCs from patients with prostate adenocarcinoma stained positive for epithelial and mesenchymal markers. Triple staining was performed using anti-CD45 antibody labeled with Alexa 647, anti-cytokeratin (CK) antibody labeled with Alexa 555, and anti-vimentin antibody labeled with Alexa 488. Nuclei were labeled with DAPI. FIG. 10A shows an example of a leukocyte from a human peripheral blood mononuclear cell sample: CD45 (+), CK (−), and vimentin (+). Additionally, CD45 (+), CK (−), and vimentin (−) cells were observed. FIG. 10B shows an example of a CD45 (−), CK (+), and vimentin (−) cell from a patient with metastatic breast cancer. Such cells were counted as vimentin (−) CTCs in Table 6. FIG. 10C shows an example of a CD45 (−), CK (+), vimentin (+) from a patient with metastatic breast cancer. Such cells were counted as vimentin (+) CTCs in Table 6. FIG. 10D shows an example of a CD45 (−), CK (+), vimentin (+) from a patient with metastatic progressive castrate-resistant prostate cancer. Such cells were counted as vimentin (+) CTCs in Table 6.

Transitional CTCs co-expressed vimentin and CK in many of the patients with elevated CTC counts (≥5 CTCs/7.5 mL by standard testing) (Table 6, FIG. 10). In fact, among nine patients with progressive metastatic CRPC and eight patients with progressive mBC, it was found that approximately 75% (range 0-100%, 85.5% in CRPC, 54% in mBC) of the CTCs stained for both CK and vimentin (FIG. 10C-D), indicating a transitional phenotype. These data indicated that circulating tumor cells in patients with metastatic breast and prostate cancer co-express epithelial (Ep-CAM and cytokeratin) and mesenchymal (vimentin) markers, and thus exist in a transitional phenotypic state, similar to that observed in our preclinical models.

TABLE 6

Circulating tumor cell (CTC) counts and vimentin expression in patients with metastatic castration resistant prostate or metastatic breast cancer.

| Subject Number | CTC Count (Cellsearch)* | Ratio: vimentin (+) CTCs/Total CTC Count |
|---|---|---|
| Castrate-Resistance Metastatic Prostates Cancer | | |
| 1 | 5 | 4/6 |
| 2 | 41 | 11/11 |
| 3 | 45 | 6/10 |
| 4 | 626 | 5/8 |
| 5 | 110 | 17/21 |
| 6 | 182 | 5/6 |
| 7 | 17 | 13/16 |
| 8 | 19 | 33/34 |
| 9 | 34 | 12/12 |
| Total | | 106/124 (85.5%) |
| Metastatic Breast Cancer | | |
| 1 | 21 | 0/6 |
| 2 | 7 | 2/2 |
| 3 | 8 | 4/4 |
| 4 | 21 | 1/2 |
| 5 | 12 | 2/2 |
| 6 | 188 | 21/22 |
| 7 | 138 | 8/20 |
| 8 | 377 | 6/23 |
| Total | | 44/81 (54.3%) |
| Overall Total | — | 150/205 (73.1%) |

*Column 2 represents the CTC count as determined by the standard Cellsearch EpCAM based method for each subject, while column 3 represents the number and proportion of CTCs counted manually that were found to express cytokeratin and co-express vimentin, expressed as a ratio and percentage.

Plasticity and CTCs. The identification of plasticity among CTCs in a significant subset of patient samples offers several important clinical opportunities. Expression of plasticity may have prognostic or predictive value in patients with metastatic cancers, especially mBC where a significant range of values were shown for plasticity. Thus, the subset of patients with very high plasticity may have a more aggressive natural history and exhibit greater resistance to systemic treatments. In terms of diagnosis and utility as predictive biomarkers the data suggested that in addition to cells expressing both epithelial and mesenchymal markers there may be an unknown number of CTCs that have moved further towards the mesenchymal pole and are EpCAM negative. These cells will be missed by the FDA approved CELLSEARCH® System and also by the Adna Test (Adna-Gen AG) system and current microfluidic technologies, which enrich for CTCs by immunoabsorbtion of cells expressing MUC1 or EpCAM. Indeed, recent studies in breast cancer have suggested that "normal" type breast cancer cell lines that overexpress both EMT and stem cell antigens (CD44+, CD24−) may lack EpCAM and are thus not detectable by currently approved CTC detection systems. Therefore it is possible that the number of CTCs in patients with metastatic cancer is much higher than currently appreciated. Identification of this additional subset of CTC can provide greater prognostic value than CTC counts as currently determined, as well as earlier detection of CTCs and the metastatic potential in patients with earlier stage disease.

Furthermore, CTCs in intermediate states, which comprise the 50-75% of cells isolated herein from patients with metastatic breast and prostate cancer as well as those cells that may go undetected because they have undergone a more complete EMT, represent a therapeutic problem. It has been well documented that EMT alters drug sensitivity of lung cancer cells and it has been challenging to direct therapy to cancer cells with stem cell-like properties, perhaps because of their recalcitrance to undergo apoptosis.

While recent studies suggest both a screening method and actual compounds (e.g., salinomycin) that can selectively target cancer stem cells, these aggressive cells still represent a formidable therapeutic challenge. Thus, molecules comprising a binding agent that has binding specificity to an EMT biomarker described herein and linked to an anti-cancer agent provide additional therapeutic options.

Example 8

CTCs From Patients with Metastatic Breast and Prostate Cancer Express Vimentin and N-Cadherin Eligible men had progressive metastatic CRPC (progression despite testosterone <50 ng/dL) and were about to begin a new systemic therapy. Eligible women had progressive metastatic breast cancer (mBC) and were about to begin a new systemic therapy. Baseline characteristics of patients (n=29) are presented in Table 7.

TABLE 7

Baseline characteristics of patients (n = 29)

|  | Metastatic Prostate (n = 17) | Metastatic Breast (n = 12) |
|---|---|---|
| DEMOGRAPHICS | | |
| Age, median | 69 (59-82) | 61.5 (48-81) |
| Race, Ethnicity | | |
| White, non-hispanic | 76% | 58% |
| Other, non-hispanic | 23% | 42% |
| BASELINE DISEASE HISTORY | | |
| Gleason Score, median | 7 (7-9) | — |
| ER/PR, % | — | 75%/67% |
| Baseline median PSA, Range | 396.4 (14-13,419.5) | — |
| Baseline Pain Score (0-10), median | 1 (0-7) | 0 (0-6) |
| Karnofsky Performance Status, median | 90 (70-100) | 90 (70-100) (n = 6) |
| # of Prior Hormonal Therapies | 2 (0-5) | 2 (0-4) |
| Prior Chemotherapy | 47% | 83% |
| Baseline CTC Count, median | 40 (4-828) | 13 (0-1062) |
| METASTATIC SITES | | |
| Lymph Node | 65% | 50% |
| Liver | 24% | 50% |
| Lung | 47% | 42% |
| Bone | 94% | 75% |

CTCs were drawn into standard FDA-approved Cellsave tubes and processed within 48 hours using the CELLSEARCH® methodology using EpCAM-based ferromagnetic capture. A CTC was defined as an intact nucleated (DAPI+) cell that expressed pan-CK and lacked expression of the leukocyte antigen CD45, and was enumerated using standard methods. A second CELLSEARCH® tube was collected and processed using EpCAM capture, and isolated cells were stained for CK (IgG1, AbD Serotec) labeled with Alexa 555, CD45 (IgG1, AbCam) labeled with Alexa 647, and either vimentin (IgG1, BD Biosciences) or N-Cadherin (IgG1, DAKO) using immunofluorescent labeling with Alexa 488. The proportion of CTCs staining positive for an EMT antigen was calculated from the total number of CTCs manually scored from the second tube. Positive controls using American Red Cross-derived PBMCs (CD45), PC3 prostate cancer cells (vimentin, N-cadherin), and T47D breast cancer cells (CK) were used for each marker. Negative controls using mock antibody were used to optimize the staining/scoring of each antigen.

Figure 11:
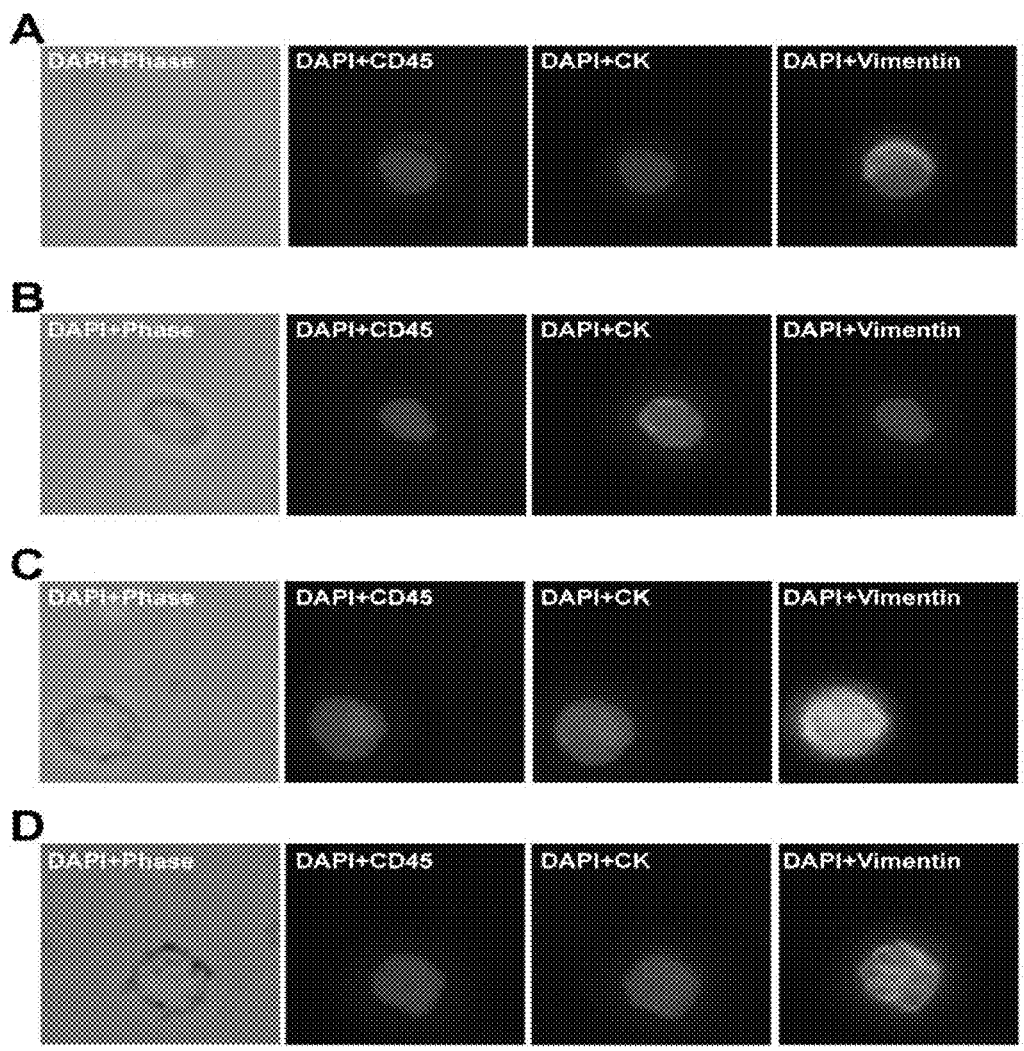
FIG. 11 depicts immunofluorescent images of CTCs from patients with mCRPC and mBC.
Figure 12:
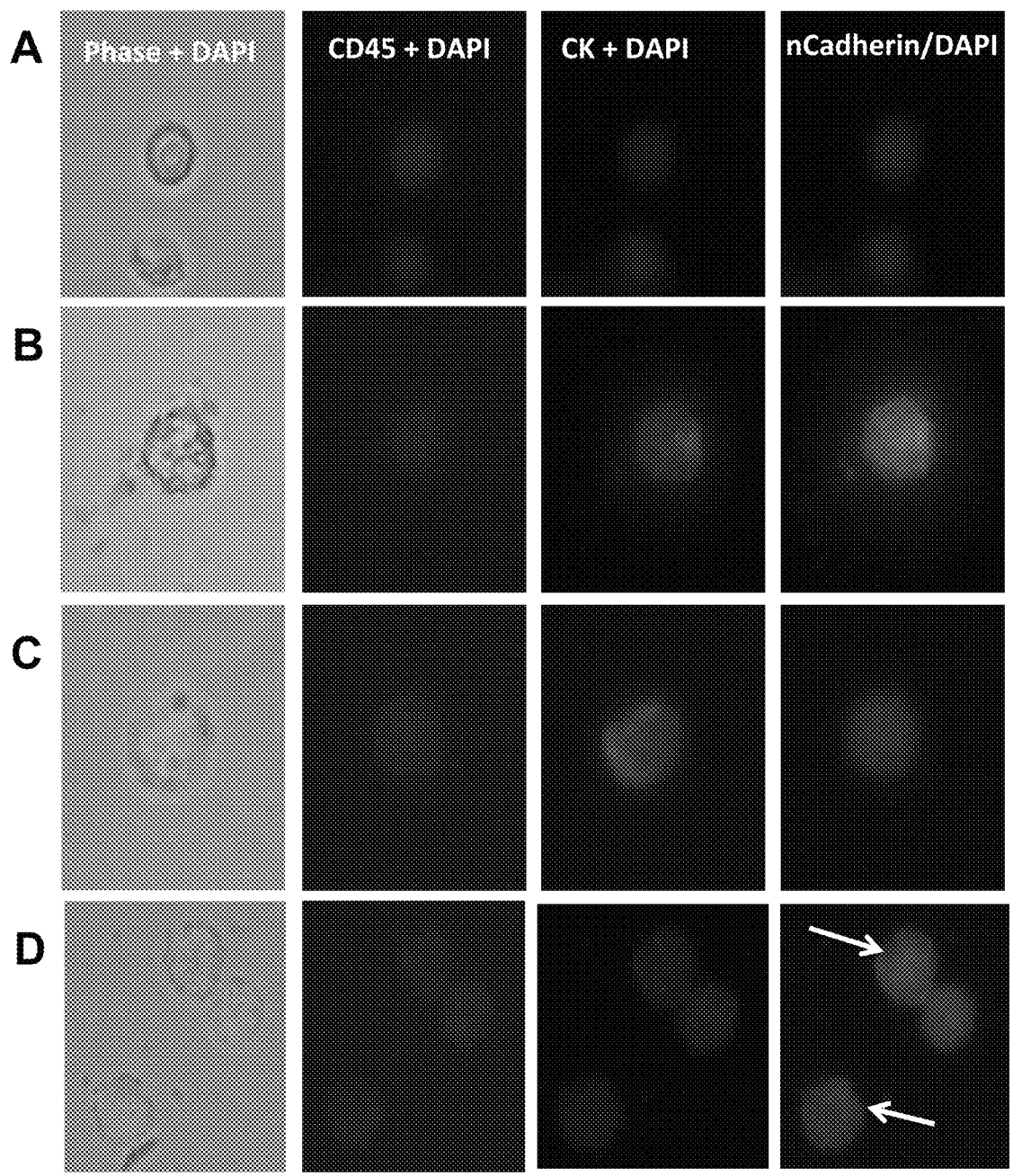
FIG. 12 depicts immunofluorescent images of CTCs from patients with mCRPC and mBC.
Figure 13:
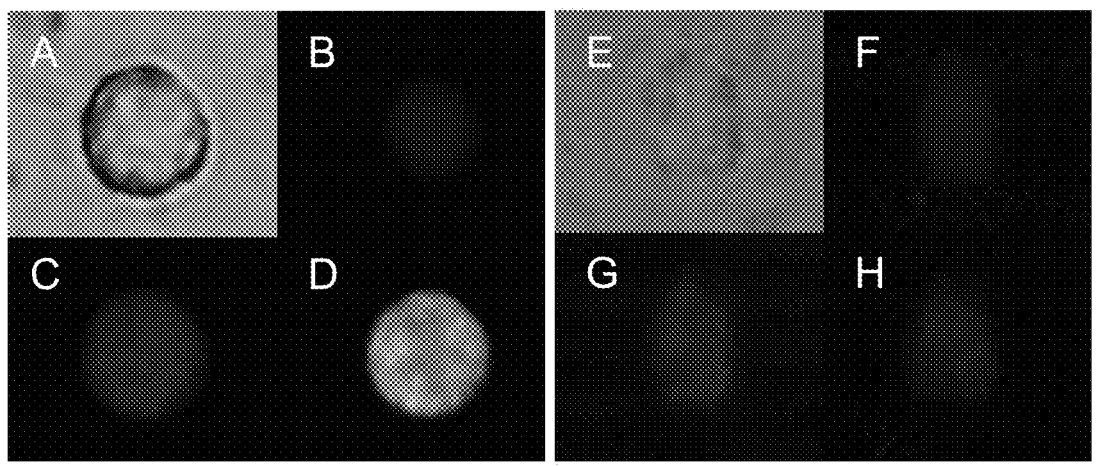
FIG. 13 depicts immunofluorescent images of CTCs from patients with mCRPC and mBC.

Prevalence of vimentin and CK co-expression in CTCs, and prevalence of N-cadherin and CK co-expression in CTCs are presented in Tables 8 and 9, respectively. Vimentin co-expression was detected in 17/20 (85%) patients with mCRPC or mBC and 78% of all CTCs. N-Cadherin co-expression was detected in 8/9 (89%) patients and 81% of CTCs. Immunofluorescent images of CTCs from patients with mCRPC and mBC are shown in FIG. 11 (A, a leukocyte; B, vimentin negative CTC (CRPC); C, vimentin positive CTC (BC); and D) vimentin positive CTC (CRPC)). Immunofluorescent images of CTCs from patients with mCRPC and mBC are shown in FIG. 12 (A, leukocyte; B, Ncad positive CTC (BC); C, Ncad negative CTC (BC); and D, two NCad positive CTCs (arrows) and 1 Ncad negative CTC (CRPC)). Immunofluorescent images of CTCs from patients with mCRPC and mBC are shown in FIG. 13 (A, Phase/DAPI; B, CD45/DAPI; C, CK/DAPI; D, Vimentin/DAPI positivity in a man with mCRPC; E, Phase/DAPI; F, CD45/DAPI; G, CK/DAPI; and H, Vimentin/DAPI negativity in a second man with mCRPC).

The data showed the co-expression of cytokeratin with the EMT antigens vimentin and N-cadherin in CTCs from men with metastatic CRPC and women with metastatic breast cancer. A majority of CTCs examined co-expressed CK and EMT proteins by immunofluorescent labeling. The majority of patients in this study had CTCs that co-expressed vimentin or N-cadherin suggesting potential epithelial plasticity during metastasis. The data suggests that CTCs can lack epithelial markers and provide methods for assessing patients with breast and prostate cancer as well as for the optimal detection of circulating tumor cells in other common malignancies.

TABLE 8

| Subject Number | | CTC Count (Cellsearch) | Ratio of: Vimentin (+) CTCs/ Total Manual CTC Count |
|---|---|---|---|
| castrate-resistant | 1 | 5 | 4/6 |
| metastatic | 2 | 4 | 2/2 |
| prostate cancer | 3 | 54 | 11/11 |
| | 4 | 45 | 6/10 |
| | 5 | 626 | 5/8 |
| | 6 | 110 | 17/21 |
| | 7 | 182 | 5/6 |
| | 8 | 17* | 13/16 |
| | 9 | 19 | 33/34 |
| | 10 | 34 | 12/12 |
| Total | | 1127 | 108/126 (86%) |
| metastatic | 1 | 13 | 0/6 |
| breast cancer | 2 | 85 | 2/2 |
| | 3 | 8 | 4/4 |
| | 4 | 21 | 1/2 |
| | 5 | 12 | 2/2 |
| | 6 | 188 | 21/22 |
| | 7 | 324** | 29/33 |

TABLE 8-continued

| Subject Number | CTC Count (Cellsearch) | Ratio of: Vimentin (+) CTCs/ Total Manual CTC Count |
|---|---|---|
| 8 | 377 | 6/23 |
| 9 | 0 | 0/0 |
| 10 | 3 | 0/3 |
| Total | 884 | 65/97 (67%) |
| Overall Total | — | 173/223 (78%) |

TABLE 9

| Subject Number | | CTC Count (Cellsearch) | Ratio of: N-Cadherin (+) CTCs/ Total Manual CTC Count |
|---|---|---|---|
| castrate-resistant metastatic prostate cancer | 1 | 45 | 13/19 |
| | 2 | 12 | 5/7 |
| | 3 | 10 | 8/8 |
| | 4 | 5 | 8/9 |
| | 5 | 12 | 4/4 |
| | 6 | 221 | 11/13 |
| | 7 | 828 | 81/96 |
| Total | | 1132 | 130/156 (83%) |
| metastatic breast cancer | 1 | 1062 | 9/13 |
| | 2 | 2 | 0/3 |
| Total | | 1064 | 9/16 (56%) |
| Overall Total | | — | 139/172 (81%) |

*Count from 3 months prior to baseline (no intervening therapy)
**Count from time point #2

In a second trial to test for the existence of transitional CTCs, blood was collected from 31 men with mCRPC and 16 women with mBC (see baseline characteristics for the patients in Table 10 and Table 11). CTCs were processed using the CELLSEARCH® EpCAM-based immunocapture method and profiled for expression of CD45 (PTPRC) (a leukocyte marker), cytokeratins (CK) (epithelial markers), vimentin (VIM) and N-cadherin (CDH2) (mesenchymal markers), and CD133 (a stem cell marker) by immunofluorescence (IF) (Table 2). Leukocytes were defined as nucleated (DAPI positive), CD45-positive and CK-negative cells, whereas CTCs were defined as nucleated (DAPI positive), CD45-negative and CK-positive cells. Among CTCs we identified transitional cells as those that additionally expressed vimentin or N-cadherin.

TABLE 10

Baseline demographic and clinical characteristics of the men with metastatic CPRC.

| | n = 31 |
|---|---|
| DEMOGRAPHICS | |
| Age, years (range) | 71 (59-89) |
| Race, Ethnicity | |
| White, non-Hispanic | 71% |
| Black, non-Hispanic | 29% |
| BASELINE DISEASE HISTORY | |
| Median Gleason Score (range) | 8 (5-10) |
| Median Baseline PSA[1] (ng/dl, range) | 267.5 (14.0-13,419.5) |
| Median Baseline Pain (range)[2] | 1 (0-7) |

TABLE 10-continued

Baseline demographic and clinical characteristics of the men with metastatic CPRC.

| | n = 31 |
|---|---|
| Median Karnofsky Performance Status (range) | 90 (60-100) |
| Median Number of Prior Hormonal Therapies (range) | 3 (0-5) |
| Prior Chemotherapy | 65% |
| Prior Bisphosphonates | 71% |
| SITES OF METASTATIC DISEASE | |
| Visceral (lung + liver) | 35% |
| Lymph Node Only | 0% |
| Bone metastatic: | |
| Bone Metastatic With Lymph Nodes (no visceral metastases) | 39% |
| Bone Metastatic Without Lymph Nodes (no visceral metastases) | 26% |

[1]PSA: prostate specific antigen.
[2]Pain is scored as a linear analog scale (0-10 range).

TABLE 11

Baseline characteristics of mBC patients.

| | n = 16 |
|---|---|
| DEMOGRAPHICS | |
| Median age (range) | 61 (48-81) |
| Race, Ethnicity | |
| White, non-Hispanic | 44% |
| Black, non-Hispanic | 50% |
| Asian, non-hispanic | 6% |
| BASELINE DISEASE HISTORY | |
| ER and/or PR positive disease | 56% |
| HER2 positive disease (HER2 3+) | 0% |
| Median Karnofsky Performance Status (range) | 90 (70-90) |
| Median Number of Prior Endocrine Therapies (range) | 1 (0-4) |
| Median Number of Prior Chemotherapies | 2 (0-7) |
| SITES OF METASTATIC DISEASE | |
| Visceral (lung or liver) | 75% |
| Lymph Node Only | 0% |
| Lymph Node, soft tissue, or contralateral breast only | 13% |
| Bone metastases only: | |
| Bone Metastatic With Lymph Nodes (no visceral metastases) | 0% |
| Bone Metastatic Without Lymph Nodes (no visceral metastases) | 13% |

Figure 14:
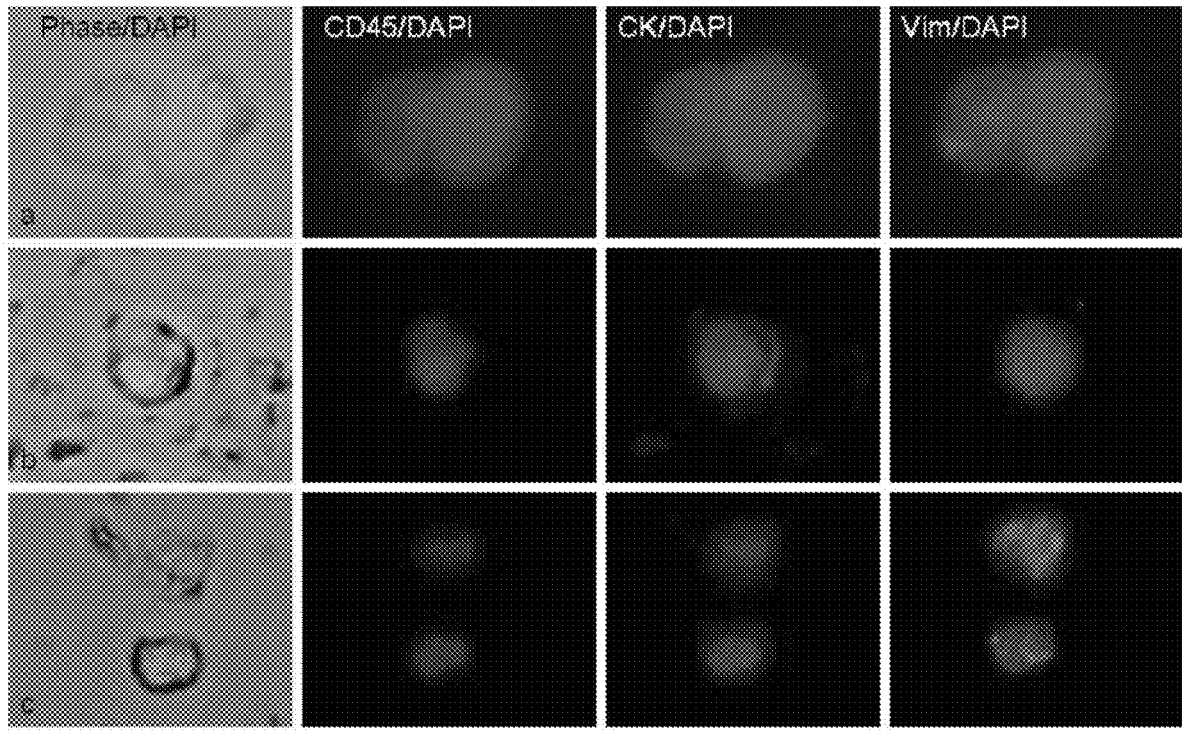
FIG. 14 depicts immunofluorescent images of CTCs from patients with mCRPC and mBC.
Figure 14:
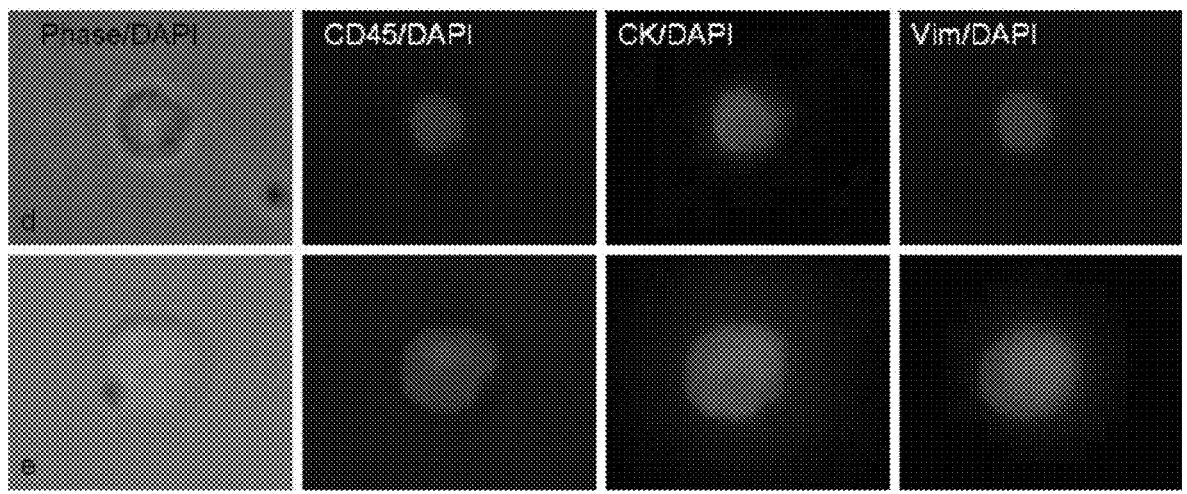

Among ten men with mCRPC, CTCs co-expressed vimentin and CK in 10/10 (100%) patients, and by this criterion 108/126 (86%) of enumerated CTCs were transitional (Table 12, FIG. 14). Biopsies of bony metastases performed within one week of CTC collection in two of these patients revealed no vimentin expression in the CK positive tumor foci, but strong vimentin expression in the surrounding bone stroma, which lacks CK expression. These same patients had CTCs taken at the same time as the CT-guided tumor biopsy that commonly expressed co-expressed CK and vimentin. These findings are consistent with invasion and metastasis by transitional CTCs that subsequently undergo MET; alternatively, vimentin expression may be heterogeneously expressed in metastases, similar to CTC expression.

TABLE 12

Circulating tumor cell (CTC) and transitional CTCs in patients with metastatic CRPC.

| Subject Number | CTC Count (Cellsearch)[i] | Ratio: Vimentin (+) CTCs/ Total Manual CTC Count[ii] |
|---|---|---|
| 1 | 5 | 4/6 |
| 2 | 4 | 2/2 |
| 3 | 54 | 11/11 |
| 4 | 45 | 6/10 |
| 5 | 626 | 5/8 |
| 6 | 110 | 17/21 |
| 7 | 182 | 5/6 |
| 8 | 17 | 13/16 |
| 9 | 19 | 33/34 |
| 10 | 34 | 12/12 |
| Total | 1127 | 108/126 (86%) |

| Subject Number | CTC Count (Cellsearch) | Ratio: N-Cadherin (+) CTCs/ Total Manual CTC Count |
|---|---|---|
| 11 | 45 | 13/19 |
| 12 | 12 | 5/7 |
| 13 | 10 | 8/8 |
| 14 | 5 | 7/8 |
| 15 | 12 | 3/4 |
| 16 | 220 | 11/13 |
| 17 | 828 | 81/96 |
| 18 | 26 | 6/11 |
| 19 | 12 | 18/22 |
| 20 | 42 | 15/18 |
| Total | 1224 | 167/206 (81%) |

| Subject Number | CTC Count (Cellsearch) | Ratio: CD133 (+) CTCs/ Total Manual CTC Count |
|---|---|---|
| 21 | 485 | 38/38 |
| 22 | 16 | 6/11 |
| 23 | 91 | 15/21 |
| 24 | 6 | 0/0 |
| 25 | 36 | 29/29 |
| 26 | 27 | 9/9 |
| 27 | 43 | 10/15 |
| 28 | 2 | 0/0 |
| 29 | 23 | 12/14 |
| 30 | 38 | 23/26 |
| 31 | 30 | 12/17 |
| Total | 797 | 154/180 (86%) |

[i]The middle column represents the CTC Count from the FDA-approved CELLSEARCH® enumeration of CTCs for each subject.
[ii]Right column represents the ratio of vimentin (co-expression of vimentin ranged from 60-100% of cells in a given individual and did not correlate with CTC count ($R^2 = 0.11$)), N-cadherin (Co-expression of N-cadherin ranged from 55-100% of cells in a given individual, and did not correlate with CTC count ($R^2 = -0.09$)), or CD133 (CD133 co-expression ranged from 55-100% of evaluable cells in a given individual and did not correlate with CTC number ($R^2 = 0.04$)) expressing CTCs among the total number of CTCs that were manually enumerated. A CTC was defined as an intact DAPI positive (nucleated) cell that lacked CD45 expression and expressed cytokeratin.

TABLE 13

CTCs and transitional CTCs in patients with mBC.

| Subject Number | CTC Count (Cellsearch)[i] | Ratio: Vimentin (+) CTCs/ Total Manual CTC Count[ii] |
|---|---|---|
| 1 | 21 | 0/6 |
| 2 | 7 | 2/2 |
| 3 | 8 | 4/4 |
| 4 | 21 | 1/2 |
| 5 | 12 | 2/2 |
| 6 | 188 | 21/22 |
| 7 | 324 | 29/33 |
| 8 | 377 | 6/23 |
| 9 | 0 | 0/0 |
| 10 | 3 | 0/3 |
| Total | 961 | 65/97 (67%) |

| Subject Number | CTC Count (Cellsearch) | Ratio: N-Cadherin (+) CTCs/ Total Manual CTC Count |
|---|---|---|
| 11 | 1062 | 9/13 |
| 12 | 2 | 0/3 |
| 13 | 147 | 52/59 |
| 14 | 6 | 2/5 |
| 15 | 33 | 15/15 |
| 16 | 2 | 0/0 |
| Total | 1252 | 78/95 (82%) |

Figure 15:
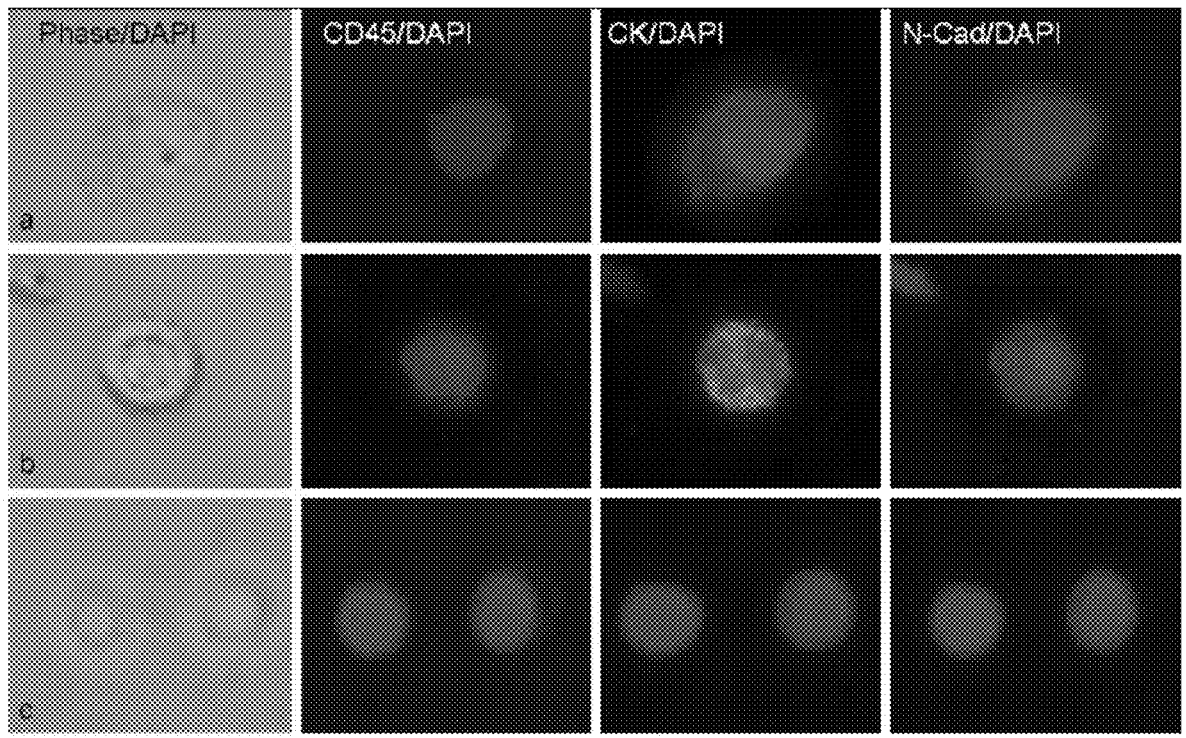
FIG. 15 depicts immunofluorescent images of CTCs from patients with mCRPC and mBC.
Figure 15:
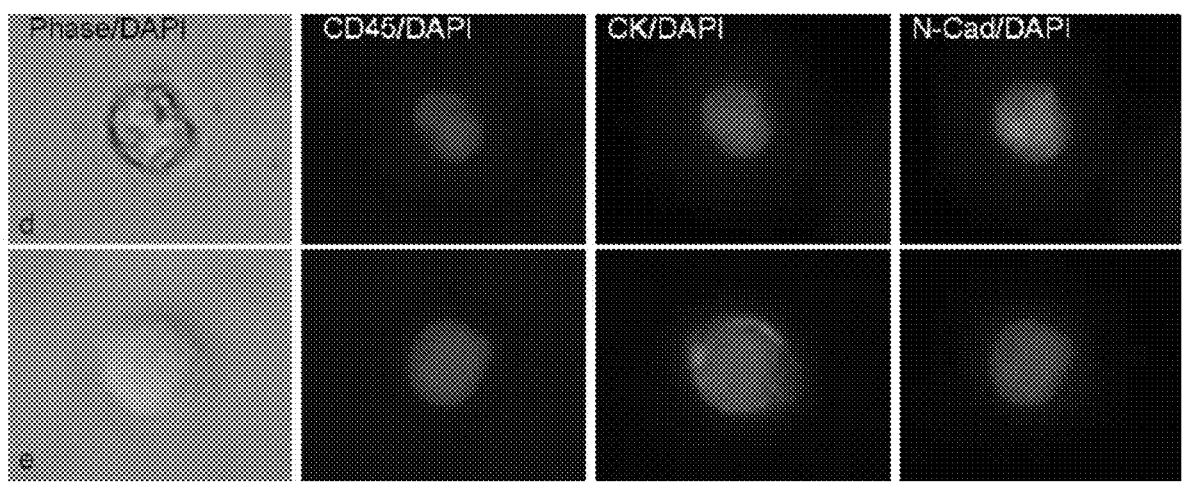

Among the next cohort of 10 men with mCRPC, CTCs co-expressed N-cadherin and CK in 10/10 (100%) patients, and by this criterion 167/206 (81%) of CTCs were identified as transitional (Table 12, FIG. 15). Among 10 women with mBC, nine had detectable CTCs and of these, we found evidence of vimentin co-expression in seven (78%) patients, and 55/88 CTCs overall (63%) co-expressed vimentin (Table 13, FIG. 14). Among another six women with detectable CTCs and mBC, four had evidence of CK and N-cadherin co-expression, and overall 78/95 CTCs (82%) had N-cadherin expression, with significant heterogeneity in expression in a given individual (Table 13, FIG. 15). These data indicate that many CTCs in patients with mBC and mCRPC co-express epithelial (EpCAM and cytokeratin) and mesenchymal (vimentin, N-cadherin) markers, and thus exist in a transitional phenotypic state, similar to that observed in our preclinical models.

Figure 16:
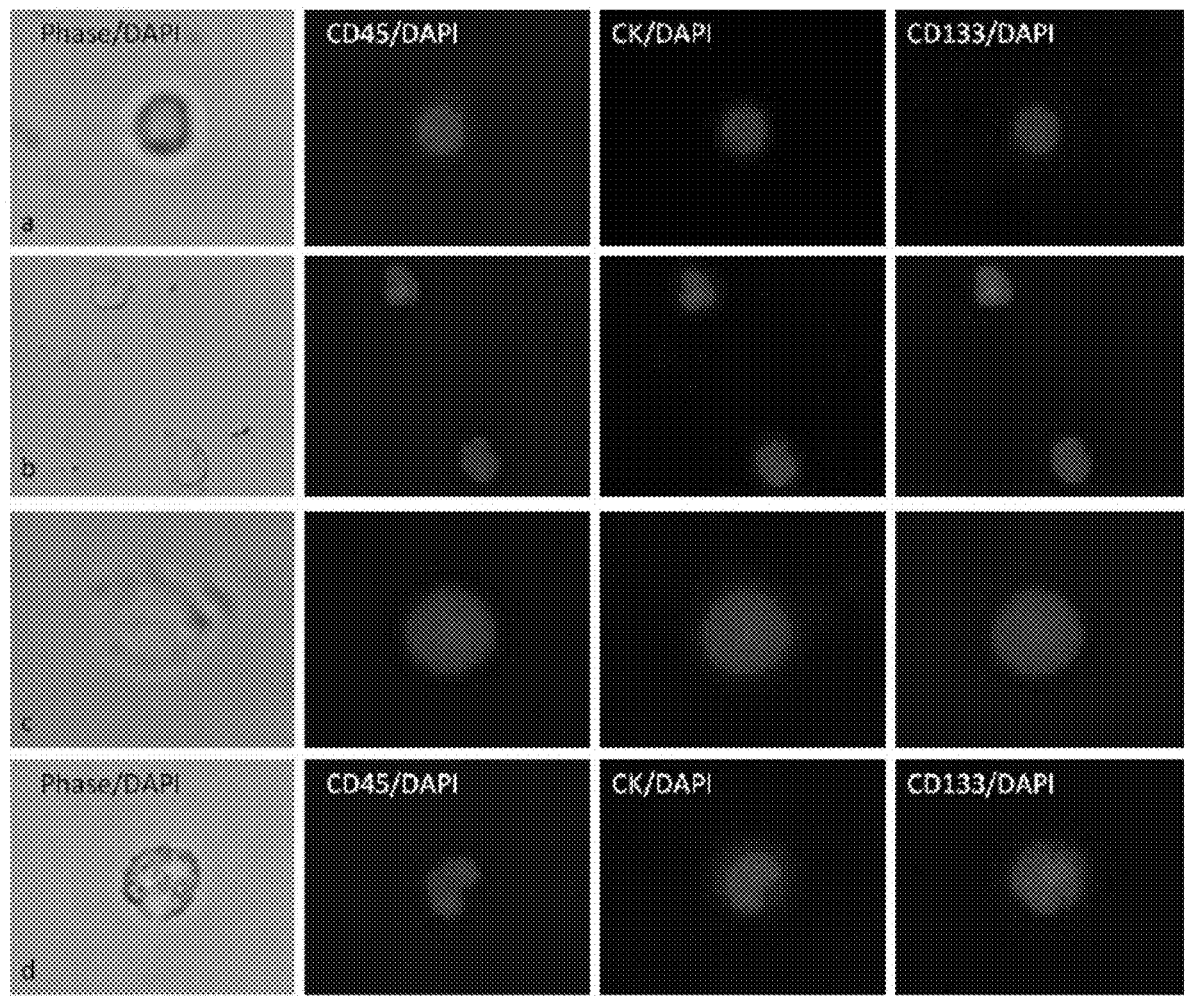
FIG. 16 depicts immunofluorescent images of CTCs from patients with mCRPC and mBC.

Given the expression of the stem cell associated antigen CD133 in transitional AT3-T cells, CD133 expression in CTCs from men with mCRPC was evaluated. CD133 was expressed in 11/11 (100%) men with CTCs, and in 154/180 (86%) of CTCs from these men (Table 12, FIG. 16). These data suggest that CTCs from patients with common epithelial malignancies inhabit transitional states characterized by co-expression of epithelial and mesenchymal markers as well as CD133, biomarkers that have been associated with stem-like properties, invasiveness, and chemoresistance.

Example 9

CTC Isolation

Antibody selection. For cell capture, several antibodies against the extracellular domain of OB-cadherin or N-cadherin were tested using positive control (PC3) and negative control (LNCaP) cell lines and analyzed by flow cytometry. The antibodies with the highest signal in the PC3 cells and minimum background with LNCaP cells were selected for conjugation to magnetic particles. The anti-OB-cadherin antibody (R&D Systems, clone 283416) and anti-N-cadherin antibody (Santa Cruz Biotechnology, D-4) were conjugated to magnetic particles using procedures similar to previously described methods (Allard et al. (2004) Clin Cancer Res 10:6897-6904; see also U.S. Pat. No. 6,645,731).

Mesenchymal capture assay. A mesenchymal capture assay was used with the CELLSEARCH® platform (Veridex LLC), including the CELLTRACKS® AUTOPREP® for sample preparation and the CELLTRACKS ANALYZER II® for analysis of the captured cells (Allard et al. (2004) Clin Cancer Res 10:6897-6904). The mesenchymal capture assay included ferrofluid coated with anti-OB-cadherin antibodies or anti-N-cadherin antibodies to produce a capture reagent, which would immunomagnetically enrich mesenchymal cells, and staining reagents, such as a phycoerythrin (PE)-conjugated antibody that binds to β-catenin (clone L54E2 from Cell Signaling Technology, Inc.); an antibody to CD45 conjugated to allophycocyanin (APC); and nuclear dye 4',6-diamidino-2-phenylindole (DAPI) to fluorescently label the cells. The assay included buffers to wash, permeabilize, and resuspend the cells such as the following components from the CELLSEARCH® kit: capture enhancement reagent, permeabilization reagent, cell fixative, and dilution buffer.

Sample Preparation. 7.5 mL of blood was transferred to 15 mL CELLTRACKS® AUTOPREP® sample tubes and mixed with 6.5 mL of dilution buffer, centrifuged at 800 g for 10 min, and then placed on the CELLTRACKS® AUTOPREP® (Veridex LLC) for automated sample preparation using the mesenchymal capture assay. After aspiration of the plasma and buffer layer by the instrument, ferrofluid was added. After the incubation period and subsequent magnetic separation, unbound cells and remaining plasma were aspirated. The target cells were enriched, fluorescently labeled, and resuspended using the CELLTRACKS® AUTOPREP® in the MAGNEST® Cell Presentation Device (Veridex LLC). The magnetic field generated by the MAGNEST® device caused the magnetically labeled cells to distribute uniformly over the analysis surface of the cartridge for analysis using the CELLTRACKS ANALYZER II®.

Sample Analysis. After ferromagnetic antibody capture, the staining reagents were added, along with a permeabilization buffer, to fluorescently label the immunomagnetically enriched cells. The cells were stained with labeled anti-β-catenin antibodies, labeled anti-CD45 antibodies, and DAPI for visualization. The anti-β-catenin antibodies was used to identify mesenchymal CTCs. After incubation on the system, the magnetic separation was repeated, and excess staining reagents were aspirated. In the final processing step, the cells were resuspended in the MAGNEST® device, which included a chamber and two magnets that oriented the immunomagnetically labeled cells for analysis using the CELLTRACKS ANALYZER II®.

Figure 17:
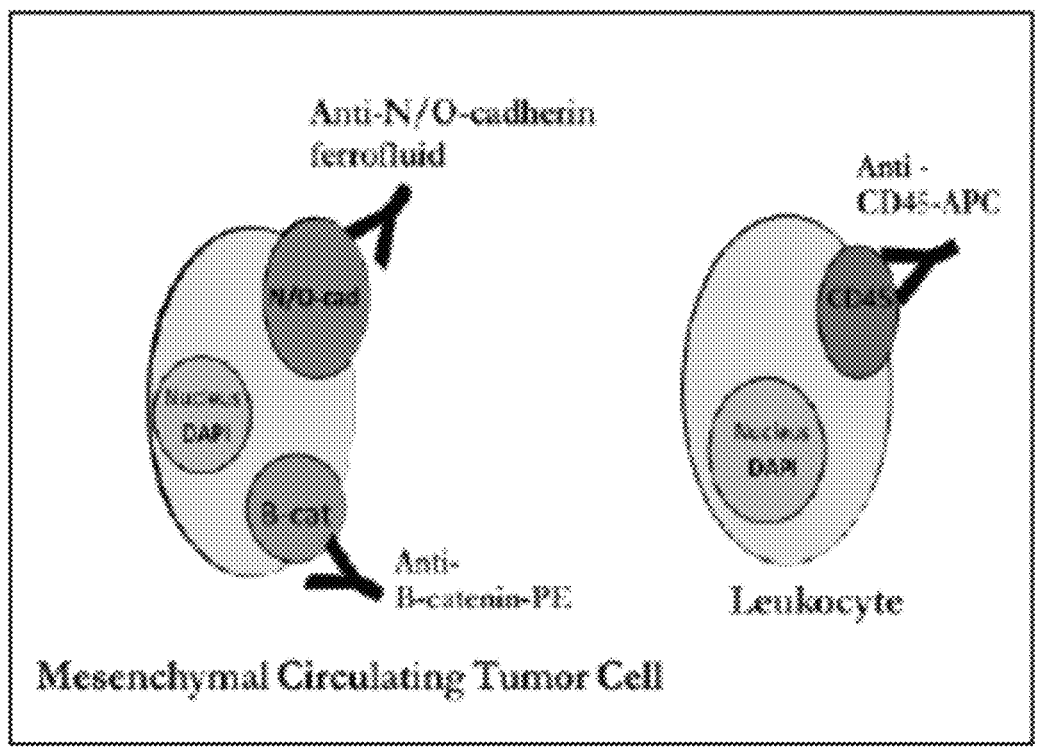
FIG. 17 depicts after enrichment using anti-N-cadherin or anti-OB-cadherin ferrofluid, mesenchymal CTCs were differentiated from leukocytes by the presence of β-catenin expression and the lack of CD45 expression.

The MAGNEST® was placed on the CELLTRACKS ANALYZER II®, a four-color semi-automated fluorescence microscope. Image frames covering the entire surface of the cartridge for each of the four fluorescent filter cubes were captured. The captured images that contained PE as well as DAPI positive events in the same frame were presented in a web-enabled browser gallery for classification of the events based on cell fluorescence and morphology. The final selection of the cells was made by the operator. The criteria to classify the object as a mesenchymal cell (designated as "events") included round to oval morphology, an intact cell greater than 4 μm with a visible nucleus (DAPI positive), positive staining for anti-β-catenin-PE, and negative staining for anti-CD45-APC, as depicted in FIG. 17. Results of cell enumeration were expressed as the number of cells per 7.5 mL of blood.

Figure 18:
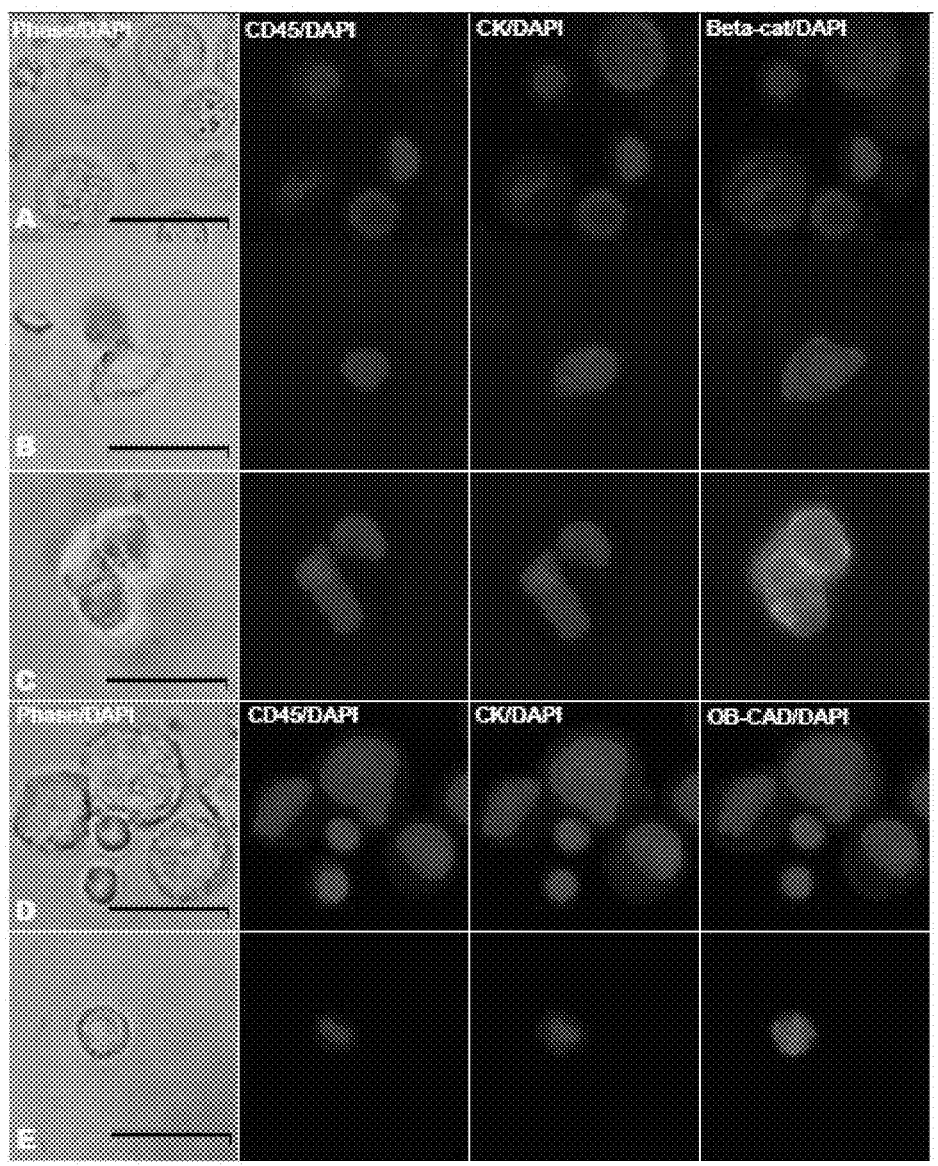
FIG. 18 depicts immunofluorescent images of control cells (PC-3 cells mixed with peripheral blood mononuclear cells) in rows A and D and patient-derived EpCAM-captured cells in rows B, C, and E. Cells are stained for CD45 and cytokeratin and further characterized by either β-catenin or OB-cadherin expression. Columns represent phase microscopy with 4′,6-diamidino-2-phenylindole (DAPI), CD45 with DAPI, Cytokeratin (CK) with DAPI, and either β-catenin (beta-cat) or OB-cadherin (OB-CAD) with DAPI. Row A shows CD45-positive control cells lacking β-catenin and CK-positive control cells expressing β-catenin. Row B shows a CTC from a man with prostate cancer with both CK and β-catenin expression, while row C shows a CD45-negative, CK-negative patient cell with β-catenin expression. Row D illustrates CD45-positive control cells lacking OB-cadherin and CK-positive control cells expressing OB-cadherin, and row E shows a CTC with both CK and OB-cadherin expression.
Figure 19:
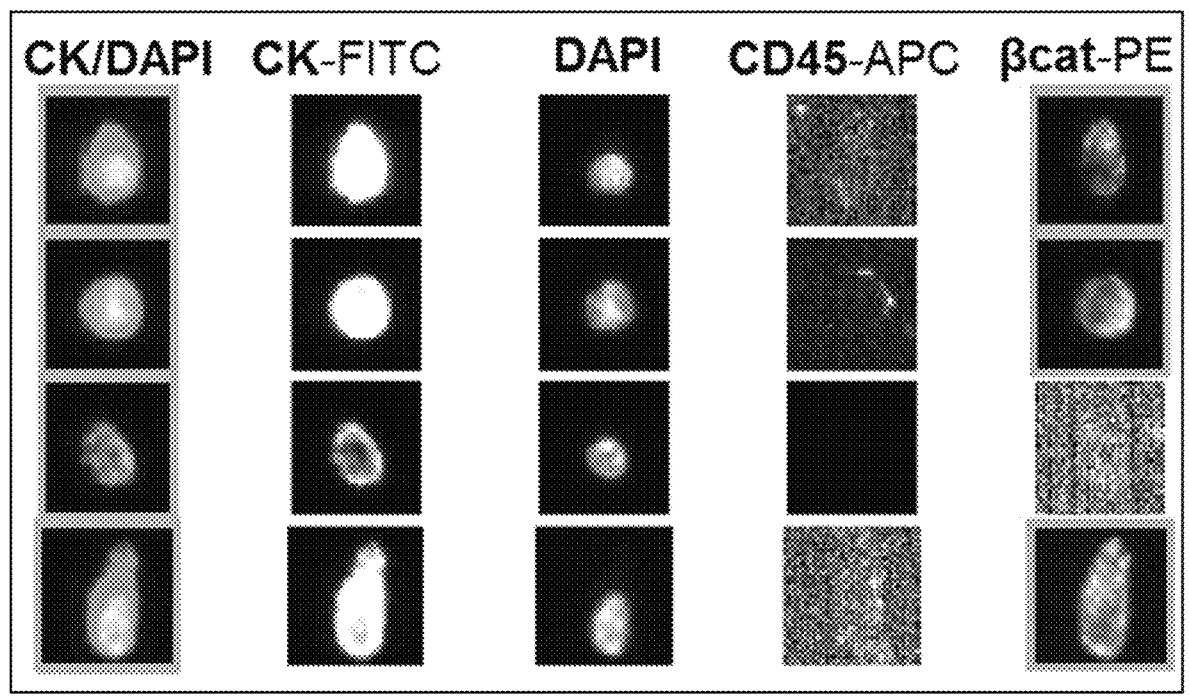
FIG. 19 depicts examples of β-catenin expression in EpCAM-captured CTCs from a man with castration-resistant prostate cancer.

An isolated "CTC" using this assay was defined as a β-catenin positive, CD45 negative, nucleated intact cell, based on our preliminary data that beta-catenin was visualized in tumor cells but not in leukocytes, as illustrated in FIG. 18. In comparison, 50-75% of EpCAM-captured CTCs stained for β-catenin, as shown in FIG. 19 (Bitting et al. (2012) J Clin Oncol 30S:abstr 10533). A mesenchymal CTC phenotype was identified using the OB-cadherin antibody or N-cadherin antibody ferrofluid to capture CTCs with positive β-catenin expression, lack of CD45 expression, and positive nuclear DAPI staining to characterize the cells.

Figure 20:
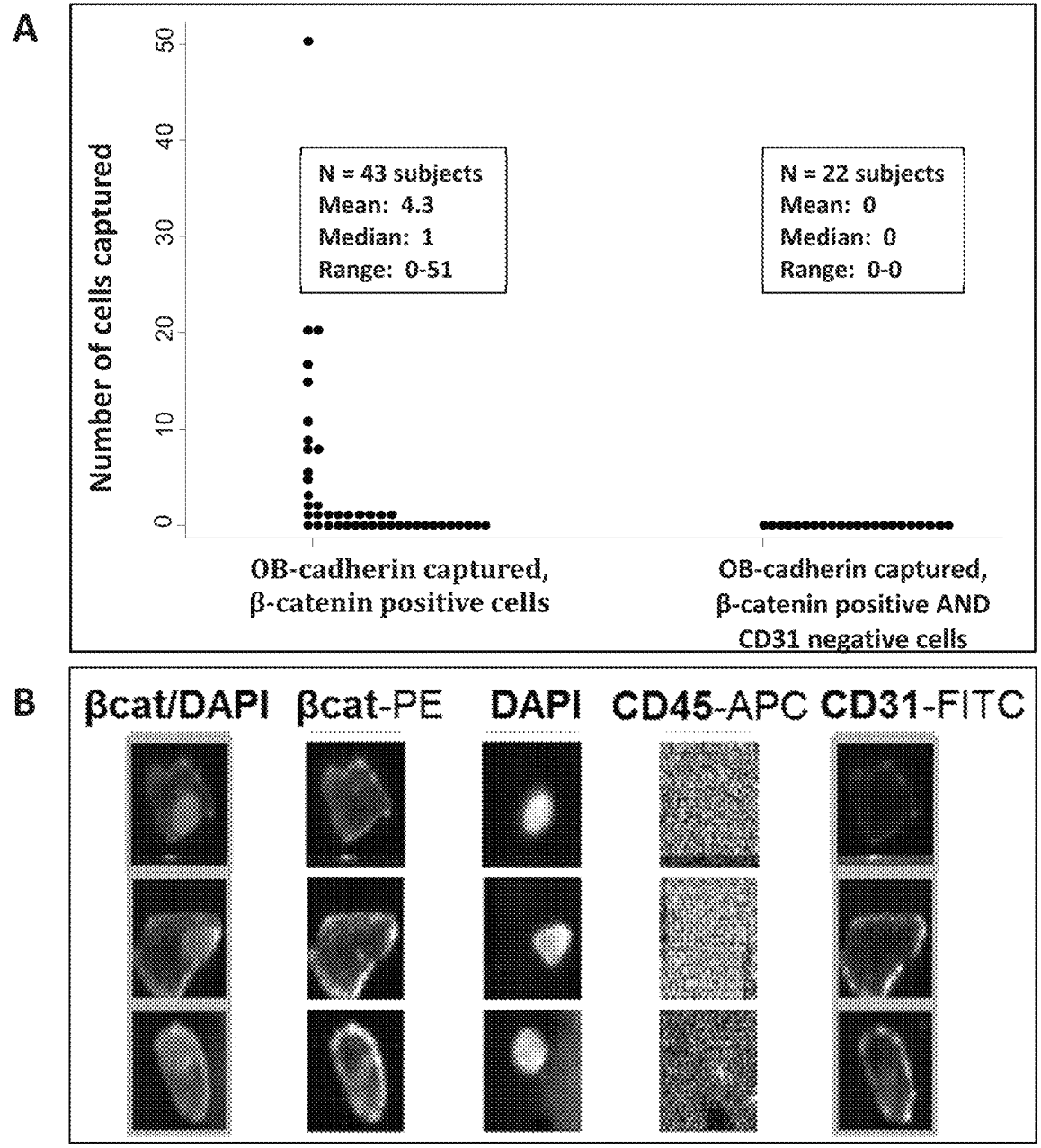
FIG. 20 depicts (A) the distribution of OB-cadherin-captured, β-catenin-positive events from healthy volunteers based on CD31 status. All samples in which CD31 was assessed are CD31 positive; and (B) examples of CD31+ cellular events detected in healthy volunteers.
Figure 21:
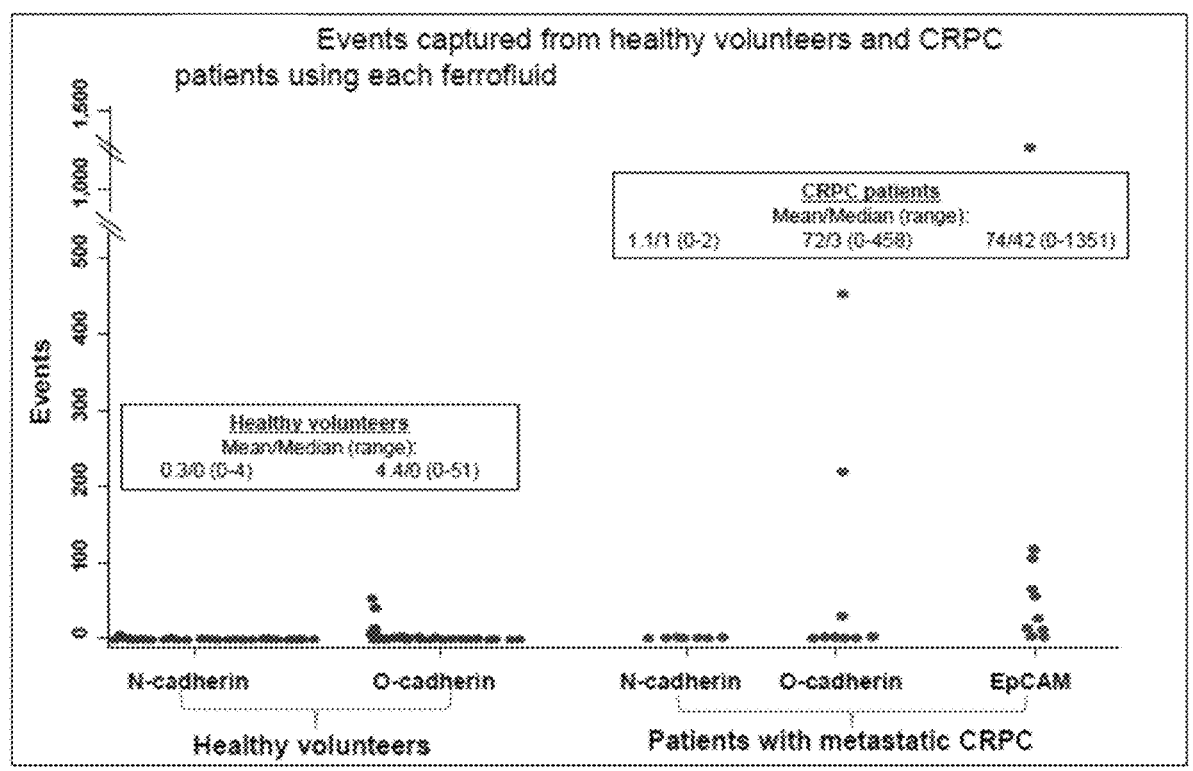
FIG. 21 depicts events captured from healthy volunteers and CRPC patients using N-cadherin, OB-cadherin, or EpCAM ferrofluid.

To determine if circulating mesenchymal-like tumor cells meeting the above criteria were present in healthy individuals, blood was drawn from healthy adults age over 18 years of age into 10 mL EDTA tubes. Subjects were not eligible if they had any chronic medical condition requiring medication or a history of cancer. Samples were processed as described above within 8 hours of blood collection. All subjects were enrolled using an institutional review board-approved protocol and provided informed consent. The OB-cadherin-captured, β-catenin-positive events ("rare events") were detected in healthy volunteers. The rare events detected in healthy volunteers were stained with the endothelial marker CD31 (BD Biosciences, clone WM59) for further characterization as previously described (Pusztaszeri et al. (2006) J Histochem Cytochem 54:385-395). All detected events in healthy volunteers were CD31 positive, which indicates that these cells may represent endothelial cells. Examples of the OB-cadherin captured, β-catenin-positive and CD31-positive events in healthy individuals are shown in FIG. 20.

After establishing a threshold for detection in healthy volunteers (zero OB-cadherin, β-catenin-positive cells if CD31 was included as an additional characterization marker), the prevalence of these cellular events was determined in men with progressive, metastatic CRPC that were enrolled in a correlative clinical blood-drawing study prior to initiating a new systemic therapy. See Table 14. This population largely was composed of men with bone metastases (>90%) and would thus theoretically be enriched for OB-cadherin positive cells, if present.

TABLE 14

| Baseline characteristics of CRPC patients | Results (n = 10) |
|---|---|
| Median age, years (range) | 68 (57-74) |
| Race | |
| Caucasian, n (%) | 7 (70) |
| Black, n (%) | 3 (30) |
| Karnofsky performance status, median (range) | 90 (80-100) |
| Gleason score, median (range) | 8 (7-10) |
| Pain score > 4, n (%) | 4 (40) |
| Initial local therapy | |
| Prostatectomy, n (%) | 3 (30) |
| External beam radiation, n (%) | 3 (30) |
| None, n (%) | 4 (40) |
| Laboratory values | |
| PSA ng/mL, median (range) | 408 (7-4377) |
| LDH U/L, median (range) | 220 (206-291) |
| Hemoglobin g/dL, median (range) | 9.8 (8.8-12.1) |
| Alkaline phosphate U/L, median (range) | 197 (57-463) |
| CTC count, median (range) | 34 (1-1000) |
| Sites of metastasis | |
| Bone, n (%) | 10 (100) |
| Liver, n (%) | 2 (20) |
| Lung, n (%) | 4 (40) |
| Lymph nodes only | 0 |

TABLE 14-continued

| Baseline characteristics of CRPC patients | Results (n = 10) |
|---|---|
| Prior therapies | |
| Number of hormonal therapies, median (range) | 4 (1-5) |
| Abiraterone, MDV3100, or TAK700, n (%) | 7 (70) |
| Siputeucel-T, n (%) | 3 (30) |
| Docetaxel, n (%) | 8 (80) |
| Cabazitaxel, n (%) | 2 (20) |
| >1 chemotherapy, n (%) | 2 (20) |
| Bone targeted therapy, n (%) | 9 (90) |
| Palliative radiation, n (%) | 3 (30) |
| Type of Progression prior to study enrollment | |
| Imaging | 8 (80) |
| Clinical (symptoms, PSA increase) | 2 (20) |

One CELLSAVE® and two EDTA 10 mL tubes of blood were collected at baseline, at treatment cycle 3, and at progression. Blood obtained in EDTA tubes was used for OB-cadherin capture in duplicate and was processed as soon as possible, with no more than 8 hrs elapsing from the time of collection. Blood obtained in the CELLSAVE® tubes was used for the standard EpCAM capture only and was processed within 72 hours, per the established protocol (Allard et al. (2004) Clin Cancer Res 10:6897-6904). Using the CELLSEARCH® system, circulating mesenchymal cells were captured with the anti-OB-cadherin ferrofluid, then permeabilized and stained for further characterization, as described above. Cells were enumerated per 7.5 mL of blood, and the mesenchymal CTC enumeration was compared with the standard EpCAM-based capture method. Any discrepancy in the scoring of events was resolved with discussion between two independent reviewers.

Figure 22:
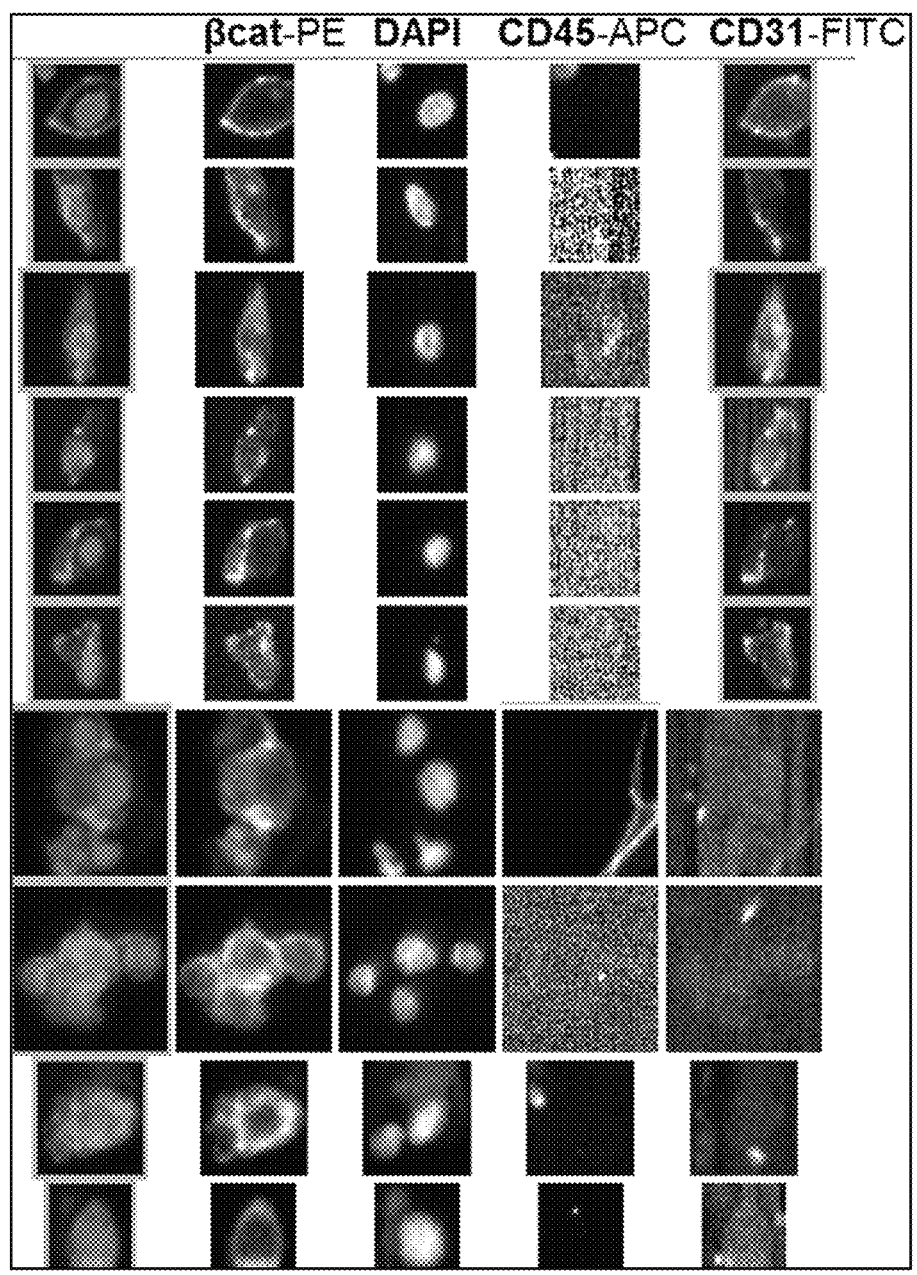
FIG. 22 depicts examples of OB-cadherin captured, β-catenin-positive cellular events from men with metastatic castration-resistant prostate cancer. The top rows show single cells which are mostly CD31-positive and may represent endothelial cells, while the bottom rows show clumps of CD31-negative cells which may represent mesenchymal tumor cells.

The EpCAM-based capture assay detected more tumor cells in the majority of patients, however there were exceptions in which more mesenchymal events were seen. Also, OB-cadherin capture resulted in more sheets or clumps of cells and multiple cells per field than EpCAM capture, as illustrated in FIG. 22.

As shown in Table 15, rare events were detected in healthy volunteers using the mesenchymal capture methods. In CRPC patients, OB-cadherin capture ("O-cad capture") detected more events in 3 of 5 subjects than EpCAM-based capture, and the majority of captured cells were cytokeratin negative.

TABLE 15

| | O-cad capture, beta-catenin+ | N-cad capture, beta-catenin+ | EpCAM capture, cytokeratin+ |
|---|---|---|---|
| Healthy Volunteers | 0-51 events (mean 5.95) n = 21 | 0-4 events (mean 0.28) n = 25 | NA |
| CRPC patients | 0-465 events (mean 138.4) n = 5 | 0-2 events (mean 1.2) n = 5 | 1-123 CTCs (mean 50.8) n = 5 |

Table 16 shows events captured of cells in the blood from CRPC patients using the N-cadherin ("N-cad") and OB-cadherin ("O-cad") ferrofluid. The number of cells captured from the CRPC patients appeared to be higher in some patients as compared with the EpCAM-based technology, and the rate of detection appeared higher than that in healthy volunteers for at least OB-cadherin capture.

TABLE 16

| Subject | N-cad Capture #events | N-cad Capture CD31+ | O-cad capture #events | O-cad capture CD31+ | EpCAM Capture #events | EpCAM Capture CD31+ | CELLSEARCH® standard-of-care |
|---|---|---|---|---|---|---|---|
| 1 | 2 | na | 4 | na | 102 | na | 46 |
| 2 | 1 | na | 458 | na | 71 | na | 45 |
| 3 | 2 | na | 3 | na | 2 | na | 7 |
| 4 | 0 | — | 0 | — | 31 | na | 50 |
| 5 | 1 | na | 220 | na | 17 | na | 23 |
| 6 | 1 | 1 | 3 | 0 | 1351 | na | >1000 |
| 7 | na | na | 1 | 0 | 0 | — | 1 |
| 8 | 2 | 0 | 0 | — | 53 | 1 | 22 |
| 9 | 0 | — | 29 | 29 | 9 | 0 | 12 |
| 10 | na | na | 2 | 1 | 111 | 1 | 69 |

Example 10

Figure 23:
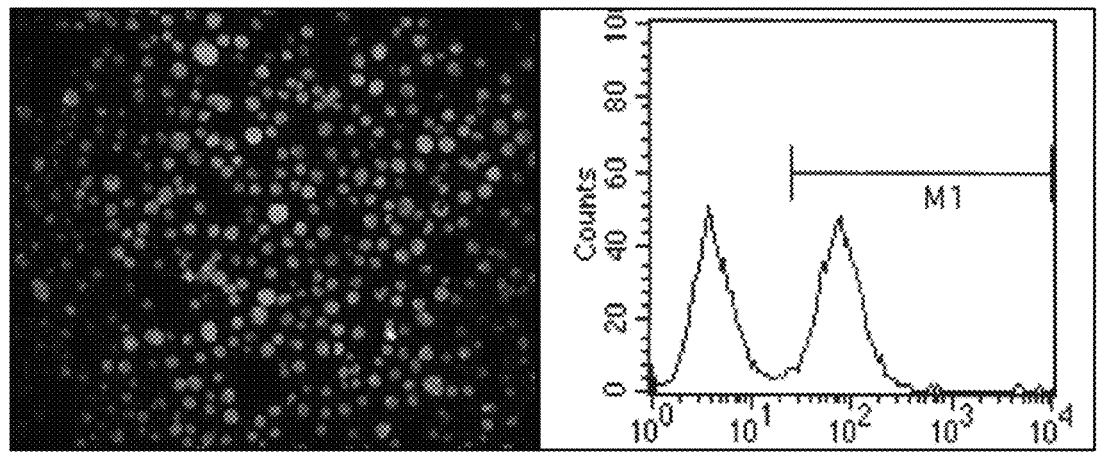
FIG. 23 depicts (A) immunofluorescent images of PC-3 cells stained for OB-cadherin (green) and DAPI/nucleus (blue), illustrating that PC-3 cells are somewhat heterogeneous for OB-cadherin expression; and (B) fluorescence-activated cell sorting of PC-3 cells based on OB-cadherin expression shows that approximately 50% of the cells express OB-cadherin.

To verify that the mesenchymal capture assay using anti-OB-cadherin antibodies could isolate and detect the cells of interest, spiking studies of positive and negative control cells were performed. Preliminary data investigating OB-cadherin expression on the prostate cancer PC-3 cell line revealed OB-cadherin expression on approximately 40-50% of PC3 cells by both immunofluorescence and flow cytometry, as shown in FIG. 23.

The prostate cancer cell line PC-3 was cultured in flasks containing DMEM high-glucose supplemented with 10% fetal calf serum and subsequently harvested using cell dissociation buffer (Gibco Cat. No. 13150-016) per package insert. Cells were counted on a hemocytometer and either 500 or 1,000 cells were spiked into 7.5 mL of blood obtained from healthy volunteers as described above. A median of 31.4% (range 16.1-103.4, n=13) of spiked cells were recovered using OB-cadherin capture and characterization as beta-catenin positive, CD45 negative cells as above.

Figure 24:
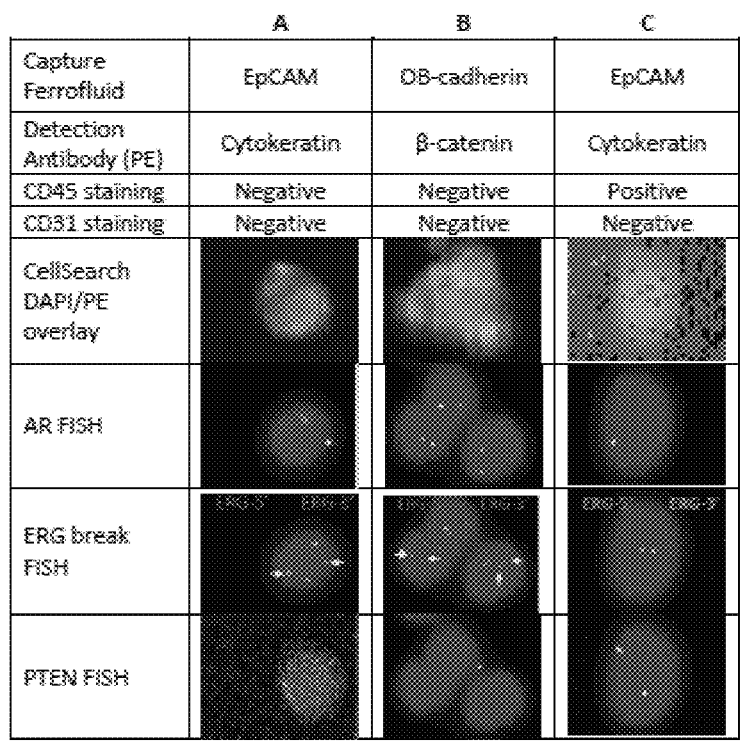
FIG. 24 depicts immunostaining and fluorescent in situ hybridization (FISH) results from a representative patient with metastatic castration-resistant prostate cancer. Columns A and B—Circulating cells captured with OB-cadherin and stained with β-catenin show same multigene FISH pattern as a CTC captured with EpCAM and stained with cytokeratin from the same patient. Androgen receptor (AR) FISH shows extra copies of the androgen receptor gene. For the ERG break FISH, yellow arrows denote missing 5' Erg signals which is indicative of TMPRSS2:ERG fusion. PTEN FISH shows homozygous deletion of PTEN gene. Column C—leukocyte from the same patient shows a cytokeratin-negative cell with a normal FISH pattern of 1 AR signal, no ERG rearrangement, and two copies of PTEN.

The collection of the mesenchymal phenotypic CTC left open the possibility that cellular events were not cancer cells, but rather host cells. For example, in healthy volunteers, the OB-cadherin positive cells were most likely endothelial cells derived from phlebotomy as they were CD31 positive. In men with metastatic CRPC (mCRPC), these OB-cadherin positive cells could be endothelial or circulating osteoblasts, bone marrow derived mesenchymal cells, or other circulating mesenchymal-like cells expressing OB-cadherin. To determine the significance of OB-cadherin captured events from patients and whether these cellular events represented host cells or prostate cancer cells, DNA fluorescence in situ hybridization (FISH) was performed for prostate cancer-specific genomic events. Cellular events were identified using the CELLTRACKS ANALYZER II® as described above and then fixed and dried on the cartridge for DNA FISH. Using a 4-color FISH assay for androgen receptor (AR) amplification, PTEN loss, and gene fusion involving the TMPRSS2-ERG locus (ERG break-apart assay), as previously described (Attard et al. (2009) Cancer Res 69:2912-2918), the captured mesenchymal cells were evaluated for these prostate-cancer specific changes. As shown in FIG. 24, AR amplification and the TMPRSS2-ERG fusion were present in both EpCAM and OB-cadherin captured cells, indicating that these cellular events were tumor-derived.

As these genomic amplification or deletion events were unlikely to be found in normal tissues, and were found in the EpCAM positive cells, these findings suggest that at least some of the OB-cadherin, beta-catenin positive cells were prostate cancer derived and not derived from the tumor microenvironment or normal host cells. Further analysis of the prevalence of these mesenchymal phenotypic CTCs in a broader population of men with mCRPC and other tumor types indicate the usefulness of this assay to complement existing CTC assays. These analyses may include comparison with EpCAM based approaches, particularly in men with low CTC counts despite progressive metastatic disease, to define the clinical utility of OB-cadherin positive events. In addition, correlations of OB-cadherin positive cellular events with clinical and pathologic characteristics and patient outcomes with systemic therapies further define the car-independent role of this assay in the context of other prognostic biomarkers. These methods and data suggested that these cells were detectable in men with mCRPC, were absent in healthy volunteers, and that the disclosed methods detected OB-cadherin positive human prostate cancer cells in blood.

The common expression of OB-cadherin in CTCs suggested osteomimicry, and provided some insight into the mechanism of prostate cancer homing to bone and the development of osteoblastic bone metastases. OB-cadherin events in healthy volunteers uniformly expressed the endothelial marker CD31, whereas the CD31 status in patients with cancer was more variable. Additional markers may be used to confirm that these mesenchymal-like cells were tumor cells (e.g., FISH, cytokeratin, PSA).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A kit for isolating or capturing a circulating tumor cell in a biological sample, the kit comprising:
    an antibody linked to a magnetic particle, wherein the antibody binds specifically to at least one epithelial-mesenchymal transition (EMT) biomarker; and
    a detectably labelled anti-β-catenin antibody and a detectably labelled anti-CD31 antibody, wherein the detectably labelled anti-β-catenin antibody and the detectably labelled anti-CD31 antibody allow detection of β-catenin and CD31 on an intact cell to determine whether the intact cell is a circulating tumor cell.

2. The kit of claim 1, wherein the at least one EMT biomarker is at least one of OB-cadherin, N-cadherin, vimentin, E-cadherin, FGFR2 splice variant isoforms, or CD133.

3. The kit of claim 1, wherein the detectably labelled anti-β-catenin antibody comprises a phycoerytherin-labelled anti-β-catenin antibody.

4. The kit of claim 1, wherein the kit further comprises DAPI, at least one additional detectably labelled antibody, or a combination thereof.

5. The kit of claim 1, wherein the detectably labelled anti-β-catenin antibody comprises a detectable label selected from a radioactive label, enzymatic label, chemiluminescent label, fluorescent label, rhodamine, phycobiliproteins, R-phycoerythrin, quantum dots, thermometric label, and an immuno-polymerase chain reaction label.

6. The kit of claim 5, wherein the radioactive label is selected from 3H, 14C, 32P, 33P, 35S, 90Y, 99Tc, 111In, 125I, 131I, 177Lu, 166Ho, and 153Sm.

7. The kit of claim 5, wherein the enzymatic label is selected from horseradish peroxidase, alkaline peroxidase, and glucose 6-phosphate dehydrogenase.

8. The kit of claim 5, wherein the chemiluminescent label is selected from acridinium ester, thioester, sulphonamide, luminol, isoluminol, and phenanthridinium ester.

9. The kit of claim 5, wherein the fluorescent label is selected from 5-fluorescein, 6-carboxyfluorescein, 3'6-carboxyfluorescein, 5(6)-carboxyfluorescein, 6-hexachlorofluorescein, 6-tetrachlorofluorescein, and fluorescein isothiocyanate.

10. The kit of claim 4, wherein the at least one additional detectably labelled antibody is a detectably labelled anti-CD45 antibody.

11. A kit for isolating or capturing a circulating tumor cell in a biological sample, the kit comprising:
    an antibody linked to a magnetic particle, wherein the antibody binds specifically to at least one epithelial-mesenchymal transition (EMT) biomarker, and wherein the at least one EMT biomarker is at least one of OB-cadherin, N-cadherin, vimentin, FGFR2 splice variant isoforms, or CD133; and
    a detectably labelled anti-β-catenin antibody and a detectably labelled anti-CD31 antibody, wherein the detectably labelled anti-β-catenin antibody and the detectably labelled anti-CD31 antibody allow detection of β-catenin and CD31 on an intact cell to determine whether the intact cell is a circulating tumor cell.

12. The kit of claim 10, wherein the detectably labelled anti-CD45 antibody and the detectably labelled anti-CD31 antibody each independently comprises a detectable label selected from a radioactive label, enzymatic label, chemiluminescent label, fluorescent label, rhodamine, phycobiliproteins, R-phycoerythrin, quantum dots, thermometric label, and an immuno-polymerase chain reaction label.

13. The kit of claim 10, wherein the detectably labelled anti-CD45 antibody comprises an allophycocyanin-labelled anti-CD45 antibody.

14. The kit of claim 11, wherein the kit further comprises DAPI and an allophycocyanin-labelled anti-CD45 antibody, and wherein the detectably labelled anti-β-catenin antibody comprises a phycoerytherin-labelled anti-β-catenin antibody.

15. The kit of claim 11, wherein the circulating tumor cell is a prostate cancer cell.

16. The kit of claim 11, further comprising a detectably labelled anti-CD45 antibody, or a detectably labelled anti-cytokeratin antibody, or DAPI, or a combination thereof.

17. The kit of claim 15, wherein the EMT biomarker is OB-cadherin.

18. The kit of claim 15, further comprising probes for detecting a prostate cancer-specific genomic event.

19. The kit of claim 18, wherein the prostate cancer-specific genomic event is selected from the group consisting of androgen receptor amplification, phosphatase and tensin homolog (PTEN) loss, gene fusion of transmembrane protease, fusion of serine 2 (TMPRSS2) gene, and ETS related (ERG) gene, and combinations thereof.

* * * * *